(12) United States Patent
Goossens et al.

(10) Patent No.: US 10,370,672 B2
(45) Date of Patent: Aug. 6, 2019

(54) MEANS AND METHODS FOR REGULATING SECONDARY METABOLITE PRODUCTION IN PLANTS

(71) Applicants: VIB VZW, Ghent (BE); Universiteit Gent, Ghent (BE); Universiteit Leiden, Leiden (NL)

(72) Inventors: Alain Goossens, Lokeren (BE); Jan Mertens, Scherpenheuvel-Zichem (BE); Alex Van Moerkercke, Berchem (BE); Jacob Pollier, Ghent (BE); Johan Memelink, Leiden (NL)

(73) Assignees: VIB XVZW, Ghent (BE); UNIVERSITEIT GENT, Ghent (BE); UNIVERSITEIT LEIDEN, Leiden (NL)

( * ) Notice: Subject to any disclaimer, the term of this patent is extended or adjusted under 35 U.S.C. 154(b) by 0 days.

(21) Appl. No.: 15/119,681

(22) PCT Filed: Feb. 18, 2015

(86) PCT No.: PCT/EP2015/053407
§ 371 (c)(1),
(2) Date: Aug. 17, 2016

(87) PCT Pub. No.: WO2015/124620
PCT Pub. Date: Aug. 27, 2015

(65) Prior Publication Data
US 2017/0009249 A1    Jan. 12, 2017

(30) Foreign Application Priority Data

Feb. 18, 2014  (EP) ..................................... 14155634
Sep. 11, 2014  (EP) ..................................... 14184392

(51) Int. Cl.
C12N 15/82    (2006.01)
C07K 14/415   (2006.01)

(52) U.S. Cl.
CPC ........ *C12N 15/8243* (2013.01); *C07K 14/415* (2013.01)

(58) Field of Classification Search
None
See application file for complete search history.

(56) References Cited

U.S. PATENT DOCUMENTS

2009/0138981 A1* 5/2009 Repetti ................ C07K 14/415
                                                          800/263
2009/0222957 A1   9/2009 Apuya et al.

FOREIGN PATENT DOCUMENTS

WO    9836083 A1    8/1998
WO    9915682 A2    4/1999
WO    2007117693 A2   10/2007
WO    WO 2013/012729 A2 *   1/2013
WO    2015124620 A1    8/2015

OTHER PUBLICATIONS

Zhang et al., 2011, Plant Journal 67: 61-71.*
Tominaga-Wada et al., 2011, Plant Science 181: 471-478, with supplementary data.*
Pires and Dolan, 2010, Mol. Biol. Evolution 27: 862-874.*
Young et al., 2012, Nature 480: 520-524, with supplementary data.*
Medtr7g080780.1 sequence information, available at http://www.medicagogenome.org/feature/ Medtr7g080780.1#coding_458622-663, accessed Feb. 3, 2018.*
*Arabidopsis thaliana* bHLH25 (locus At4g37850) and NCBI/GenBank sequence, accession No. AF488567, published Apr. 24, 2003.*
Catharanthus roseus bHLH iridoid synthesis 1 mRNA, GenBank accession No. KM409646.2, published Jul. 13, 2016.*
Catharanthus roseus bHLH iridoid synthesis 2 (BIS2) mRNA, GenBank accession No. KM409645.1, published Nov. 23, 2015.*
Kondou et al., 2009, Plant Journal 57: 883-894.*
Vom Endt et al., Transcription factors controlling plant secondary metabolism: what regulates the regulators? Phytochemistry, vol. 61. No. 2, Sep. 1, 2002 (Sep. 1, 2002), pp. 107-114, Pergamon Press, GB.
Jin et al., The *Arabidopsis* bHLH25 and bHLH27 transcription factors contribute to susceptibility to the cyst nematode Heterodera schachtii, Plant Journal, vol. 65, No. 2, Jan. 2011, pp. 319-328.
Database UniProt [Online], Jan. 25, 2012 (Jan. 25, 2012), SubName: Full=Helix loop helix, DNA-binding domain protein, {EC0:0000313:EMBL:AES80453.1}; SubName: Full=Uncharacterized protein {EC0:0000313:Ensembl Plants: AES80453}; XP002738508, retrieved from EBI accession No. Uniprot:G7KSG4, Database accession No. G7KSG4 & Young Nevin D et al., The Medicago genome provides insight into the evolution of rhizobial symbioses, Nature (London), vol. 480, No. 7378, Dec. 2011, pp. 520-524.
Yang et al., Transcriptional Regulation of Plant Secondary Metabolism, Journal of Integrative Plant Biology, vol. 54, No. 10, Oct. 2012, pp. 703-712.
Zhang et al., The basic helix-loop-helix transcription factor CrMYC2 controls the jasmonate-responsive expression of the ORCA genes that regulate alkaloid biosynthesis in Catharanthus roseusu, Plant Journal, vol. 67, No. 1, Jul. 2011, pp. 61-71.
PCT International Search Report, PCT/EP2015/053407 dated May 19, 2015.
PCT International Written Opinion, PCT/EP2015/053407 dated May 19, 2015.
Heim et al., The Basic Helix-Loop-Helix Transcription Factor Family in Plants: A Genome-Wide Study of Protein Structure and Functional Diversity, 2003 Mol. Biol. Evol. 20:735-747.

(Continued)

*Primary Examiner* — Bratislav Stankovic
(74) *Attorney, Agent, or Firm* — Patent Law Works LLP

(57) ABSTRACT

This disclosure relates to the field of secondary metabolite production in plants. More specifically, the disclosure relates to chimeric genes and their use in the regulation of biosynthesis and/or production of secondary metabolites in plants and plant-derived cell cultures.

5 Claims, 12 Drawing Sheets

Specification includes a Sequence Listing.

(56) References Cited

OTHER PUBLICATIONS

Collu, et al. "Activity of the Cytochrome P450 Enzyme Geraniol 10-Hydroxylase and Alkaloid Production in Plant Cell Cultures." Plant Science Limerick. 162.1 (2002).

Collu et al. "Geraniol 10-Hydroxylase[1], a Cytochrome P450 Enzyme Involved in Terpenoid Indole Alkaloid Biosynthesis." Febs Letters. 5082 (2001): 215-220. Print.

Hofer, et al. "Geraniol Hydroxylase and Hydroxygeraniol Oxidase Activities of the Cyp76 Family of Cytochrome P450 Enzymes and Potential for Engineering the Early Steps of the (seco)iridoid Pathway" Metabolic Engineering. 20 (2013): 221-232.

Sung, Pin-Hui, Fong-Chin Huang, Yi-Yin Do, and Pung-Ling Huang. "Functional Expression of Geraniol 10-Hydroxylase Reveals Its Dual Function in the Biosynthesis of Terpenoid and Phenylpropanoid." Journal of Agricultural and Food Chemistry. 59.9 (2011): 4637-4643.

Van Moerkercke et al. "The Basic Helix-Loop-Helix Transcription Factor Bis2 Is Essential for Monoterpenoid Indole Alkaloid Production in the Medicinal Plant Catharanthus Roseus" The Plant Journal. 88.1 (2016): 3-12.

Payne et al. GL3 Encodes a bHLH Protein That Regulates Trichome Development in *Arabidopsis* Through Interaction with GL1 and TTG1. Molecular Cell and Developmental Biology and the Institute for Cellular and Molecular Biology. The Gentics Society of America. (2000) 1349-1632.

Van der Fits et al. ORCA3, a Jasmonate-Responsive Transcriptional Regulator of Plant Primary and Secondary Metabolism. Science, vol. 289, Jul. 14, 2000. 295-297. www.sciencemag.org.

* cited by examiner

MEANS AND METHODS FOR REGULATING SECONDARY METABOLITE PRODUCTION IN PLANTS

CROSS-REFERENCE TO RELATED APPLICATIONS

This application is a national phase entry under 35 U.S.C. § 371 of International Patent Application PCT/EP2015/053407, filed Feb. 18, 2015, designating the United States of America and published in English as International Patent Publication WO 2015/124620 A1 on Aug. 27, 2015, which claims the benefit under Article 8 of the Patent Cooperation Treaty to European Patent Application Serial No. 14184392.0, filed Sep. 11, 2014, and to European Patent Application Serial No. 14155634.0, filed Feb. 18, 2014.

TECHNICAL FIELD

This disclosure relates to biology and agriculture and the field of secondary metabolite production in plants. More specifically, this disclosure relates to chimeric genes and their use in the regulation of biosynthesis and/or production of secondary metabolites in plants and plant-derived cell cultures.

STATEMENT ACCORDING TO 37 C.F.R. § 1.821(C) OR (E)—SEQUENCE LISTING SUBMITTED AS A TXT FILE

Pursuant to 37 C.F.R. § 1.821(c) or (e), files containing a TXT version of the Sequence Listing have been submitted concomitant with this application, the contents of which are hereby incorporated by reference.

BACKGROUND

The plant kingdom produces tens of thousands of different small compounds with very complex structures that are often genus or family specific. These molecules, referred to as "secondary metabolites" or "specialized metabolites," display an immense variety in structures and biological activities that plants have tapped into over the course of evolution, and that is now harnessed by man for industrial and medical applications. These compounds play, for example, a role in the resistance against pests and diseases, attraction of pollinators and interaction with symbiotic microorganisms. Besides the importance for the plant itself, secondary metabolites are of great interest because they determine the quality of food (color, taste, aroma) and ornamental plants (flower color, fragrance). A number of secondary metabolites isolated from plants are commercially available as fine chemicals, for example, drugs, dyes, flavors, fragrances and even pesticides. In addition, various health-improving effects and disease-preventing activities of secondary metabolites have been discovered. Flavonoids and terpenoids, for example, have health-promoting activities as food ingredients, and several alkaloids have pharmacological activities. To illustrate this further, taxol is a highly substituted, polyoxygenated cyclic diterpenoid characterized by the taxane ring system, which presents an excellent anti-tumoral activity against a range of cancers.

Although about 100,000 plant secondary metabolites are already known, only a small percentage of all plants have been studied to some extent for the presence of secondary metabolites. Interest in such metabolites is growing as, e.g., plant sources of new and useful drugs are discovered. Some of these valuable phytochemicals are quite expensive because they are only produced at extremely low levels in plants. In fact, very little is known about the biosynthesis of secondary metabolites in plants. However, some recently elucidated biosynthetic pathways of secondary metabolites are long and complicated, requiring multiple enzymatic steps to produce the desired end product. Most often, the alternative of producing these secondary metabolites through chemical synthesis is complicated due to a large number of asymmetric carbons and, in most cases, chemical synthesis is not economically feasible.

The cellular and genetic programs that steer the production of secondary metabolites can be launched rapidly when plants perceive particular environmental stimuli. The jasmonate phytohormones (JAs) play a prominent and universal role in mediating these responses as they can induce synthetic pathways of molecules of a wide structural variety, encompassing all major secondary metabolites (Zhao et al. 2005; Pauwels et al. 2009). Essential in the "core JA signaling module" in plants is the F-box protein CORONATINE INSENSITIVE 1 (COI1), which is part of a Skp/Cullin/F-box-type E3 ubiquitin ligase complex ($SCF^{COI1}$), to which it provides substrate specificity. The targets of the $SCF^{COI1}$ complex are the JA ZIM domain (JAZ) family of repressor proteins. JAZ and COI1 proteins directly interact in the presence of the bioactive JA-isoleucine (JA-Ile) conjugate to form a co-receptor complex, which triggers the degradation of the JAZ proteins by the 26S proteasome. The JAZ proteins are further characterized by a conserved C-terminal JAs domain, which is required for the interaction with both COI1 and a broad array of transcription factors (TFs). JA-triggered JAZ degradation releases these TFs, which each modulate expression of specific sets of JA-responsive genes and, thereby, the production of specific sets of secondary metabolites (De Geyter et al. 2012, *Trends Plant Sci.* 17:349-359).

In *Arabidopsis thaliana*, for example, the basic helix-loop-helix (bHLH) factor MYC2 is the best known target of the JAZ proteins. MYC2 has been shown to be both directly and indirectly involved in regulating secondary metabolite induction, more precisely, of phenolic compounds and glucosinolates. The *Catharanthus roseus* MYC2 homologue regulates the expression of the ORCA TFs by direct binding to the "on/off switch" in the promoter of the ORCA3 gene, and thereby controlling expression of several alkaloid biosynthesis genes. In *Nicotiana tabacum*, MYC2 proteins up-regulate the ORCA-related NIC2 locus APETALA2/ETHYLENE Response Factor (AP2/ERF) TFs that regulate nicotine biosynthesis as well as the nicotine biosynthesis enzymes themselves. JAZ proteins also directly interact with and thereby repress other TFs with a well-established role in the synthesis of secondary metabolites, such as the bHLH TFs GLABRA3 (GL3), ENHANCER OF GL3 (EGL3) and TRANSPARENT TESTA8 (TT8), and the R2R3-MYB TF PAP1, which together compose transcriptional activator complexes that control anthocyanin biosynthesis and are conserved in the plant kingdom.

Besides direct JAZ interactors, other TFs with a proven role in JA-mediated elicitation of a specific metabolic pathway exist, such as WRKY-type TFs that regulate sesquiterpene biosynthesis in various plants, but the full picture on how the central module exerts control over evolutionary distant metabolic pathways, leading to natural products of a wide structural variety, is still lacking. Although overexpression of several of these transcription factors could stimulate synthesis of some secondary metabolites, no master switches have been found that can mimic the full JA spectrum, neither quantitatively nor qualitatively, or replace JAs in plant engineering programs. Likewise, for many secondary metabolic pathways, such as of triterpenes, no regulatory TFs have been identified yet.

Therefore, a need exists for novel ways, preferably generic ways, to regulate the production of secondary metabolites in plants and plant-derived cell cultures.

BRIEF SUMMARY

A first aspect relates to a chimeric gene comprising the following operably linked sequences:
 a) one or more control sequences capable of driving expression of a nucleic acid sequence in a plant cell;
 b) a nucleic acid sequence encoding a bHLH25-like polypeptide comprising a bHLH domain; and
 c) optionally, a transcript termination sequence.

In one particular embodiment of the above-described chimeric gene, the nucleic acid sequence of b) is a polynucleotide selected from the group consisting of:
 a) a polynucleotide that encodes a bHLH25-like polypeptide comprising an amino acid sequence as set forth in SEQ ID NO: 13;
 b) a polynucleotide that encodes a bHLH25-like polypeptide comprising an amino acid sequence having at least 70% identity to the amino acid sequence as set forth in SEQ ID NO: 14; and
 c) variants of the polynucleotides according to (a) or (b).

Also envisaged is a vector comprising any of the above-described chimeric genes.

Another aspect relates to a transgenic plant or a cell derived thereof comprising any of the above-described chimeric genes.

Yet another aspect relates to a method for regulating the production of secondary metabolites in a plant or a plant cell, the method comprising modulating expression in a plant or plant cell of a nucleic acid encoding a bHLH25-like polypeptide comprising a bHLH domain. The modulated expression can be effected by introducing and expressing in a plant or plant cell any of the above-described chimeric genes.

In one embodiment of the above-described method, the production of secondary metabolites is increased. In another embodiment of the above-described method, the production of secondary metabolites is decreased.

Also envisaged is a method of producing a plant or a plant cell with a different profile of secondary metabolites relative to a control plant or control plant cell, the method comprising modulating expression in a plant or plant cell of a nucleic acid encoding a bHLH25-like polypeptide comprising a bHLH domain.

In a more particular embodiment of any of the above-described methods, the secondary metabolites are selected from the group consisting of alkaloid compounds, phenylpropanoid compounds, and terpenoid compounds. In a preferred embodiment of any of the above-described methods, the secondary metabolites are saponins. In another preferred embodiment of any of the above-described methods, the secondary metabolites are monoterpenoid indole alkaloids.

DETAILED DESCRIPTION

Figure 1:
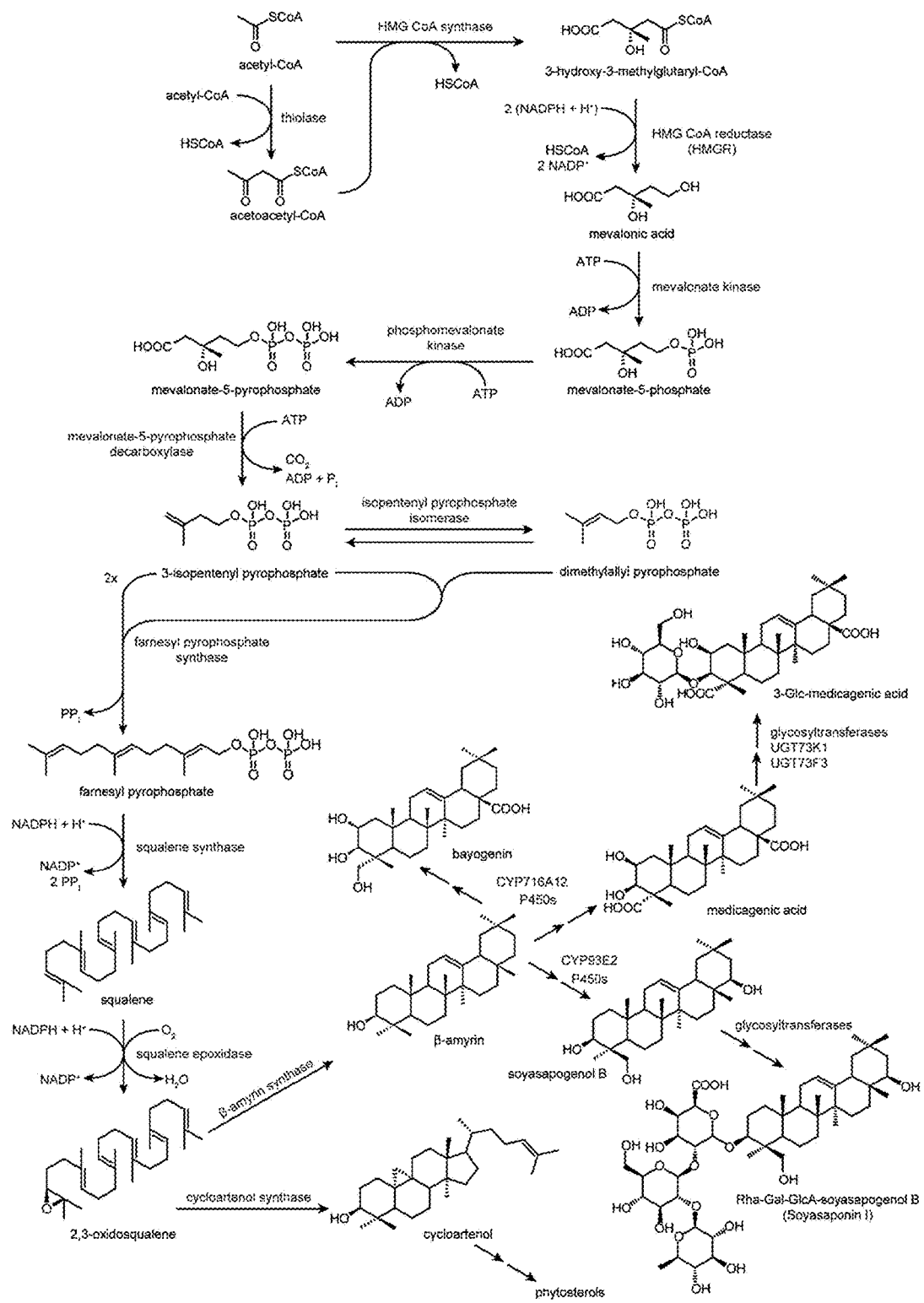
FIG. 1. Saponin biosynthesis in *Medicago truncatula*.
Figure 2A:
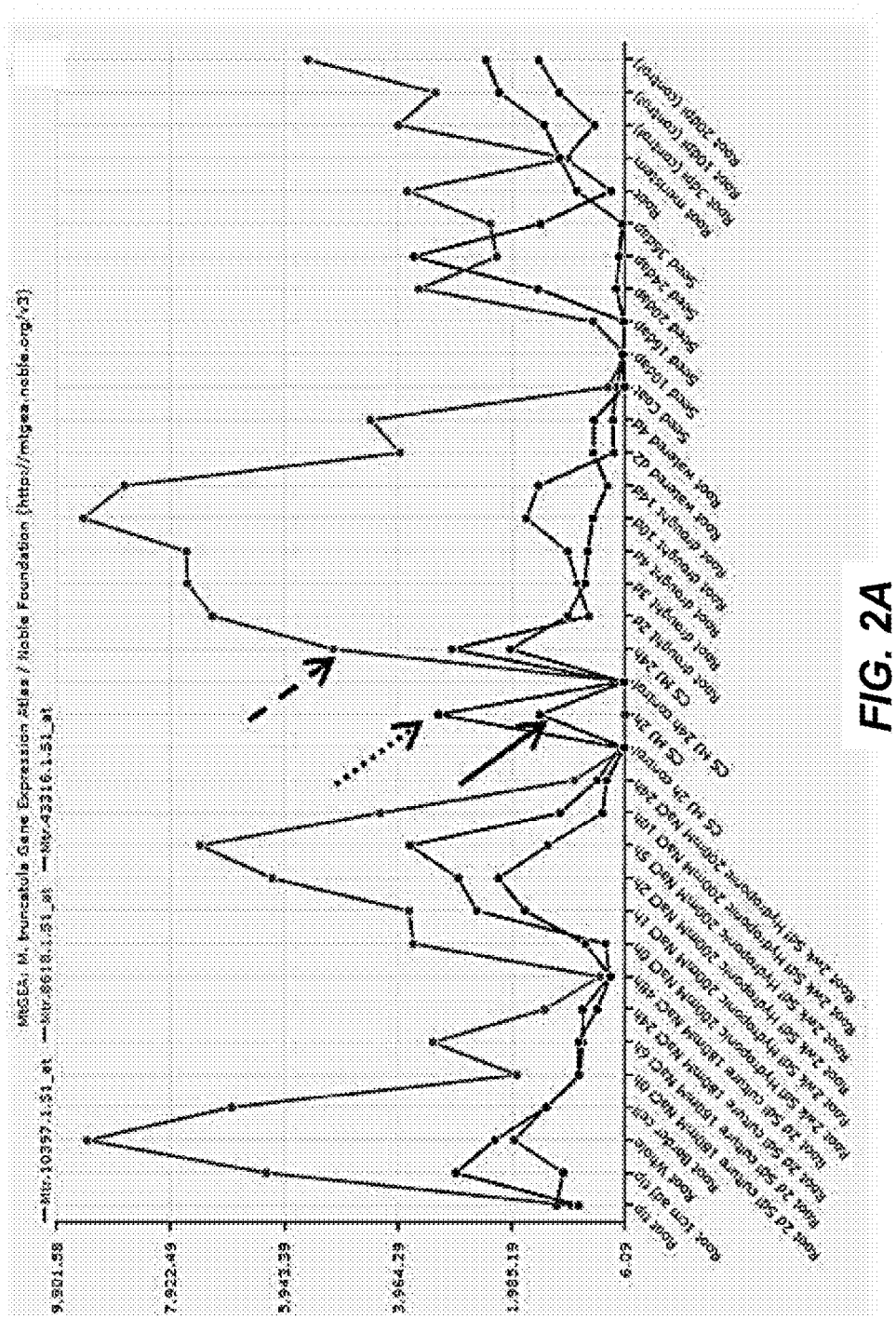
FIGS. 2A-2D. MtbHLH25 factors are co-regulated with triterpene saponin synthesis genes in *M. truncatula*. Co-expression analysis of HMGR1 (dashed arrows), CYP93E2 (dotted arrows), MtbHLH25a (FIG. 2A, full arrow), MtbHLH25b (FIG. 2B, full arrow), MtbHLH25c (FIG. 2C, full arrow), MtbHLH25d (FIG. 2D, full arrow) in various *M. truncatula* plant tissues under various conditions. Note that MtbHLH25a and MtbHLH25c expression levels elevate under influence of methyl jasmonate. MtbHLH25b is only expressed in green seeds at specific stages of development.
Figure 2B:
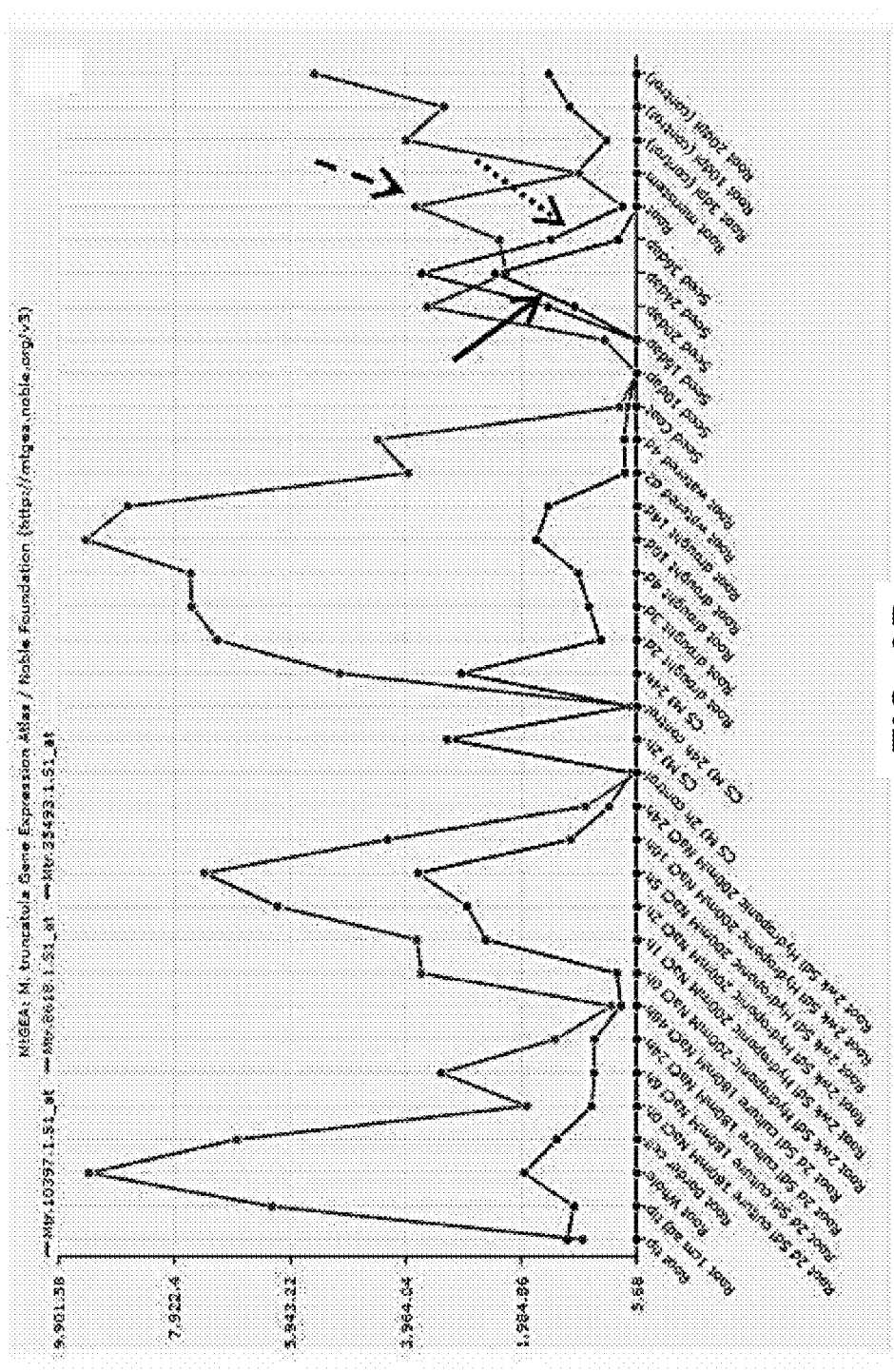
Figure 2C:
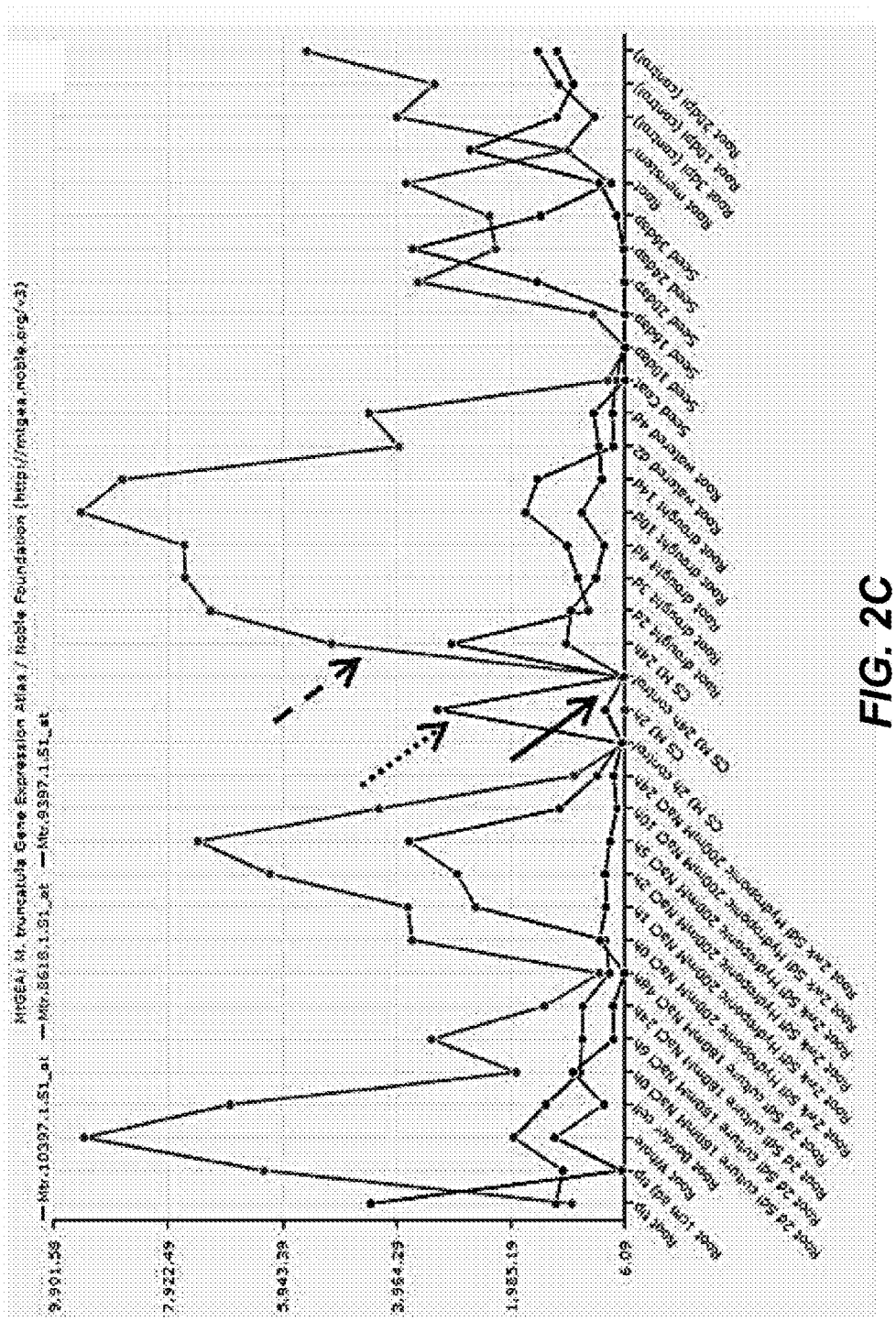
Figure 2D:
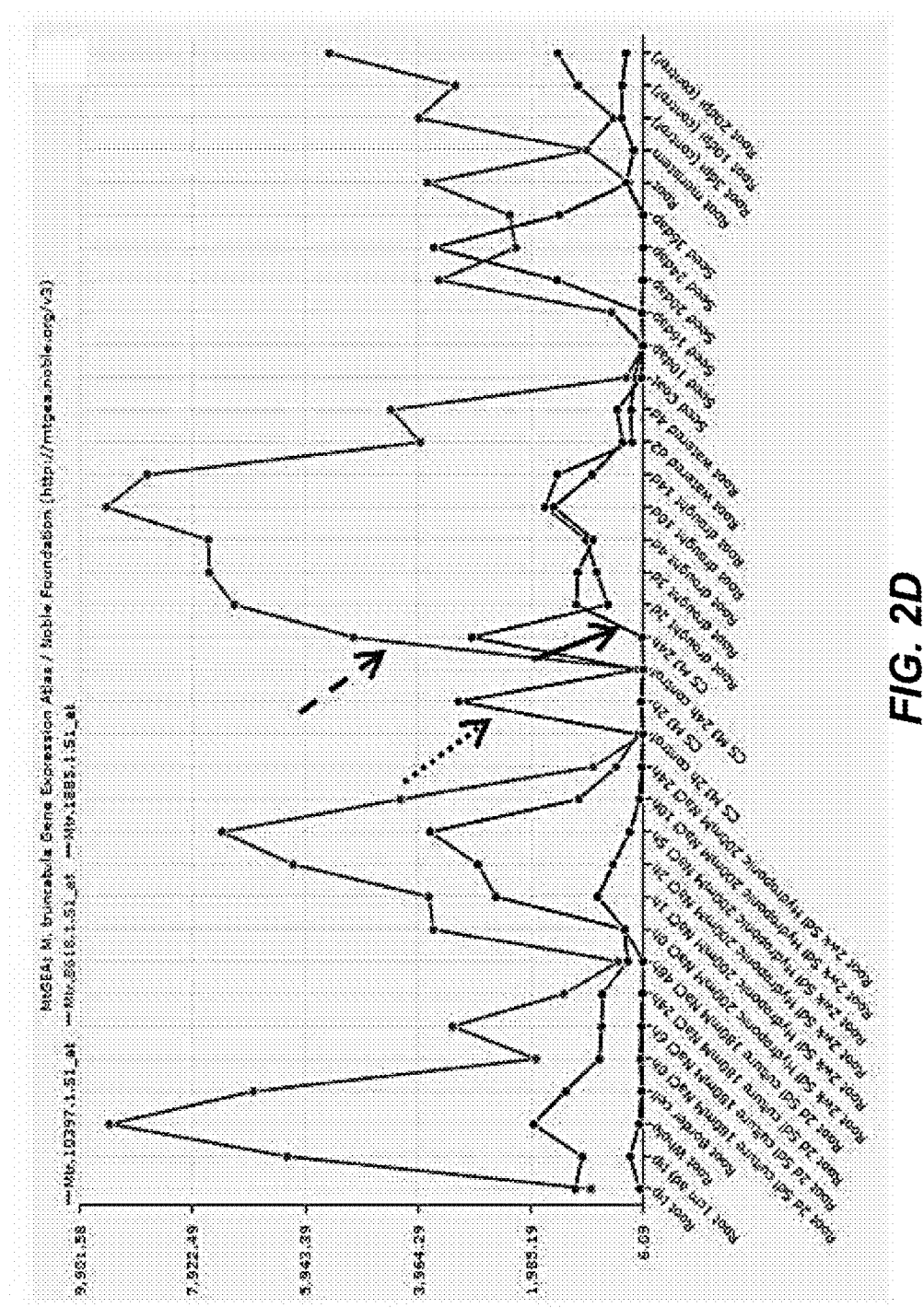

This disclosure provides novel chimeric genes that can be used for the regulation of production of plant-derived secondary metabolites, in particular, to induce or enhance the production and/or secretion of desired secondary metabolites (or intermediates) in plants or cells derived thereof; or otherwise, to repress or decrease the production and/or secretion of undesired secondary metabolites (or intermediates) in plants or cells derived thereof.

Definitions

This disclosure will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn to scale for illustrative purposes. Where the term "comprising" is used in the present description and claims, it does not exclude other elements or steps. Where an indefinite or definite article is used when referring to a singular noun, e.g., "a," "an," or "the," this includes a plural of that noun unless something else is specifically stated. Furthermore, the terms "first," "second," "third," and the like, in the description and in the claims, are used for distinguishing between similar elements and not necessarily for describing a sequential or chronological order. It is to be understood that the terms so used are interchangeable under appropriate circumstances and that the embodiments of the disclosure described herein are capable of operation in other sequences than described or illustrated herein.

Unless otherwise defined herein, scientific and technical terms and phrases used in connection with this disclosure shall have the meanings that are commonly understood by those of ordinary skill in the art. Generally, nomenclatures used in connection with, and techniques of molecular and cellular biology, genetics and protein and nucleic acid chemistry and hybridization described herein are those well known and commonly used in the art. The methods and techniques of this disclosure are generally performed according to conventional methods well known in the art and as described in various general and more specific references that are cited and discussed throughout the present specification unless otherwise indicated. See, for example, Sambrook et al., *Molecular Cloning: A Laboratory Manual*, 2d ed., Cold Spring Harbor Laboratory Press, Cold Spring Harbor, N.Y. (1989); Ausubel et al., *Current Protocols in Molecular Biology*, Greene Publishing Associates (1992, and Supplements to 2002).

As used herein, the terms "polypeptide," "protein," and "peptide" are used interchangeably and refer to a polymeric form of amino acids of any length, which can include coded and non-coded amino acids, chemically or biochemically modified or derivatized amino acids, and polypeptides having modified peptide backbones.

As used herein, the terms "nucleic acid," "polynucleotide," and "polynucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The polynucleotide molecule may be linear or circular. The polynucleotide may comprise a promoter, an intron, an enhancer region, a polyadenylation site, a translation initiation site, 5' or 3' untranslated regions, a reporter gene, a selectable marker or the like. The polynucleotide may comprise single-stranded or double-stranded DNA or RNA. The polynucleotide may comprise modified bases or a modified backbone. A nucleic acid that is up to about 100 nucleotides in length is often also referred to as an oligonucleotide.

Any of the peptides, polypeptides, nucleic acids, etc., disclosed herein may be "isolated" or "purified." "Isolated" is used herein to indicate that the material referred to is (i) separated from one or more substances with which it exists in nature (e.g., is separated from at least some cellular material, separated from other polypeptides, separated from its natural sequence context), and/or (ii) is produced by a process that involves the hand of man such as recombinant DNA technology, chemical synthesis, etc.; and/or (iii) has a sequence, structure, or chemical composition not found in nature. "Purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 90% by weight, e.g., at least 95% by weight, e.g., at least 99% by weight, of the polynucleotide(s) or polypeptide(s) present (but water, buffers, ions, and other small molecules, especially molecules having a molecular weight of less than 1000 Dalton, can be present).

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Determining the percentage of sequence identity can be done manually, or by making use of computer programs that are available in the art. Examples of useful algorithms are PILEUP (Higgins & Sharp, *CABIOS* 5:151 (1989), BLAST® and BLAST® 2.0 (web based sequence alignment tools) (Altschul et al., *J. Mol. Biol.* 215:403 (1990). Software for performing BLAST® analyses is publicly available through the National Center for Biotechnology Information (on the World Wide Web at ncbi.nlm.nih.gov/).

"Similarity" refers to the percentage number of amino acids that are identical or constitute conservative substitutions. Similarity may be determined using sequence comparison programs such as GAP (Deveraux et al. 1984). In this way, sequences of a similar or substantially different length to those cited herein might be compared by insertion of gaps into the alignment, such gaps being determined, for example, by the comparison algorithm used by GAP. As used herein, "conservative substitution" is the substitution of amino acids with other amino acids whose side chains have similar biochemical properties (e.g., are aliphatic, are aromatic, are positively charged, . . . ) and is well known to the skilled person. Non-conservative substitution is then the substitution of amino acids with other amino acids whose side chains do not have similar biochemical properties (e.g., replacement of a hydrophobic with a polar residue). Conservative substitutions will typically yield sequences that are not identical anymore, but still highly similar. By "conservative substitutions" is intended combinations such as gly, ala; val, ile, leu, met; asp, glu; asn, gln; ser, thr; lys, arg; cys, met; and phe, tyr, trp.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived. "Orthologues" and "paralogues" are two different forms of homologues and encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The terms "motif or "consensus sequence" or "signature" refer to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases exist for the identification of domains or motifs, for example, SMART (Schultz et al. (1998), *Proc. Natl. Acad. Sci. USA* 95:5857-5864; Letunic et al. (2002), *Nucleic Acids Res.* 30:242-244), InterPro (Mulder et al. (2003), *Nucl. Acids. Res.* 31:315-318), Prosite (Bucher and Bairoch (1994), A generalized profile syntax for biomolecular sequences motifs and its function in automatic sequence interpretation, in ISMB-94, Proceedings 2nd International Conference on Intelligent Systems for Molecular Biology, R. Altman, D. Brutlag, P. Karp, R. Lathrop, D. Searls, Eds., pp. 53-61, AAA I Press, Menlo Park; Hulo et al., *Nucl. Acids. Res.* 32:D134-D137, (2004)), or Pfam (Bateman et al., *Nucleic Acids Research* 30(1):276-280 (2002)). A set of tools for in silico analysis of protein sequences is available on the ExPASy proteomics server (Swiss Institute of Bioinformatics (Gasteiger et al., ExPASy: the proteomics server for in-depth protein knowledge and analysis, *Nucleic Acids Res.* 31:3784-3788(2003)). Domains or motifs may also be identified using routine techniques, such as by sequence alignment.

Methods for the alignment of sequences for comparison are well known in the art; such methods include GAP, BESTFIT, BLAST® (web based sequence alignment tool), FASTA and TFASTA. GAP uses the algorithm of Needleman and Wunsch ((1970) *J. Mol. Biol.* 48:443-453) to find the global (i.e., spanning the complete sequences) alignment of two sequences that maximizes the number of matches and minimizes the number of gaps. The BLAST® (web based sequence alignment tool) algorithm (Altschul et al. (1990) *J. Mol. Biol.* 215:403-10) calculates percent sequence identity and performs a statistical analysis of the similarity between the two sequences. The software for performing BLAST analysis is publicly available through the National Centre for Biotechnology Information (NCBI). Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., *BMC Bioinformatics*, 2003 Jul. 10, 4:29, MatGAT: an application that generates similarity/identity matrices using protein or DNA sequences). Minor manual editing may be performed to optimize alignment between conserved motifs, as would be apparent to a person skilled in the art. Furthermore, instead of using full-length sequences for the identification of homologues, specific domains may also be used. The sequence identity values may be determined over the entire nucleic acid or amino acid sequence or over selected domains or conserved motif(s), using the programs mentioned above using the default parameters. For local alignments, the Smith-Waterman algorithm is particularly useful (T. F. Smith and M. W. Waterman (1981)*J. Mol. Biol.* 147(1):195-7).

A "deletion" refers to removal of one or more amino acids from a protein.

An "insertion" refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include an activation domain, such as VP16, a (histidine)-6-tag, a glutathione S-transferase-tag, protein A, maltose-binding protein, dihydrofolate reductase, c-myc epitope, FLAG®-epitope, lacZ, CMP (calmodulin-binding peptide), HA epitope, protein C epitope and VSV epitope.

A "substitution" refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids. The amino acid substitutions are preferably conservative amino acid substitutions. Conservative substitution tables are well known in the art; see, for example, Creighton (1984) Proteins, W.H. Freeman and Company (Eds) or Table below.

TABLE 1

| Residue | Conservative Substitutions |
|---|---|
| Ala | Ser |
| Arg | Lys |
| Asn | Gln, His |
| Asp | Glu |
| Gln | Asn |
| Cys | Ser |
| Glu | Asp |
| Gly | Pro |
| His | Asn, Gln |
| Ile | Leu, Val |
| Leu | Ile, Val |
| Lys | Arg, Gln |
| Met | Leu, Ile |
| Phe | Met, Leu, Tyr |
| Ser | Thr, Gly |
| Thr | Ser, Val |
| Trp | Tyr |
| Tyr | Trp, Phe |
| Val | Ile, Leu |

Substitutions that are less conservative than those in Table 1 can be selected by picking residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that, in general, are expected to produce the greatest changes in protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine.

As used herein, the term "derivatives" include peptides, oligopeptides, polypeptides that may, compared to the amino acid sequence of the naturally occurring form of the protein or polypeptide of interest (in this case, the bHLH25-like polypeptide), comprise substitutions of amino acids with non-naturally occurring amino acid residues, or additions of non-naturally occurring amino acid residues. "Derivatives" of a protein also encompass peptides, oligopeptides, polypeptides that comprise naturally occurring altered (glycosylated, acylated, prenylated, phosphorylated, myristoylated, sulphated, etc.) or non-naturally altered amino acid residues compared to the amino acid sequence of a naturally occurring form of the polypeptide. A derivative may also comprise one or more non-amino acid substituents or additions compared to the amino acid sequence from which it is derived, covalently or non-covalently bound to the amino acid sequence, such as a reporter molecule that is bound to facilitate its detection, and non-naturally occurring amino acid residues relative to the amino acid sequence of a naturally occurring protein. Furthermore, "derivatives" also include fusions of the naturally occurring form of the protein with tagging peptides such as FLAG, HIS6 or thioredoxin (for a review of tagging peptides, see Terpe, *Appl. Microbiol. Biotechnol.* 60:523-533, 2003).

The term "chimeric gene" or "chimeric construct," as used herein, is a recombinant nucleic acid sequence wherein one or more control sequences (at least a promoter) are operably linked to, or associated with, a nucleic acid sequence that codes for an mRNA, such that the one or more control sequences are able to regulate transcription or expression of the associated nucleic acid coding sequence. The one or more control sequences of the chimeric gene are not normally operably linked to the associated nucleic acid sequence as found in nature.

The terms "regulatory element," "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and is involved in recognizing and binding of RNA polymerase and other proteins, thereby directing transcription of an operably linked nucleic acid. Encompassed by the aforementioned terms are transcriptional regulatory sequences derived from a classical eukaryotic genomic gene (including the TATA box, which is required for accurate transcription initiation, with or without a CCAAT box sequence) and additional regulatory elements (i.e., upstream activating sequences, enhancers and silencers), which alter gene expression in response to developmental and/or external stimuli, or in a tissue-specific manner. Also included within the term is a transcriptional regulatory sequence of a classical prokaryotic gene, in which case, it may include a 35-box sequence and/or a 10-box transcriptional regulatory sequence. The term "regulatory element" also encompasses a synthetic fusion molecule or derivative that confers, activates or enhances expression of a nucleic acid molecule in a cell, tissue or organ.

The term "operably linked" as used herein refers to a linkage in which the regulatory sequence is contiguous with the gene of interest to control the gene of interest, as well as regulatory sequences that act in trans or at a distance to control the gene of interest. For example, a DNA sequence is operably linked to a promoter when it is ligated to the promoter downstream with respect to the transcription initiation site of the promoter and allows transcription elongation to proceed through the DNA sequence. A DNA for a signal sequence is operably linked to DNA coding for a polypeptide if it is expressed as a pre-protein that participates in the transport of the polypeptide. Linkage of DNA sequences to regulatory sequences is typically accomplished by ligation at suitable restriction sites or adapters or linkers inserted in lieu thereof using restriction endonucleases known to one of skill in the art.

The term "expression" or "gene expression" means the transcription of a specific gene or specific genes or specific genetic construct. The term "expression" or "gene expression," in particular, means the transcription of a gene or genes or genetic construct into structural RNA (rRNA, tRNA) or mRNA with or without subsequent translation of the latter into a protein. The process includes transcription of DNA and processing of the resulting mRNA product.

The term "vector" as used herein is intended to refer to a nucleic acid molecule capable of transporting another nucleic acid molecule to which it has been linked. The vector may be of any suitable type including, but not limited to, a phage, virus, plasmid, phagemid, cosmid, bacmid or even an artificial chromosome. Certain vectors are capable of autonomous replication in a host cell into which they are introduced (e.g., vectors having an origin of replication that functions in the host cell). Other vectors can be integrated into the genome of a host cell upon introduction into the host cell, and are thereby replicated along with the host genome. Moreover, certain preferred vectors are capable of directing the expression of certain genes of interest. Such vectors are referred to herein as "recombinant expression vectors" (or simply, "expression vectors"). Suitable vectors have regulatory sequences, such as promoters, enhancers, terminator sequences, and the like, as desired and according to a particular host organism (e.g., plant cell). Typically, a recombinant vector according to this disclosure comprises at least one "chimeric gene" or "expression cassette," as defined hereinbefore.

Description

This disclosure shows that modulating expression in a plant or cells derived thereof of a nucleic acid encoding a protein of the family of bHLH transcription factors can be used to alter the production of secondary metabolites relative to control plants.

According to a first aspect, the disclosure relates to a chimeric gene, or otherwise expression cassette, comprising the following operably linked sequences: a) one or more control sequences capable of driving expression of a nucleic acid sequence in a plant or plant cell; b) a nucleic acid sequence encoding a bHLH protein comprising a bHLH domain, more specifically encoding a bHLH25-like polypeptide comprising a bHLH domain; and c) optionally, a transcript termination sequence.

The "basic helix-loop-helix (bHLH) proteins" are a superfamily of transcription factors that bind as dimers to specific DNA target sites. The family is defined by the presence of a bHLH domain (as defined further herein), which contains a highly conserved amino acid motif. Outside of the conserved bHLH domain, the proteins exhibit considerable sequence divergence. As used herein, the term "basic helix-loop-helix (bHLH) domain" refers to a highly conserved amino acid motif that defines the group of transcription factors that are known as bHLH proteins. The bHLH domain is well defined in the art and consists of about 60 amino acids that form two functionally distinct segments: a stretch of about 15 predominantly basic amino acids (the basic region) and a section of around 40 amino acids predicted to form two amphipathic α-helices separated by a loop of variable length (the helix-loop-helix region). The basic region forms the main interface where contact with DNA occurs, whereas the two helices promote the formation of homo- or heterodimers between bHLH proteins, a prerequisite for DNA binding to occur. bHLH proteins are found throughout eukaryotic organisms.

Within the scope of this disclosure, a bHLH protein particularly refers to a plant-derived bHLH protein. Plant-derived bHLH proteins are well known in the art (see, e.g., Pires and Dolan 2010, *Mol. Biol. Evol.* 27:862-874; Toledo-Ortiz et al. 2003, *Plant Cell* 15:1749-1770; and Heim et al. 2003, Mol. Biol. Evol. 20:735-747). Today, plant-derived bHLH proteins are classified into different subfamilies and reference is particularly made to Table 1 on pages 870 to 871 in Pires and Dolan, 2010, Mol. Biol. Evol. 27:862-874, which is incorporated herein by reference. According to a preferred embodiment, the bHLH protein of this disclosure belongs to subfamily IVa.

Examples of plant-derived bHLH nucleotide sequences and encoded proteins belonging to the subfamily IVa include bHLH25 nucleotide sequences of *Medicago truncatula*, MtbHLH25a (SEQ ID NO: 1), MtbHLH25b (SEQ ID NO: 2), MtbHLH25c (SEQ ID NO: 3), MtbHLH25d (SEQ ID NO: 4), and the MtbHLH25 polypeptides encoded thereby, MtbHLH25a (SEQ ID NO: 5), MtbHLH25b (SEQ ID NO: 6), MtbHLH25c (SEQ ID NO: 7), MtbHLH25d (SEQ ID NO: 8). Other representative members of subfamily IVa bHLH proteins include homologues of the *Medicago truncatula* bHLH25 polypeptides. For example, the *Medicago truncatula* bHLH25 polypeptides share homology with a number of bHLH25-like polypeptides that phylogenetically belong to the same subfamily, for example, bHLH25-like polypeptides from *Arabidopsis thaliana* AtbHLH020 (At2g22770), AtbHLH019 (At2g22760), AtbHLH018 (At2g22750), AtbHLH025 (At4g37850), from *Oryza sativa* OsbHLH021 (Os12g43620), OsbHLH022 (Os03g46790), OsbHLH020 (Os03g46860), OsbHLH023 (Os10g01530), OsbHLH018 (Os03g51580). Other examples of homologous sequences of the *Medicago* bHLH25 sequences from other plant species can be found via BLAST® (web based sequence alignment tool) searches on public databases such as NCBI (on the internet at blast.ncbi.nlm.nih.gov/), PLAZA (on the internet at bioinformatics.psb.ugent.be/plaza/blast/index) or ORCAE (on the internet at bioinformatics.psb.ugent.be/orcae/) and include, but are not limited to, the homologues from the medicinal plant *Catharanthus roseus* Caros001862 (CrbHLH25; SEQ ID NO: 15), Caros006385 (CrbHLH18; SEQ ID NO: 16), and Caros017587.

Thus, a "bHLH25-like polypeptide" as used herein collectively refers to a bHLH protein of subfamily IVa. Typically, a bHLH25-like polypeptide has a conserved bHLH domain. Non-limiting examples of bHLH domains as comprised in bHLH25-like polypeptides include bHLH domains defined by SEQ ID NOs: 9-12. Also, a bHLH25-like polypeptide has a bHLH domain comprising an amino acid sequence having at least 50% overall sequence identity and, for instance, at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% to the amino acid represented by SEQ ID NO: 9.

In particular, the bHLH25-like polypeptides as used herein comprise a bHLH domain comprising at least the following conserved amino acid motif:

(SEQ ID NO: 13)
$X_1HX_2X_3AERX_4RRX_5X_6LX_7X_8X_9X_{10}X_{11}ALX_{12}AX_{13}X_{14}PX_{15}LX_{16}KX_{17}DK$ wherein $X_1$ can be D or E; wherein $X_2$ can be I or V or L; wherein $X_3$ can be L or M or V or I; wherein $X_4$ can be K or R or N; wherein $X_5$ can be R or Q or E; wherein $X_6$ can be any amino acid, preferably K or Q or E or D; wherein $X_7$ can be T or S; wherein $X_8$ can be E or Q; wherein $X_9$ can be R or S or K or N; wherein $X_{10}$ can be F or I or L; wherein $X_{11}$ can be I or V or M; wherein $X_{12}$ can be S or A; wherein $X_{13}$ can be any amino acid, preferably I or V or L or T; wherein $X_{14}$ can be V or I or L or P; wherein $X_{15}$ can be G or N; wherein $X_{16}$ can be K or N or S or R; and wherein $X_{17}$ can be any amino acid, preferably M or T. It will be understood that amino acid residues for each $X_1$ to $X_{17}$ represent alternatives.

For example, a consensus motif characteristic for the group of bHLH25-like polypeptides can be defined by the following amino acid sequence:

```
                                     (SEQ ID NO: 14)
DHIMAERKRREKLTQRFIALSALIPGLKKMDK
```

Also envisaged are motifs with amino acid sequences having at least 70% overall sequence identity and, for instance, at least 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% to the amino acid represented by SEQ ID NO: 14.

Other representative examples of motifs comprised in bHLH25-like polypeptides are defined by the following amino acid sequences, as retrieved from PLAZA:

```
TC01G007250
                                     (SEQ ID NO: 48)
DHIMAERKRREKLSQRFIALSAIVPGLKKMDK

FV0G20600
                                     (SEQ ID NO: 49)
DHIMAERKRREKLSQRFIALSAIVPGLKKMDK

MD02G000440
                                     (SEQ ID NO: 50)
DHIMAERKRREKLSQRFIALSAIXPGLKKMDK

CP00129G00360
                                     (SEQ ID NO: 51)
DHIVAERKRREKLSQRFIALSAIVPGLKKMDK

ZM01G51370
                                     (SEQ ID NO: 52)
DHILAERKRREKLSQRFIALSKIVPGLKKMDK

OS03G51580
                                     (SEQ ID NO: 53)
EHILAERKRREKLSQRFIALSKIVPGLKKMDK

ME09335G00010
                                     (SEQ ID NO: 54)
DHILAERKRREKLSQRFIALSAIVPGLKKMDK

AT2G22770
                                     (SEQ ID NO: 55)
EHVLAERKRRQKLNERLIALSALLPGLKKTDK

AT2G22760
                                     (SEQ ID NO: 56)
EHVLAERKRREKLSEKFIALSALLPGLKKADK

MD02G000420
                                     (SEQ ID NO: 57)
DHVLAERKRREKLSQRFIALSALLPGLKKMDK

FV0G20580
                                     (SEQ ID NO: 58)
DHVLAERKRREKLSQRFIALSALVPGLKKMDK

ME02883G00050
                                     (SEQ ID NO: 59)
DHVLAERKRREKLSQRFISLSAVVPGLKKMDK

RC28179G00220
                                     (SEQ ID NO: 60)
DHILAERKRREKLSQRFIALSALVPGLKKMDK

PT09G08310
                                     (SEQ ID NO: 61)
DHIIAERKRREKLSQRFIALSAVVPGLKKMDK

Caros001862
                                     (SEQ ID NO: 62)
DHIIAERKRREQLSQHFVALSAIVPGLKKMDK Caros006385
                                     (SEQ ID NO: 63)
DHIIAERKRREILSQRFMALSTLVPGLKKMDK AT4G37850
                                     (SEQ ID NO: 64)
DHIIAERKRREKLTQRFVALSALVPGLKKMDK MD00G205570
                                     (SEQ ID NO: 65)
DHIIAERKRREKLTQRFVALSALVPGLKKMDK AT2G22750
                                     (SEQ ID NO: 66)
DHILAERKRREKLTQRFVALSALIPGLKKMDK VV07G03050
                                     (SEQ ID NO: 67)
DHVIAERKRRGKLTQRFIALSALVPGLRKMDK VV00G09620
                                     (SEQ ID NO: 68)
DHVVAERKRREKLTQRFIALSALVPGLRKTDK Medtr4g066460
                                     (SEQ ID NO: 69)
DHIMAERNRREKLTQSFIALAALVPNLKKMDK Medtr0246s0020
                                     (SEQ ID NO: 70)
DHIMAERKRREKLSQSFIALAALVPNLKKMDK GM17G16720
                                     (SEQ ID NO: 71)
DHIMAERKRREKLSQSFIALAALVPGLKKMDK GM05G23530
                                     (SEQ ID NO: 72)
DHIMAERKRREKLSQSFIALAALVPGLKKMDK GM11G04680
                                     (SEQ ID NO: 73)
DHIIAERKRREKLSQSLIALAALIPGLKKMDR GM01G40620
                                     (SEQ ID NO: 74)
DHIIAERKRREKLSQSLIALAALIPGLKKMDK LJ2G026110
                                     (SEQ ID NO: 75)
DHIIAERRRREKLSQSLIALAALIPGLKKMDK GM07G03060
                                     (SEQ ID NO: 76)
DHIMAERRRRQELTERFIALSATIPGLNKTDK GM08G23050
                                     (SEQ ID NO: 77)
DHIMAERRRRQDLTERFIALSATIPGLSKTDK GM03G25100
                                     (SEQ ID NO: 78)
DHIMAERKRRQDLTERFIALSATIPGLKKTDK GM07G13500
                                     (SEQ ID NO: 79)
NHIMAERKRRELTERFIALSATIPGLKKTDK GM07G03050
                                     (SEQ ID NO: 80)
DHIMTERKRRELTERFIALSATIPGLKKIDK
```

-continued

Medtr7g080780
(SEQ ID NO: 81)
DHLMAERKRRRELTENIIALSAMIPGLKKMDK

Medtr2g104650
(SEQ ID NO: 82)
DHIMSERNRRQLLTSKIIELSALIPGLKKIDK

GM15G00730
(SEQ ID NO: 83)
SHIMAERKRRQQLTQSFIALSATIPGLNKKDK

Thus, in one embodiment, the invention provides a chimeric gene as described above, wherein the nucleic acid sequence of b) is a polynucleotide selected from the group consisting of:
 a. a polynucleotide that encodes a bHLH25-like polypeptide comprising an amino acid sequence as set forth in SEQ ID NO: 13;
 b. a polynucleotide that encodes a bHLH25-like polypeptide comprising an amino acid sequence having at least 70% identity to the amino acid sequence as set forth in SEQ ID NO: 14; and
 c. variants of the polynucleotides according to (a) or (b).

A "variant" as used herein refers to homologs, orthologs and paralogs and include, but are not limited to, homologs, orthologs and paralogs of polynucleotides encoding a bHLH25-like polypeptide. Non-limiting examples include homologs, orthologs and paralogs of SEQ ID NOs: 1-4. Homologs of a protein encompass peptides, oligopeptides and polypeptides having amino acid substitutions, deletions and/or insertions, preferably by a conservative change, relative to the unmodified protein in question and having similar biological and functional activity as the unmodified protein from which they are derived; or, in other words, without significant loss of function or activity. Orthologs and paralogs, which are well-known terms by the skilled person, define subcategories of homologs and encompass evolutionary concepts used to describe the ancestral relationships of genes. Paralogs are genes within the same species that have originated through duplication of an ancestral gene; orthologs are genes from different organisms that have originated through speciation, and are also derived from a common ancestral gene. Several different methods are known by those of skill in the art for identifying and defining these functionally homologous sequences. General methods for identifying orthologues and paralogues include phylogenetic methods, sequence similarity and hybridization methods. Percentage similarity and identity can be determined electronically. Examples of useful algorithms are PILEUP (Higgins & Sharp, *CABIOS* 5:151 (1989), BLAST® and BLAST® 2.0 (Altschul et al., *J. Mol. Biol.* 215:403 (1990). Software for performing BLAST® analyses is publicly available through the National Center for Biotechnology Information (on the internet at ncbi.nlm.nih.gov). Preferably, the homologue, orthologue or paralogue has a sequence identity at a protein level of at least 50%, preferably 60%, more preferably 70%, even more preferably 80%, most preferably 90% as measured in a BLASTp®. For example, non-limiting examples of functionally homologous sequences include bHLH25-like polypeptides from *Arabidopsis thaliana* AtbHLH020 (At2g22770), AtbHLH019 (At2g22760), AtbHLH018 (At2g22750), AtbHLH025 (At4g37850), from *Oryza sativa* OsbHLH021 (Os12g43620), OsbHLH022 (Os03g46790), OsbHLH020 (Os03g46860), OsbHLH023 (Os10g01530), OsbHLH018 (Os03g51580), amongst others.

In a particular embodiment, derivatives (as defined herein) of any of the above encoded polypeptides also from part of this disclosure.

According to one specific embodiment, the chimeric gene of the disclosure is not a chimeric gene that comprises the following operably linked sequences: a) CaMV 35S promoter; b) a nucleic acid sequence encoding Atg22770; and c) nopaline synthase terminator.

Further, it will be appreciated by those of skill in the art, that any of a variety of polynucleotide sequences are capable of encoding the polypeptides of this disclosure. Due to the degeneracy of the genetic code, many different polynucleotides can encode identical and/or substantially similar polypeptides. Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, e.g., site-directed mutagenesis, available in the art. Accordingly, any and all such variations of a sequence are a feature of the disclosure. In addition to silent variations, other conservative variations that alter one or a few amino acids in the encoded polypeptide, can be made without altering the function of the polypeptide (i.e., regulating secondary metabolite production, in the context of this disclosure), these conservative variants are, likewise, a feature of the disclosure.

Conservative substitutions or variations, as used herein, are those in which at least one residue in the amino acid sequence has been removed and a different residue inserted in its place and are defined hereinbefore. Deletions and insertions introduced into the sequences are also envisioned by the disclosure. Such sequence modifications can be engineered into a sequence by site-directed mutagenesis or the other methods known in the art. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, e.g., a deletion of two residues or insertion of two residues. Substitutions, deletions, insertions or any combination thereof can be combined to arrive at a sequence. The mutations that are made in the polynucleotides of the disclosure should not create complementary regions that could produce secondary mRNA structure. Preferably, the polypeptide encoded by the DNA performs the desired function (i.e., enhanced secondary metabolite production, in the context of this disclosure).

Further, the disclosure also envisages a vector comprising any of the above-described chimeric genes.

According to yet another aspect, the disclosure provides a transgenic plant or a cell derived thereof that is transformed with any of the above-described constructs.

The term "plant" as used herein refers to vascular plants (e.g., gymnosperms and angiosperms). A "transgenic plant" refers to a plant comprising a recombinant polynucleotide and/or a recombinant polypeptide according to the disclosure. A transgenic plant refers to a whole plant as well as to a plant part, such as seed, fruit, leaf, or root, plant tissue, plant cells or any other plant material, and progeny thereof. A transgenic plant can be obtained by transforming a plant cell with an expression cassette of this disclosure and regenerating such plant cell into a transgenic plant. Such plants can be propagated vegetatively or reproductively. The transforming step may be carried out by any suitable means, including by *Agrobacterium*-mediated transformation and non-*Agrobacterium*-mediated transformation, as discussed in detail below. Plants can be regenerated from the transformed cell (or cells) by techniques known to those skilled in the art. Where chimeric plants are produced by the process, plants in which all cells are transformed may be regenerated from chimeric plants having transformed germ cells, as is known in the art. Methods that can be used to transform plant cells or tissue with expression vectors of this disclosure include both *Agrobacterium* and non-*Agrobacterium* vectors. *Agrobacterium*-mediated gene transfer exploits the natural ability of *Agrobacterium tumefaciens* to transfer DNA into plant chromosomes and is described in detail in G. Gheysen, G. Angenon, and M. Van Montagu (1998), *Agrobacterium*-mediated plant transformation: a scientifically intriguing story with significant applications, in K. Lindsey (Ed.), *Transgenic Plant Research* Harwood Academic Publishers, Amsterdam, pp. 1-33; and in H. A. Stafford (2000), *Botanical Review* 66:99-118. A second group of transformation methods is the non-*Agrobacterium*-mediated transformation and these methods are known as direct gene transfer methods. An overview is included by P. Barcelo and P. A. Lazzeri (1998), Direct gene transfer: chemical, electrical and physical methods in K. Lindsey (Ed.), *Transgenic Plant Research*, Harwood Academic Publishers, Amsterdam, pp. 35-55.

Methods include particle gun delivery, microinjection, electroporation of intact cells, polyethyleneglycol-mediated protoplast transformation, electroporation of protoplasts, liposome-mediated transformation, silicon-whiskers mediated-transformation, etc.

Hairy root cultures can be obtained by transformation with virulent strains of *Agrobacterium rhizogenes*, and they can produce high contents of secondary metabolites characteristic to the mother plant. Protocols used for establishing of hairy root cultures vary, as well as the susceptibility of plant species to infection by *Agrobacterium* (Toivounen et al. 1993, *Biotechnol. Prog.* 9:12; Vanhala et al. 1995, *Plant Cell Rep.* 14:236). It is known that the *Agrobacterium* strain used for transformation has a great influence on root morphology and the degree of secondary metabolite accumulation in hairy root cultures. It is possible by systematic clone selection, e.g., via protoplasts, to find high yielding, stable, and single-cell-derived hairy root clones. This is possible because the hairy root cultures possess a great somaclonal variation. Another possibility of transformation is the use of viral vectors (Turpen 1999, *Philos. Trans. R. Soc. Lond. B. Biol. Sci.* 354:665-73.).

Any plant tissue or plant cells capable of subsequent clonal propagation, whether by organogenesis or embryogenesis, may be transformed with a construct of this disclosure. The term "organogenesis" means a process by which shoots and roots are developed sequentially from meristematic centers. The term "embryogenesis" means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include protoplasts, leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyls meristem).

A "control plant" as used in this disclosure refers to a plant cell, seed, plant component, plant tissue, plant organ or whole plant used to compare against transgenic or genetically modified plants for the purpose of identifying a difference in production of secondary metabolite (as described further herein) in the transgenic or genetically modified plant. A control plant may in some cases be a transgenic plant line that comprises an empty vector or marker gene, but does not contain the recombinant polynucleotide of this disclosure that is expressed in the transgenic or genetically modified plant being evaluated. In general, a control plant is a plant of the same line or variety as the transgenic or genetically modified plant being tested. A suitable control plant would include a genetically unaltered or non-transgenic plant of the parental line (wild-type) used to generate a transgenic plant herein.

Plants of this disclosure may include, but not limited to, plants or plant cells of agronomically important crops that are or are not intended for animal or human nutrition, such as maize or corn, wheat, barley, oat, *Brassica* spp. plants such as *Brassica napus* or *Brassica juncea*, soybean, bean, alfalfa, pea, rice, sugarcane, beetroot, tobacco, sunflower, quinoa, cotton, *Arabidopsis*, vegetable plants such as cucumber, leek, carrot, tomato, lettuce, peppers, melon, watermelon, diverse herbs such as oregano, basilicum and mint. It may also be applied to plants that produce valuable compounds, e.g., useful as, for instance, pharmaceuticals, as ajmalicine, vinblastine, vincristine, ajmaline, reserpine, rescinnamine, camptothecine, ellipticine, quinine, and quinidine, taxol, morphine, scopolamine, atropine, cocaine, sanguinarine, codeine, genistein, daidzein, digoxin, calystegins or as food additives such as anthocyanins, vanillin, including, but not limited to, the classes of compounds mentioned above. Examples of such plants include, but not limited to, *Papaver* spp., *Rauwolfia* spp., *Catharanthus* spp., *Artemisia* spp., *Taxus* spp., *Cinchona* spp., *Eschscholtzia californica*, *Camptotheca acuminata*, *Hyoscyamus* spp., *Berberis* spp., *Coptis* spp., *Datura* spp., *Atropa* spp., *Thalictrum* spp., *Peganum* spp., *Panax* spp., *Avena* spp., *Medicago* spp., *Quillaja* spp., *Sapindus* spp., *Saponaria* spp., *Betula* spp., *Digitalis* spp., *Glycyrrhiza* spp., *Bupleurum* spp., *Centella* spp., *Dracaena* spp., *Aesculus* spp., *Yucca* spp., amongst others.

The chimeric genes as described above may be expressed in, for example, a plant cell under the control of a promoter that directs constitutive expression or regulated expression. Regulated expression comprises temporally or spatially regulated expression and any other form of inducible or repressible expression. "Temporally" means that the expression is induced at a certain time point, for instance, when a certain growth rate of the plant cell culture is obtained (e.g., the promoter is induced only in the stationary phase or at a certain stage of development). "Spatially" means that the promoter is only active in specific organs, tissues, or cells (e.g., only in roots, leaves, epidermis, guard cells or the like). Other examples of regulated expression comprise promoters whose activity is induced or repressed by adding chemical or physical stimuli to the plant cell. In a preferred embodiment, the expression is under control of environmental, hormonal, chemical, and/or developmental signals. Such promoters for plant cells include promoters that are regulated by (1) heat, (2) light, (3) hormones, such as abscisic acid and methyl jasmonate, (4) wounding or (5) chemicals such as salicylic acid, chitosans or metals. Indeed, it is well known that the expression of secondary metabolites can be boosted by the addition of, for example, specific chemicals, jasmonate and elicitors. In a particular embodiment, the co-expression of several (more than one) polynucleotide sequences, in combination with the induction of secondary metabolite synthesis, is beneficial for an optimal and enhanced production of secondary metabolites. Alternatively, the at least one polynucleotide sequence is placed under the control of a constitutive promoter. A constitutive promoter directs expression in a wide range of cells under a wide range of conditions. Examples of constitutive plant promoters useful for expressing heterologous polypeptides in plant cells include, but are not limited to, the cauliflower mosaic virus (CaMV) 35S promoter, which confers constitutive, high-level expression in most plant tissues including monocots, the nopaline synthase promoter and the octopine synthase promoter. The expression cassette is usually provided in a DNA or RNA construct, which is typically called an "expression vector," which is any genetic element, e.g., a plasmid, a chromosome, a virus, behaving either as an autonomous unit of polynucleotide replication within a cell (i.e., capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, bacteriophages, cosmids, plant viruses and artificial chromosomes. The expression cassette may be provided in a DNA construct, which also has at least one replication system. In addition to the replication system, there will frequently be at least one marker present, which may be useful in one or more hosts, or different markers for individual hosts. The markers may a) code for protection against a biocide, such as antibiotics, toxins, heavy metals, certain sugars or the like; b) provide complementation, by imparting prototrophy to an auxotrophic host; or c) provide a visible phenotype through the production of a novel compound in the plant. Exemplary genes that may be employed include neomycin phosphotransferase (NPTII), hygromycin phosphotransferase (HPT), chloramphenicol acetyltransferase (CAT), nitrilase, and the gentamicin resistance gene. For plant host selection, non-limiting examples of suitable markers are β-glucuronidase, providing indigo production, luciferase, providing visible light production, Green Fluorescent Protein and variants thereof, NPTII, providing kanamycin resistance or G418 resistance, HPT, providing hygromycin resistance, and the mutated aroA gene, providing glyphosate resistance.

The term "promoter activity" refers to the extent of transcription of a polynucleotide sequence that is operably linked to the promoter whose promoter activity is being measured. The promoter activity may be measured directly by measuring the amount of RNA transcript produced, for example, by Northern blot or indirectly by measuring the product coded for by the RNA transcript, such as when a reporter gene is linked to the promoter.

According to a further aspect of the disclosure, the above-described chimeric genes can be used for modulating the production of secondary metabolites in plants and plant-derived cell cultures. According to a preferred embodiment, this disclosure provides methods for modulating the production of secondary metabolites chosen from the group comprising alkaloid compounds, phenylpropanoid compounds and terpenoid compounds, for which non-limiting examples are provided further herein. In one particular embodiment, this disclosure provides methods for modulating the production of at least one secondary metabolite, which is meant to include related structures of secondary metabolites and intermediates or precursors thereof.

Generally, two basic types of metabolites are synthesized in cells, i.e., those referred to as primary metabolites and those referred to as secondary metabolites (also referred to as specialized metabolites). A primary metabolite is any intermediate in, or product of the primary metabolism in cells. The primary metabolism in cells is the sum of metabolic activities that are common to most, if not all, living cells and are necessary for basal growth and maintenance of the cells. Primary metabolism thus includes pathways for generally modifying and synthesizing certain carbohydrates, amino acids, fats and nucleic acids, with the compounds involved in the pathways being designated primary metabolites. In contrast hereto, secondary metabolites usually do not appear to participate directly in growth and development.

Secondary plant metabolites, as used herein, include, e.g., alkaloid compounds (e.g., terpenoid indole alkaloid, tropane alkaloids, steroidal alkaloids), phenylpropanoid compounds (e.g., quinines, lignans and flavonoids), terpenoid compounds (e.g., monoterpenoids, iridoids, sesquiterpenoids, diterpenoids and triterpenoids). In addition, secondary metabolites include small molecules, such as substituted heterocyclic compounds, which may be monocyclic or polycyclic, fused or bridged. Many plant secondary metabolites have value as pharmaceuticals. Non-limiting examples of plant pharmaceuticals include, e.g., taxol, digoxin, atropine, scopolamine, colchicine, diosgenin, codeine, cocaine, morphine, quinine, shikonin, ajmaline, vinblastine, vincristine, and others.

As used herein, the definition of "alkaloids," of which more than 15,000 structures have been described already, refers to all nitrogen-containing natural products that are not otherwise classified as amino acid peptides and proteins, amines, cyanogenic glycosides, glucosinolates, antibiotics, phytohormones or primary metabolites (such as purine and pyrimidine bases). Alkaloids can be divided into the following major groups: (i) "true alkaloids," which contain nitrogen in the heterocycle and originate from amino acids, for which atropine, nicotine and morphine are characteristic examples; (ii) "protoalkaloids," which contain nitrogen in the side chain and also originate from amino acids, for which mescaline, adrenaline and ephedrine are characteristic examples; (iii) "polyamine alkaloids," which are derivatives of putrescine, spermidine and spermine; (iv) "peptide and cyclopeptide alkaloids"; (v) "pseudoalkaloids," which are alkaloid-like compounds that do not originate from amino acids, including terpene-like and steroid-like alkaloids as well as purine-like alkaloids such as caffeine, theobromine and thephylline.

Plants synthesize alkaloids for various defense-related reactions, e.g., actions against pathogens or herbivores. Enzymes and genes have been partly characterized only in groups of nicotine and tropane alkaloids, indole alkaloids and isoquinolidine alkaloids (Suzuki et al. 1999, *Plant Mol. Biol.* 40:P141).

As used herein, "phenylpropanoids" or "phenylpropanes," refer to aromatic compounds with a propyl side-chain attached to the aromatic ring, which can be derived directly from phenylalanine. The ring often carries oxygenated substituents (hydroxyl, methoxy and methylenedioxy groups) in the para-position. Natural products in which the side-chain has been shortened or removed can also be derived from typical phenylpropanes. Phenylpropanoids are found throughout the plant kingdom. Most plant phenolics are derived from the phenylpropanoid and phenylpropanoid-acetate pathways and fulfil a very broad range of physiological roles in plants. For example, polymeric lignins reinforce specialized cell wall. Closely related are the lignans that vary from dimers to higher oligomers. Lignans can either help defend against various pathogens or act as antioxidants in flowers, leaves and roots. The flavonoids comprise an astonishingly diverse group of more than 4500 known compounds. Among their subclasses are the anthocyanins (pigments), proanthocyanidins or condensed tannins (feeding deterrents and wood protectants), and isoflavonoids (defensive products and signaling molecules). The coumarins, furanocoumarins, and stilbenes protect against bacterial and fungal pathogens, discourage herbivory, and inhibit seed germination.

As used herein, "terpenoids" or otherwise "isoprenoids" refer to the large and diverse class of naturally occurring organic chemicals of terpenes and can be found in all classes of living organisms. Terpenoids are molecules derived from a five-carbon isoprene unit that are assembled and modified in different ways and have diverse activities. Plant terpenoids are used extensively for their aromatic qualities and contribute to, e.g., the scent of eucalyptus, the flavors of cinnamon, clover and ginger, and the color of yellow flowers. They play a role in traditional herbal remedies and may have antibacterial, antineoplastic, and other pharmaceutical functions. Well-known terpenoids include citral, menthol, camphor, salvinorin A and cannabinoids and are also used to flavor and/or scent a variety of commercial products. The steroids and sterols in animals are biologically produced from terpenoid precursors. They also include pharmaceuticals, e.g., taxol, artemisinin, vinblastine and vincristine.

Terpenoids are classified with reference to the number of isoprene units that comprise the particular terpenoid. For example, a monoterpenoid comprises two isoprene units; a sesquiterpenoid comprises three isoprene units; and a diterpenoid comprises four isoprene units. Polyterpenoids comprise multiple isoprene units. There are many thousands of examples of terpenoids. Artemisinin is a sesquiterpene lactone endoperoxide and is a natural product produced by the plant *Artemisia annua*. Artemisinin is typically used in combination with anti-malarial therapeutics, for example, lumefantrine, mefloquine, amodiaquine, sulfadoxine, chloroquine, in artemisinin combination therapies (ACT). Endoperoxides like artemisinin, for example, dihydroartemisinin, artemether, and sodium artesunate have been used in the treatment of malaria. Examples of monoterpenoids include linalool, citronellol, menthol, geraniol and terpineol. Linalool and citronellol are used as a scent in soap, detergents, shampoo and lotions. Linalool is also an intermediate in the synthesis of vitamin E. Menthol is isolated from peppermint or other mint oils and is known for its anesthetic properties; it is often included in sore throat medications and oral medications, e.g., for the treatment of bad breath in toothpaste and mouth wash. Geraniol is known for its insect repellent properties and is also used as a scent in perfumes. Terpineol is also used as an ingredient in perfumes and cosmetics and as flavoring. It is apparent that in addition to the pharmaceutical applications of monoterpenoids such as perillyl alcohol, there are additional uses as scents, flavorings, and as insect deterrents.

The synthesis of terpenoids involves a large number of enzymes with different activities. For example, isoprene units are synthesized from monosaturated isoprene units by prenyltransferases into multiples of 2, 3 or 4 isoprene units. These molecules serve as substrates for terpene synthase enzymes, also called terpene cyclase. Plant terpene synthases are known in the art.

A particular class of terpenoids are the saponins. The term "saponins" as used herein are a group of bio-active compounds that consist of an isoprenoidal aglycone, designated "genin" or "sapogenin," covalently linked to one or more sugar moieties. This combination of polar and non-polar structural elements in their molecules explains their soap-like behavior in aqueous solutions. Most known saponins are plant-derived secondary metabolites, though several saponins are also found in marine animals such as sea cucumbers and starfish. In plants, saponins are generally considered to be part of defense systems due to antimicrobial, fungicidal, allelopathic, insecticidal and moluscicidal, etc., activities. Typically, saponins reside inside the vacuoles of plant cells. Extensive reviews on molecular activities, biosynthesis, evolution, classification, and occurrence of saponins are given by, e.g., Augustin et al. 2011, *Phytochemistry* 72:435-57, and Vincken et al. 2007, *Phytochemistry* 68:275-97. Thus, the term "sapogenin," as used herein, refers to an aglycone, or non-saccharide, moiety of the family of natural products known as saponins.

The commonly used nomenclature for saponins distinguishes between triterpenoid saponins (also: triterpene saponins) and steroidal saponins, which is based on the structure and biochemical background of their aglycones. Both sapogenin types are thought to derive from 2,3-oxidosqualene, a central metabolite in sterol biosynthesis. In phytosterol anabolism, 2,3-oxidosqualene is mainly cyclized into cycloartenol. Triterpenoid sapogenins branch off the phytosterol pathway by alternative cyclization of 2,3-oxidosqualene, while steroidal sapogenins are thought to derive from intermediates in the phytosterol pathway downstream of cycloartenol formation (see also FIG. 1). A more detailed classification of saponins based on sapogenin structure with 11 main classes and 16 subclasses has been proposed by Vincken et al. 2007, *Phytochemistry* 68:275-97; particularly from page 276 to page 283, and also FIGS. 1 and 2), which is all incorporated herein by reference. In particular, saponins may be selected from the group comprising dammarane-type saponins, tirucallane-type saponins, lupane-type saponins, oleanane-type saponins, taraxasterane-type saponins, ursane-type saponins, hopane-type saponins, cucurbitane-type saponins, cycloartane-type saponins, lanostane-type saponins, and steroid-type saponins. The aglycon backbones, the sapogenins, can be similarly classified and may be selected from the group comprising dammarane-type sapogenins, tirucallane-type sapogenins, lupane-type sapogenins, oleanane-type sapogenins, taraxasterane-type sapogenins, ursane-type sapogenins, hopane-type sapogenins, cucurbitane-type sapogenins, cycloartane-type sapogenins, lanostane-type sapogenins, and steroid-type sapogenins. A well-known example of triterpenoid saponins includes ginsenoside found in ginseng. A well-known example of steroid saponins, also referred to as glycoalkaloids, includes solanine found in potato and tomato.

Triterpenoid sapogenins typically have a tetracyclic or pentacyclic skeleton. As described in the Background section, the sapogenin building blocks themselves may have multiple modifications, e.g., small functional groups, including hydroxyl, keto, aldehyde, and carboxyl moieties, of precursor sapogenin backbones such as β-amyrin, lupeol, and dammarenediol.

The terms "triterpene" and "triterpenoid" are used interchangeably herein.

It is to be understood that the secondary plant metabolites, as used herein, also encompass new-to-nature compounds that are structurally related to the naturally occurring metabolites. These new-to-nature compounds may be currently unextractable compounds by making use of existing extraction procedures or may be novel compounds that can be obtained after genetic engineering of the synthesizing plant or plant cell culture (see further herein).

With "production" of secondary metabolites is meant both intracellular production as well as secretion into the medium. The term "modulates" or "modulation" in relation to production of secondary metabolites refers to an increase or a decrease in production or biosynthesis of secondary metabolites.

Often, an increase of a secondary metabolite is desired but sometimes a decrease of a secondary metabolite is wanted. That decrease can, for example, refer to the decrease of an undesired intermediate product or a toxic end product. With an increase in the production of one or more metabolites, it is understood that the production may be enhanced by at least 20%, 30%, 40%, 50%, 60%, 70%, 80%, 90% or at least 100% relative to a control plant (or plant cell). Conversely, a decrease in the production of the level of a secondary metabolite may be decreased by at least 20%, 30%, 40%, 50%, 60%, 70%, 80%, 90% or at least 100% relative to a control plant (or plant cell).

An "induced production" of a secondary metabolite means that there is no detectable production of secondary metabolite(s) by the control (untransformed) plant (cell) but that detection becomes possible upon carrying out the transformation according to the disclosure.

An "enhanced production" of a secondary metabolite means that there already exists a detectable amount of secondary metabolite(s) by the control (untransformed) plant cell but that detection becomes possible upon carrying out the transformation according to the disclosure and that an increase of secondary metabolite(s) can be measured by at least 20%, 30%, 40%, 50%, 60%, 70%, 80%, 90% or more than 90% compared to basal secretion by the control (untransformed) plant (cell).

Preferably, the organism (such as a plant or plant cell line) transformed with a polynucleotide of this disclosure is induced before it produces secondary metabolites. The wording "inducing the production" means that, for example, the cell or tissue culture, such as a plant cell or tissue culture, is stimulated by the addition of an external factor. External factors include the application of heat, the application of cold, the addition of acids, bases, metal ions, fungal membrane proteins, sugars and the like. One approach that has been given interesting results for better production of plant secondary metabolites is elicitation. Elicitors are compounds capable of inducing defense responses in plants. These are usually not found in intact plants but their biosynthesis is induced after wounding or stress conditions. Commonly used elicitors are jasmonates, mainly jasmonic acid and its methyl ester, methyl jasmonate (MeJA). Jasmonates are linoleic acid derivatives of the plasma membrane and display a wide distribution in the plant kingdom. They were originally classified as growth inhibitors or promoters of senescence, but now it has become apparent that they have pleiotropic effects on plant growth and development. Jasmonates appear to regulate cell division, cell elongation and cell expansion and thereby stimulate organ or tissue formation. They are also involved in the signal transduction cascades that are activated by stress situations such as wounding, osmotic stress, desiccation and pathogen attack. MeJA is known to induce the accumulation of numerous defense-related secondary metabolites (e.g., phenolics, alkaloids, triterpenoids and sesquiterpenoids) through the induction of genes coding for the enzymes involved in the biosynthesis of these compounds in plants. Jasmonates can modulate gene expression from the (post)transcriptional to the (post)translational level, both in a positive way and a negative way. Genes that are up-regulated are, e.g., defense- and stress-related genes (PR proteins and enzymes involved with the synthesis of phytoalexins and other secondary metabolites, whereas the activity of housekeeping proteins and genes involved with photosynthetic carbon assimilation are down-regulated. For example, the biosynthesis of phytoalexins and other secondary products in plants can also be boosted up by signal molecules derived from micro-organisms or plants (such as peptides, oligosaccharides, glycopeptides, salicylic acid and lipophilic substances) as well as by various abiotic elicitors like UV-light, heavy metals (Cu, VOSO4, Cd) and ethylene. The effect of any elicitor is dependent on a number of factors, such as the specificity of an elicitor, elicitor concentration, the duration of the treatment and growth stage of the culture.

Generally, secondary metabolites can be measured intracellularly or in the extracellular space by methods known in the art. Such methods comprise analysis by thin-layer chromatography, high-pressure liquid chromatography, capillary electrophoresis, gas chromatography combined with mass spectrometric detection, radioimmuno-assay (RIA) and enzyme immuno-assay (ELISA). For example, taxol and taxanes can be measured as described in Ketchum et al. 2007, *Plant Cell Rep.* 26:1025-1033; tobacco alkaloid content can be analyzed by GC-MS (Millet et al. 2009, *J. Pharm. Biomed. Anal.* 49:1166-1171); *Medicago* flavonoid and triterpene saponin content can be analyzed by reverse-phase UPLC/ICR/FT-MS (see also Example section).

When the chimeric genes of this disclosure are used to modulate the production of secondary metabolites in plants or plant cells, the disclosure can be practiced with any plant variety for which cells of the plant can be transformed with an expression cassette of the current disclosure and for which transformed cells can be cultured in vitro. Suspension culture, callus culture, hairy root culture, shoot culture or other conventional plant cell culture methods may be used (as described in: *Drugs of Natural Origin*, G. Samuelsson, 1999, ISBN 9186274813). By "plant cells," it is understood to mean any cell that is derived from a plant and can be subsequently propagated as callus, plant cells in suspension, organized tissue and organs (e.g., hairy roots). Tissue cultures derived from the plant tissue of interest can be established. Methods for establishing and maintaining plant tissue cultures are well known in the art (see, e.g., R. N. Trigiano and D. J. Gray (1999), "Plant Tissue Culture Concepts and Laboratory Exercises," *ISBN:* 0-8493-2029-1; E. B. Herman (2000), "Regeneration and Micropropagation: Techniques, Systems and Media 1997-1999," *Agricell Report*). Typically, the plant material is surface-sterilized prior to introducing it to the culture medium. Any conventional sterilization technique, such as chlorinated bleach treatment, can be used. In addition, antimicrobial agents may be included in the growth medium. Under appropriate conditions, plant tissue cells form callus tissue, which may be grown either as solid tissue on solidified medium or as a cell suspension in a liquid medium.

A number of suitable culture media for callus induction and subsequent growth on aqueous or solidified media are known. Exemplary media include standard growth media, many of which are commercially available (e.g., Sigma Chemical Co., St. Louis, Mo.). Examples include Schenk-Hildebrandt (SH) medium, Linsmaier-Skoog (LS) medium, Murashige and Skoog (MS) medium, Gamborg's B5 medium, Nitsch & Nitsch medium, White's medium, and other variations and supplements well known to those of skill in the art (see, e.g., *Plant Cell Culture*, Dixon, ed. IRL Press, Ltd. Oxford (1985), and George et al., *Plant Culture Media*, Vol 1, Formulations and Uses Exegetics Ltd. Wilts, UK, (1987)). For the growth of conifer cells, particularly suitable media include ½ MS, ½ L.P., DCR, Woody Plant Medium (WPM), Gamborg's B5 and its modifications, DV (Durzan and Ventimiglia, in *Vitro Cell Dev. Biol.* 30:219-227 (1994)), SH, and White's medium.

In yet another aspect, the disclosure envisages a method for regulating the production of secondary metabolites in a plant or a plant cell relative to a control plant or control plant cell, the method comprising modulating expression in a plant or plant cell of a nucleic acid encoding a bHLH25-like polypeptide, wherein the bHLH25-like polypeptide comprises a bHLH domain. In specific embodiments, modulating can be increasing or decreasing the expression of a nucleic acid encoding a bHLH25-like polypeptide.

The term "modulation" means, in relation to expression or gene expression, a process in which the expression level is changed by the gene expression in comparison to the control plant, wherein the expression level may be increased or decreased. The original, unmodulated expression may be of any kind of expression of a structural RNA (rRNA, tRNA) or mRNA with subsequent translation. For the purposes of this disclosure, the original unmodulated expression may also be absence of any expression. The term "modulating the activity" shall mean any change of the expression of the nucleic acid sequences or encoded proteins, which leads to increased production of secondary metabolites by the plants. The expression can increase from zero (absence of, or immeasurable expression) to a certain amount, or can decrease from a certain amount to immeasurably small amounts or zero.

The term "increased expression" or "overexpression" as used herein means any form of expression that is additional to the original wild-type expression level. For the purposes of this disclosure, the original wild-type expression level might also be zero, i.e., absence of expression or immeasurable expression. Methods for increasing expression of genes or gene products are well documented in the art and include, for example, overexpression driven by appropriate promoters, the use of transcription enhancers or translation enhancers, which are described hereinbefore.

Reference herein to "decreased expression" or "reduction or substantial elimination" of expression is taken to mean a decrease in endogenous gene expression and/or polypeptide levels and/or polypeptide activity relative to control plants. The reduction or substantial elimination is in increasing order of preference, at least 10%, 20%, 30%, 40% or 50%, 60%, 70%, 80%, 85%, 90%, or 95%, 96%, 97%, 98%, 99% or more reduced compared to that of control plants. Methods for decreasing expression of genes or gene products are well documented in the art and include, for example, RNA-mediated silencing of gene expression (down-regulation). Gene silencing may also be achieved by insertion mutagenesis (for example, T-DNA insertion or transposon insertion) or by strategies as described by, among others, Angell and Baulcombe ((1999) *Plant J.* 20(3):357-62), (Amplicon VIGS WO 98/36083), or Baulcombe (WO 99/15682). Further, artificial and/or natural microRNAs (miRNAs) may be used to knock out gene expression and/or mRNA translation.

According to a preferred embodiment, the modulated expression is effected by introducing and expressing in a plant or plant cell a chimeric gene of the disclosure that comprises a nucleic acid encoding a bHLH25-like polypeptide, as described hereinbefore.

Further, this disclosure also relates to a method for the production or for stimulating the biosynthesis of secondary metabolites in a plant or a plant cell comprising the steps of transforming the plant or plant cell with a chimeric gene of this disclosure and allowing the plant or the plant cell to grow.

In a particular embodiment, the disclosure herein can be combined with other known methods to enhance the production and/or the secretion of secondary metabolites in plant cell cultures such as (1) by improvement of the plant cell culture conditions, (2) by the transformation of the plant cells with a transcription factor capable of up-regulating genes involved in the pathway of secondary metabolite formation, (3) by the addition of specific elicitors to the plant cell culture, and 4) by the induction of organogenesis, amongst other methods.

The chimeric genes of this disclosure can be used in all types of plants to boost the plant's own secondary metabolite production or in plants that are transformed with a combination of genetic material that can lead to the generation of novel metabolic pathways (for example, through the interaction with metabolic pathways resident in the host organism or, alternatively, silent metabolic pathways can be unmasked) and eventually lead to the production of novel classes of compounds. This novel or reconstituted metabolic pathway can have utility in the commercial production of novel, valuable compounds.

The following examples are intended to promote a further understanding of this disclosure. While this disclosure is described herein with reference to illustrated embodiments, it should be understood that the disclosure is not limited hereto. Those having ordinary skill in the art and access to the teachings herein will recognize additional modifications and embodiments within the scope thereof. Therefore, this disclosure is limited only by the claims attached herein.

EXAMPLES

Example 1: Selection of Novel Transcription Factors that are Co-Regulated with Known Saponin Biosynthesis Genes in *Medicago truncatula*

To identify new regulators of saponin biosynthesis, co-expression analyses of 3-hydroxy-3-methylglutaryl coenzyme A reductase 1 (HMGR1) and the cytochrome P450 monooxygenase CYP93E2 were performed using the *Medicago truncatula* Gene Expression Atlas (MtGEA) Web Server (Benedito et al. 2008, *Plant J.* 55:504-513). The HMGR1 enzyme catalyzes the rate-limiting step in the biosynthesis of isopentenyl pyrophosphate (IPP), the precursor of all triterpenes. The CYP93E2 enzyme hydroxylates C-24 on the β-amyrin backbone, which is the first specific step for the biosynthesis of the soyasaponins (for an overview of saponin biosynthesis in *M. truncatula*, see FIG. 1). Co-expression was checked in various tissues, with a main focus on the roots as production site for saponins. Four transcription factors TFs, all belonging to clade IVa of the basic helix-loop-helix (bHLH) family of TFs to which also *Arabidopsis thaliana* bHLH25 (At4g37850) belongs (Heim et al., 2003, *Mol. Biol. Evol.* 20:735-747), were significantly co-expressed (FIG. 2). The complete open reading frames (ORFs) were obtained by blasting the Affymetrix probe set sequences against the *M. truncatula* genome v4.0 (*Medicago truncatula* genome project) and were denominated as follows: MtbHLH25a (Medtr7g080780.1), MtbHLH25b (Medtr2g104650.1), MtbHLH25c (Medtr4g066460.1) and MtbHLH25d (Medtr0246s0020.1) (Table 2).

Example 2: Chimeric Constructs of *M. truncatula* bHLH25 Homologues for Functional Analyses Complete ORFs of MtbHLH25a, b, c and d were PCR-amplified with primer sets P1+P2, P3+P4, P5+P6 and P7+P8, respectively (Table 3). As a template for MtbHLH25b, cDNA made from RNA extracted from green *M. truncatula* seeds was used. For the other three genes, cDNA made from RNA from *M. truncatula* hairy root material that was treated with methyl jasmonate was utilized. Subsequently, all MtbHLH25 genes were cloned into the entry vector pDONR221 using the GATEWAY® recombination system (Invitrogen Life Technologies).

The capacity of the MtbHLH25 factors to transactivate promoters of saponin biosynthesis genes was assessed in an automated transient expression assay in *Nicotiana tabacum* (tobacco) BY-2 protoplasts (see Example 3) (De Sutter et al. 2005, *Plant J.* 44:1065-1076). Therefore, the MtbHLH25 ORFs were transferred from the entry clones into the p2GW7 high copy vector in which the genes are subjected to regulation by the cauliflower mosaic virus (CaMV) 35S promotor (Karimi et al. 2002, *Trends Plant Sci.* 5:193-195). Promoter sequences of *M. truncatula* genes involved in saponin biosynthesis were constituted by selecting the first 1000 base pairs upstream of the corresponding ORFs, which were identified in the *M. trunctatula* genome v 3.5. This was done for HMGR1, β-amyrin synthase (BAS), cytochrome P450 monooxygenase CYP93E2 and two UDP-dependent glycosyl transferases (i.e., UGT73F3 and UGT73K) (Table 2). The promoter sequences were PCR-amplified using the following primer sets, respectively: P9+P10, P11+P12, P13+P14, P15+P16, P17+P18 (Table 3). All PCR fragments were recombined into the GATEWAY® entry vector pDONR221 (Invitrogen Life Technologies) from which they were transferred into the pGWL7 destination vector (De Sutter et al. 2005, *Plant J.* 44:1065-1076). Hence, these reporter constructs consist of a fusion of the promoter with the firefly luciferase ORF (fLUC).

In order to over-express the MtbHLH25 factors in *M. truncatula* hairy roots as described (Pollier et al., 2011, *J. Nat. Prod.* 74:1462-1476) (see Examples 4 and 5), the ORFs were inserted in the pK7WGD2 destination vector, in which they become expressed from a 35S promoter (Karimi et al. 2002, *Trends Plant Sci.* 5:193-195). This plasmid was then transformed into the *Agrobacterium rhizogenes* strain LBA 9402/12 to transfect *M. truncatula* hairy roots (ecotype Jemalong J5).

Figure 3:
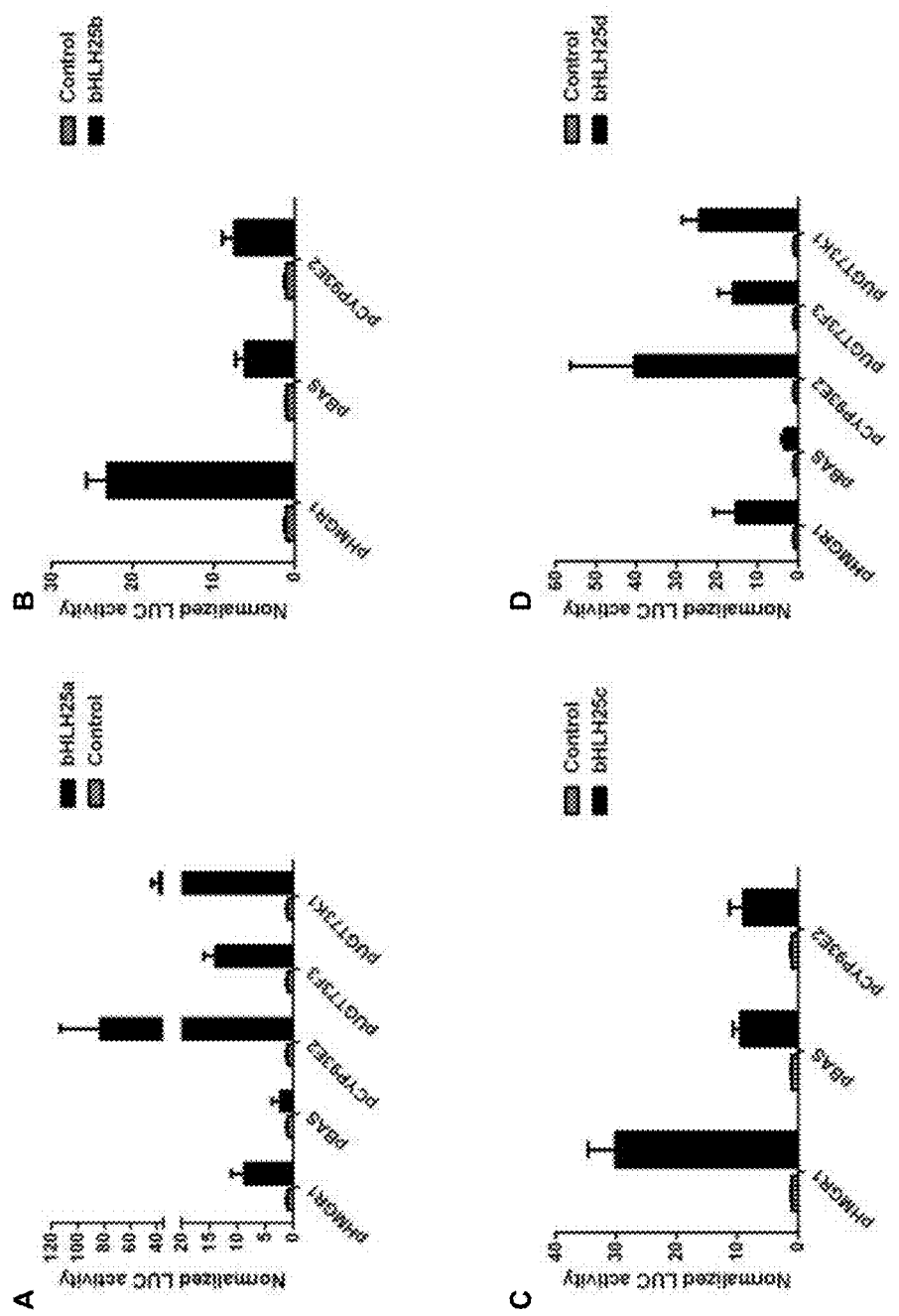
FIG. 3. MtbHLH25 transcription factors activate promoters of saponin biosynthesis genes in BY-2 protoplast transient expression assays. All activation values (fLUC/fREN) were normalized by dividing with the average control values, hence are expressed relative to the normalized control. Standard errors are designated by error bars (n=8 for panels A, C and D; n=24 for panel B).

Example 3: Functional Analysis of MtbHLH25 Homologues by Transient Expression Assays BY-2 tobacco protoplasts were transfected as described by De Sutter et al. 2005, *Plant J.* 44:1065-1076. A dual firefly/Renilla luciferase assay was carried out in which the fLUC readout is a measure for the promoter activation level and fREN a measure for transfection efficiency. As control, a non-functional β-glucuronidase (GUS) gene expressed from the 35S promoter was used. It was observed that MtbHLH25a mediates a strong activation of the saponin biosynthesis gene promoters pHMGR1, pCYP93E2, pUGT73F3 and pUGT73K15 (FIG. 3). The other MtbHLH25s mediate activation of the same promoters, but with various strengths. For pBAS, a minor activation was observed with all MtbHLH25 factors.

Example 4: Overexpression of MtbHLH25 Homologues in Transgenic *M. truncatula* Hairy Roots Transgenic *M. truncatula* hairy roots were generated as described (Pollier et al. 2011, J. Nat. Prod. 74:1462-1476) and grown for 10 days in 5 mL Murashige and Skoog basal salt mixture including vitamins (Duchefa) medium supplied with 1% sucrose. Successively, 20 mL medium was added after which the roots were incubated for an additional 2 weeks. The hairy roots were harvested, rinsed with water and ground in liquid nitrogen into a fine powder. 10 mg of root material was used for RNA extraction and cDNA generation.

Figure 4:
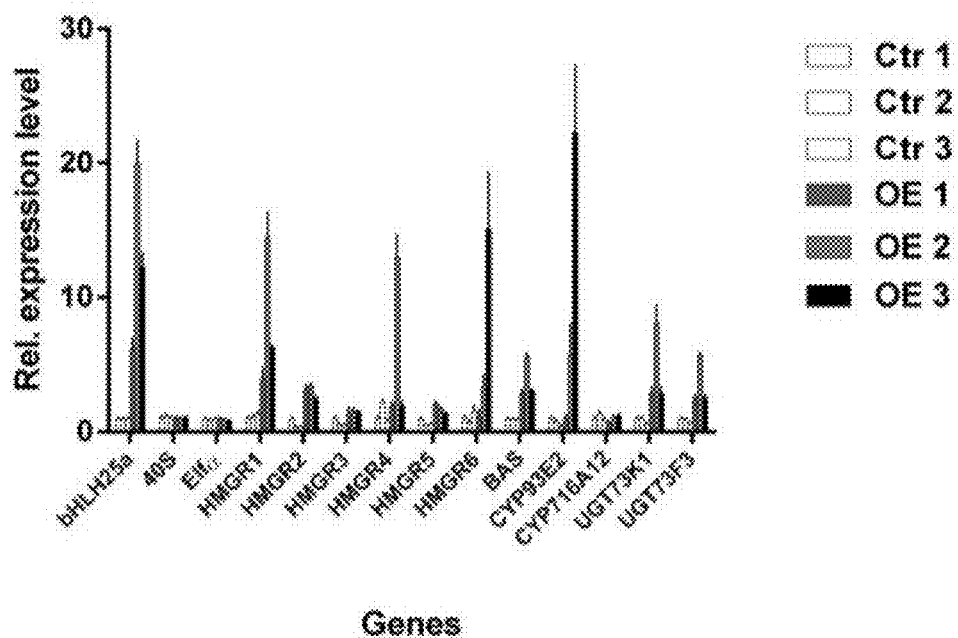
FIG. 4. Quantitative PCR analysis of saponin genes in control (CTR) and MtbHLH25a overexpressing (OE) *M. truncatula* hairy root lines. Ctr lines Ctr 1, Ctr 2 and Ctr 3 are represented in consecutive order by white bars; MtbHLH25a OE lines OE 1, OE 2 and OE 3 are depicted by bars with different shades of gray. The Y-axis represents fold increase relative to control line 1 (CTR1). Standard errors are designated by error bars (n=3).

Three MtbHLH25a OE lines and three control (CTR, i.e., overexpressing GUS from a 35S promoter) lines were analyzed by quantitative PCR (qPCR) to assess the transcript levels of saponin biosynthesis genes. Primers were designed with Beacon Designer. As reference genes, a 40S ribosomal protein S8 (40S) and translation elongation factor 1α (ELF1 α) were used. Overexpression of MtbHLH25a was shown to up-regulate a variety of saponin biosynthesis genes, including HMGR1, HMGR2, HMGR4, HMGR6, BAS, CYP93E2, UGT73F3 and UGT73K1 (FIG. 4).

Example 5: Enhanced Production of Saponins in MtbHLH25a OE Lines

Figure 5:
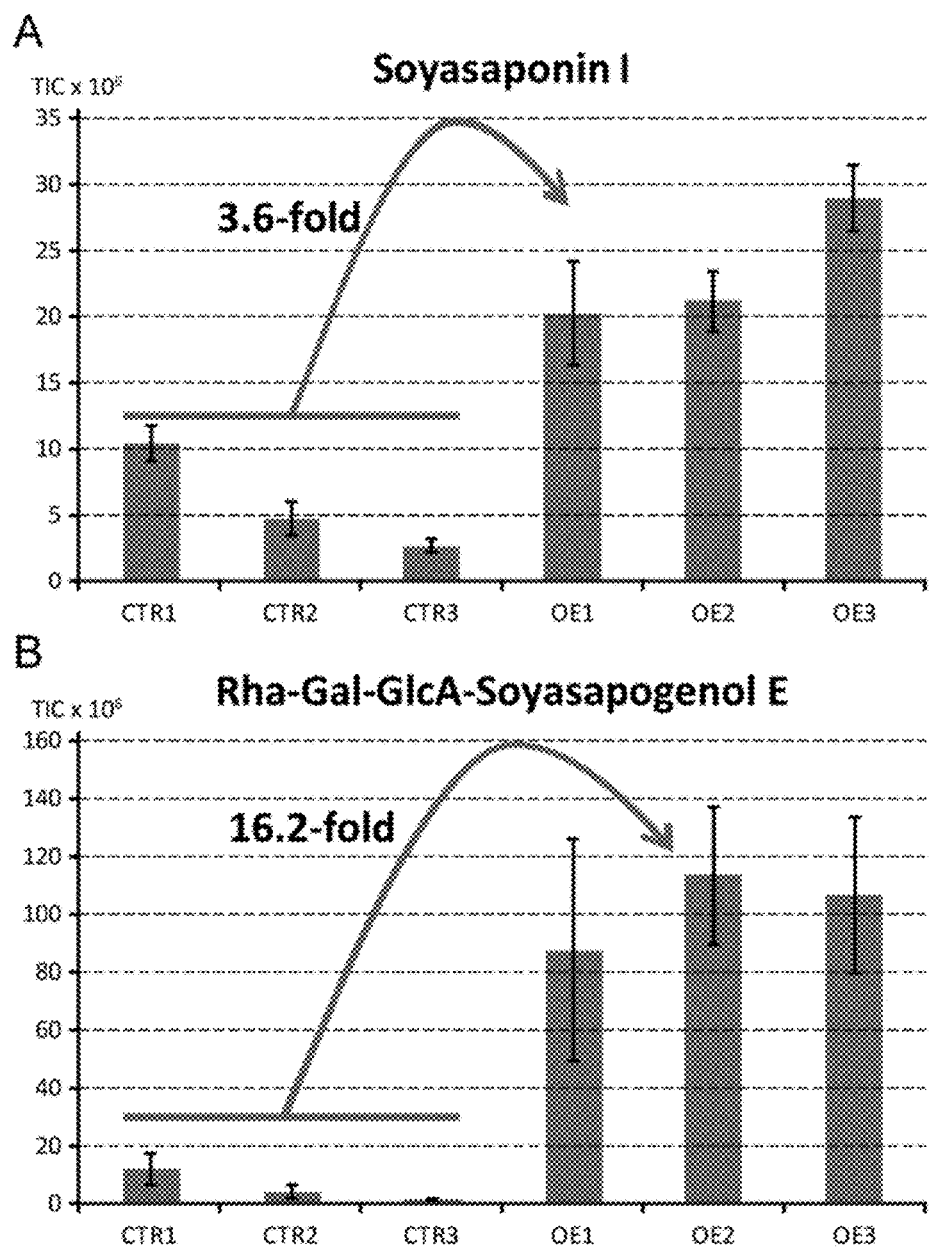
FIG. 5. Increased accumulation of saponins in *M. truncatula* hairy roots overexpressing MtbHLH25a. Depicted are the average TIC values (n=5; error bars, ±s.e.) of the peaks corresponding to the parent ion of Soyasaponin I (A) and Rha-Gal-GlcA-Soyasapogenol E (B) in three control (CTR) and three MtbHLH25a overexpression (OE) *M. truncatula* hairy root lines.

To assess the effects of overexpression of MtbHLH25a on the metabolite level, five cultures of each of the three MtbHLH25a OE lines and the three control lines were analyzed by liquid chromatography electrospray ionization Fourier transform ion cyclotron resonance mass spectrometry (LC-ESI-FT-ICR-MS, Pollier et al., 2011, *J. Nat. Prod.* 74:1462-1476). The resulting LC-MS chromatograms were processed and analyzed using the XCMS software package (Smith et al. 2006, *Anal. Chem.* 78:779-787) and yielded a total of 6,945 m/z peaks. A Student's t-test with Welch correction ($\alpha=10^{-5}$) identified 296 m/z peaks, corresponding to at least 19 metabolites, that were significantly different between the control and MtbHLH25a OE lines. Tentative identification of these 19 significantly different metabolites revealed that most of them were saponins with a soyasapogenol aglycone, and the intensity of the corresponding peaks indicated these metabolites were present in much higher levels in the MtbHLH25a OE lines as compared to the control lines (FIG. 5).

Example 6: Selection of bHLH25 Homologues from *Catharanthus roseus* that are Co-Regulated with Known Seco-Iridoid Biosynthesis Genes and Functional Analysis by Transient Expression Assays

Figure 6:
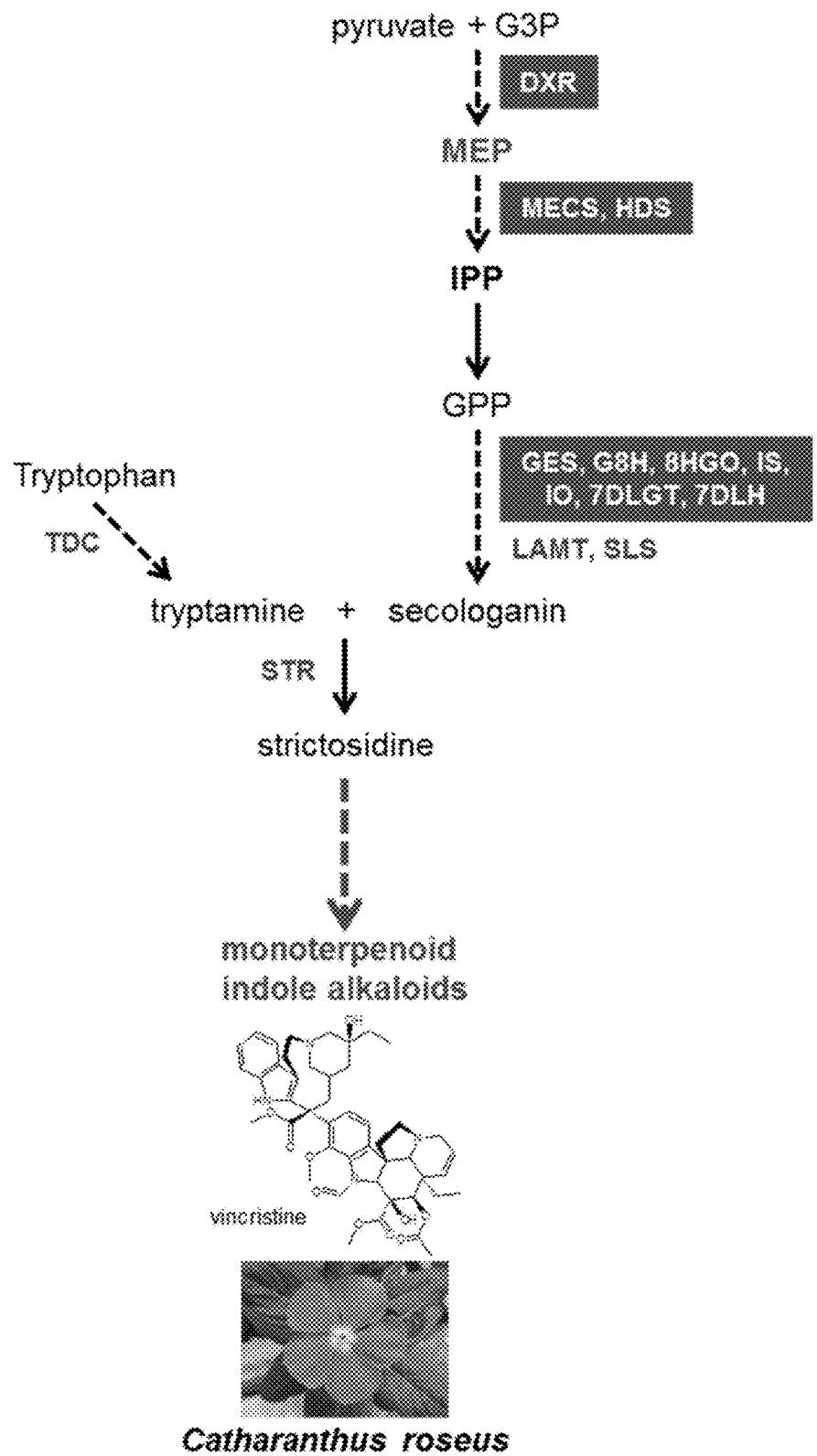
FIG. 6. Pathway leading to the production of monoterpenoid indole alkaloids (MIA) in *Catharanthus roseus*. MIA are produced from strictosidine, a condensation product of secologanin and tryptamine. 7DLGT: 7-deoxyloganetic acid glucosyl transferase, 7DLH: 7-deoxyloganic acid hydroxylase, DXR: 1-deoxy-5-xylulose-5-phosphate reductase, G3P: glyceraldehyde 3-phosphate, GES: geraniol synthase, G8H: geraniol-8-hydroxylase, GPP: geranyl diphosphate, HDS: (E)-4-hydroxy-3-methyl-but-2-enyl pyrophosphate synthase, 8HGO: 8-hydroxygeraniol oxidoreductase, IPP: isopentenyl diphosphate, IO: iridoid oxidase, IS: iridoid synthase, LAMT: loganic acid O-methyltransferase, MECS: 4-diphosphocytidyl-2-C-methyl-D-erythritol 2-phosphate synthase, MEP: 2-C-methyl-D-erythritol 4-phosphate, SLS: secologanin synthase, TDC: tryptophan decarboxylase, STR: strictosidine synthase.

*Catharanthus roseus* produces over 150 monoterpenoid indole alkaloid (MIA) compounds, which are derived from the central MIA compound strictosidine, a condensation product of the monoterpenoid (more specifically seco-iridoid, the term that is used hereinafter) compound secologanin and the indole compound L-tryptamine (FIG. 6) (Courdavault et al. 2014, *Curr. Opin. Plant Biol.* 19C:43-50; van der Heijden et al. (2004), *Curr. Med. Chem.* 11:607-628). Secologanin is exclusively produced from MEP-derived geranyl diphosphate (GPP), involving nine biosynthesis genes, of which the seven genes upstream of loganic acid methyltransferase (LAMT) are highly co-expressed (FIGS. 6 and 7) (Miettinen et al. (2014), *Nat. Commun.* 5:3606). Previously, the APETALA2 (AP2)-domain TF ORCA3 was identified as the JA-inducible regulatory TF that modulates the JA-induced expression of the genes of the indole branch of the pathway and several steps downstream of strictosidine (J. van der Fits, et al. (2000), *Science* 289:295-297). Overexpression of ORCA3 in *C. roseus* cell suspension cultures also increased the expression of LAMT and secologanin synthase 1 (SLS1), but not of the seco-iridoid genes upstream of LAMT (FIG. 6). The latter finding also indicated that the seco-iridoid branch of the pathway is limiting for MIA production in *C. roseus* cell suspension cultures (van der Fits et al. (2000), *Science* 289:295-297).

Figure 8:
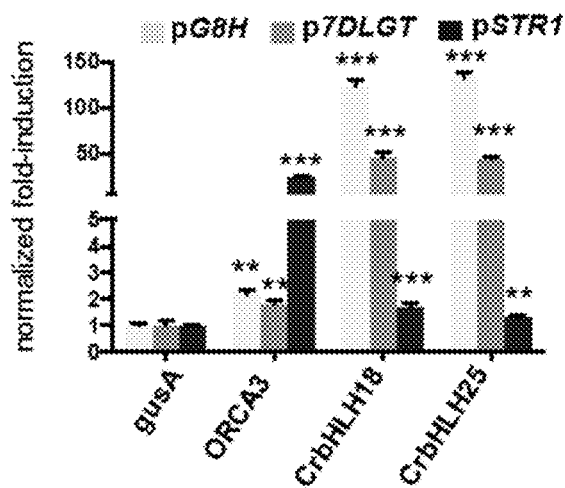
FIG. 8. Transient promoter trans-activation assays in *Nicotiana tabacum* protoplasts using a promoter:fLUC reporter construct and selected TFs. CrbHLH25 and CrbHLH18, but not ORCA2 transactivate pG8H and p7DLGT, whereas only ORCA3 transactivates pSTR1. Values are fold-changes relative to protoplasts transfected with a pCaMV35S:gusA (gusA) construct. The error bars designate SE of the mean (n=8). Statistical significance was determined by the Student's t-test (*P<0.1, P<0.01, *P<0.001).

To identify regulators of the seco-iridoid pathway branch, recently generated RNA-Seq data (Van Moerkercke et al. (2013), *Plant Cell Physiol.* 54:673-685) was mined for TFs that were highly co-expressed with the seco-iridoid genes upstream of LAMT. Among them, two bHLH TFs, both belonging to clade IVa of the family; thus, homologues of *M. truncatula* bHLH25a were identified. Both clade IVa bHLH TFs, called CrbHLH18 and CrbHLH25, were cloned analogous to the procedure used for the *M. truncatula* bHLH25a TF (primer sets P21+P22, P19+P20, respectively, see Table 3) and were found capable of transactivating the promoters of the geraniol-8-hydroxylase (G8H) and the 7-deoxyloganetic acid glucosyltransferase (7DLGT) genes in the *Nicotiana tabacum* protoplast-based screen (FIG. 8). The clade IVa bHLH TFs could not transactivate the promoter of the strictosidine synthase 1 (STR1) gene, delimiting their action range to the seco-iridoid branch of the MIA pathway and distinguishing it from that of ORCA3 (FIG. 8).

Example 7: Enhanced Production of Seco-Iridoids and Monoterpenoid Indole Alkaloids in CrbHLH25 Overexpressing *C. roseus* Cell Suspension Lines To assess the effect of overexpression of the clade IVa bHLH TFs on MIA biosynthesis in plants, stably transformed *C. roseus* cell cultures were generated. Therefore, *C. roseus* cell line MP183L was transformed by co-bombardment of a TF plasmid or the empty overexpression plasmid as a control with a plasmid carrying a hygromycin resistance gene (as described in van der Fits et al. (1997), *Plant Mol. Biol.* 33:943-946). Individual calli resistant to 50 mg/l hygromycin-B were converted to transgenic cell suspensions maintained weekly in LS-13 medium supplemented with hygromycin. Cell lines were screened for high expression levels of the co-transformed TF using RNA blot hybridization. For RNA blot analysis, total RNA was extracted from frozen cells by hot phenol/chloroform extraction followed by overnight precipitation with 2 M lithium chloride and two washes with 70% v/v ethanol, and resuspended in water. Ten µg RNA samples were subjected to electrophoresis on 1.5% w/v agarose/1% v/v formaldehyde gels and blotted onto Genescreen nylon membranes (Perkin-Elmer Life Sciences, on the internet at perkinelmer.com). Probes were 32P-labeled by random priming. (Pre-)hybridization and subsequent washings of blots were performed as previously described (J. Memelink, K. M. M. Swords, L. A. Staehelin, J. H. C. Hoge, in *Plant Molecular Biology Manual*, S. B. Gelvin, R. A. Schilperoort, Eds. (Kluwer Academic Publishers, Dordrecht, The Netherlands, 1994), pp. F1-F23) with minor modifications. For metabolite profiling, *C. roseus* cells from three biological repeats of each selected independent transgenic line were harvested 5 days after transfer, frozen in liquid nitrogen and freeze-dried. One-hundred mg dried cell mass was extracted in two steps with 10 ml methanol and centrifuged. The dried supernatant was resuspended in 1 M phosphoric acid and filtered. Extracts were analyzed using an Agilent Technologies 1100 HPLC. For the seco-iridoids, tryptophan and tryptamine, an Agilent Technologies Zorbax eclipse XDB-C18 4.6×250 mm 5-µm column was used. MIA were analyzed using a Phenomenex Luna C18(2) 4.6×150 mm 5-µm Axia packed column. The Phenomenex column used a flow rate of 1.5 ml/minute and a 25 µl injection volume using the solvents: A, 0.1% trifluoroacetic acid (TFA) in $H_2O$, and B, acetonitrile with 0.1% TFA. The Agilent Technologies column used a flow rate of 1.5 ml/minutes and a 50 µl injection volume using the solvents: A, 5 mM disodiumhydrophosphate and B, acetonitrile. Seco-iridoids were detected using 220, 254, 280, 306 and 320 nm wavelengths. MIA were analyzed using 220, 240 and 280 nm wavelengths.

Figure 7:
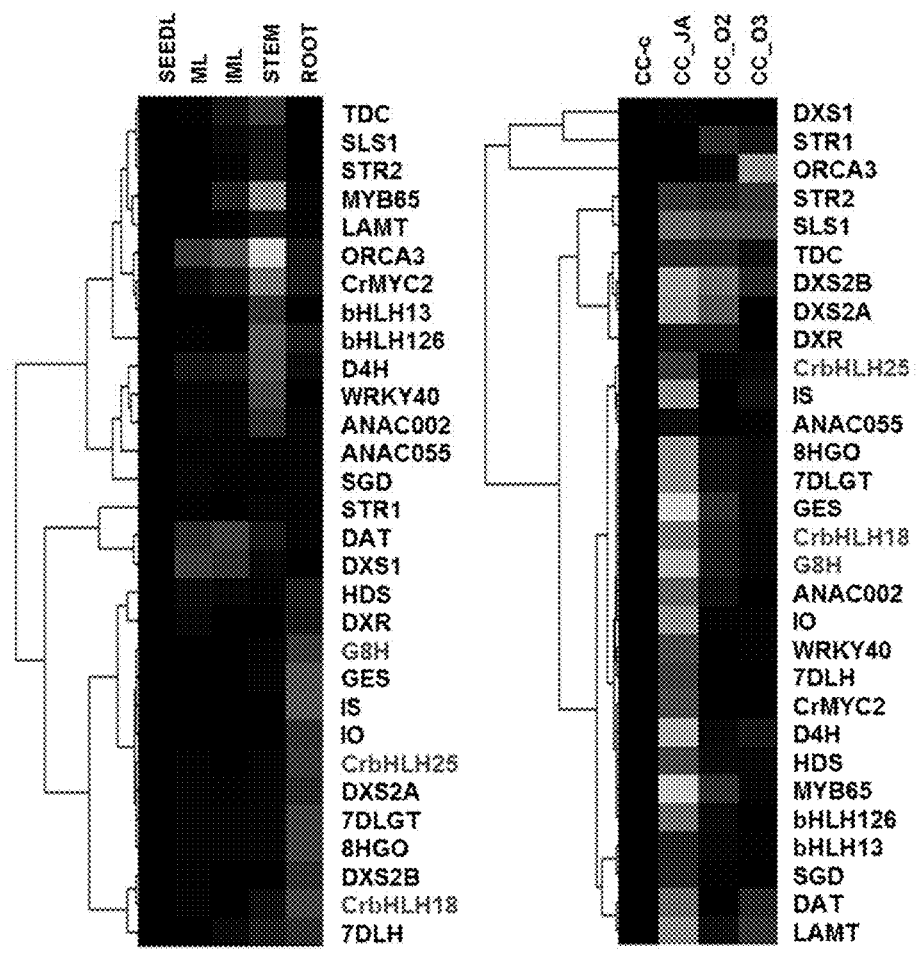
FIG. 7. Co-expression analysis of CrbHLH25 and CrbHLH18 with G8H and selected seco-iridoid and monoterpenoid indole alkaloid genes in different conditions. Left panel represents selected RNA-Seq data from the Medicinal Plant Genomics Resource (MPGR) (on the internet at medicinalplantgenomics.msu.edu). SEEDL: seedlings, ML: mature leaf, IML: immature leaf. Values were normalized to the seedling reads. The right panel is from RNA-Seq data from the SmartCell consortium and available on the ORCAE database (on the internet at bioinformatics.psb.ugent.be/orcae/overview/Catro). CC_c: mock-treated cell culture, CC_JA: jasmonate-treated cell culture, CC_O2 and CC_O3: ORCA2 and ORCA3 overexpressing cell culture. Values were normalized to the mock-treated cell culture. Blue and yellow denote relative down-regulation and up-regulation, respectively.
Figure 9:
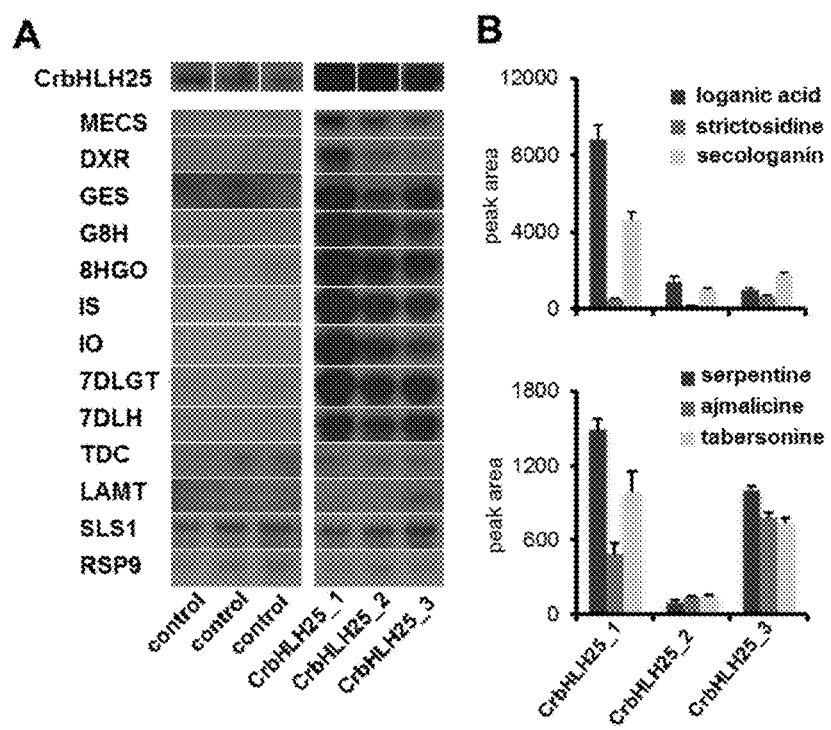
FIG. 9. CrbHLH25 overexpression stimulates MIA gene expression and metabolite accumulation. Constitutive overexpression of CrbHLH25 suspension cells of *C. roseus*. Three independent transformant lines were selected for both pCaMV35S:CrbHLH25 and the pCaMV35S:gusA control. The error bars designate SE of the mean (n=3). (Panel A) Expression analysis in transformed cells by RNA-blot hybridization analysis for selected biosynthesis genes. (Panel B) Accumulation of seco-iridoid and MIA compounds in CrbHLH25 overexpressing cell lines. Control cell lines did not accumulate detectable levels of these compounds. In all cases, statistical significance was determined by the Student's t-test (*P<0.1, P<0.01, *P<0.001).

In contrast to differentiated *C. roseus* plant tissues, the *C. roseus* cell suspension line MP183L does not accumulate any secologanin, strictosidine or MIAs without exogenous supply of JA and loganin, illustrating that the seco-iridoid pathway is limiting in this cell line (van der Fits et al. (2000), *Science* 289:295-297). This was corroborated by analysis of recent RNA-Seq data that confirmed the low transcript accumulation of MEP and seco-iridoid genes in these suspension cells compared to that of the ORCA3-regulated genes, such as LAMT, SLS1 and STR1 (FIG. 7). In contrast, the CrbHLH25 overexpressing cells showed a high up-regulation of the MEP and seco-iridoid genes, but not of the known ORCA3-regulated genes (FIG. 9, Panel A). The effect on the transcript level in the suspension cells was accompanied by a strong effect on the metabolite level. Loganic acid, secologanin and strictosidine, as well as MIAs such as ajmalicine, serpentine and tabersonine, accumulated to levels previously unreported in untreated control *C. roseus* suspension cells (FIG. 9, Panel B). Control cell lines did not accumulate detectable levels of these compounds.

Example 8: Reciprocal Transactivation of MIA and Saponin Biosynthesis Genes by MtbHLH25a and CrbHLH25

Figure 10:
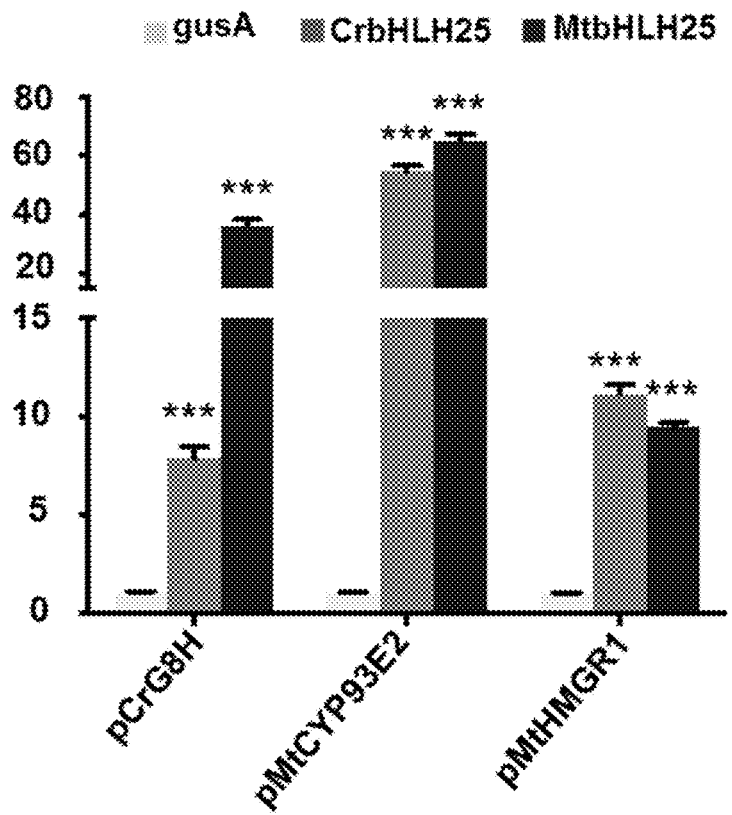
FIG. 10. Reciprocal transactivation of MIA and TS biosynthesis genes by MtbHLH25 and CrbHLH25. Values are fold-changes relative to protoplasts transfected with a pCaMV35S:gusA (control) construct. The error bars designate SE of the mean (n=8). Statistical significance was determined by the Student's t-test (***P<0.001).

The outcome of the above screens and functional studies in *M. truncatula* and *C. roseus* suggest that clade IVa bHLH factors play a conserved role in the regulation of plant terpenoid biosynthesis. To further assess this hypothesis, transient transactivation assays in tobacco protoplasts were performed in which the bHLH TFs and promoters were switched from both species. Evaluation of the effect of CrbHLH25 overexpression on the pCYP93E2 or pHMGR1 reporter genes demonstrated that CrbHLH25 can transactivate *M. truncatula* saponin gene promoters (FIG. 10). Conversely, transactivation of the G8H promoter by MtbHLH25 indicated that the clade IVa bHLH TFs from both species act reciprocally and thus fulfill a conserved role in diverse plant species (FIG. 10).

*C. roseus* and *M. truncatula* belong to the Apocynaceae and Fabaceae, respectively. Both are dicot plant families, but are representative of the two different clades within that group, the Asterids and Rosids, respectively. Hence, the results show that clade IVa bHLH TFs in two distantly related dicot species exert a similar function in regulating terpenoid biosynthesis. These TFs are capable of acting on different classes of terpenoids and act as generic metabolic engineering tools to boost production of high-value bioactive molecules to exploitable levels in plant species.

Tables

TABLE 2

| Gene and promoter sequences | |
|---|---|
| ID | Sequence |
| MtbHLH25a | Nucleotide (SEQ ID NO: 1) |
| | ATGGAGGATTCACTGGAAAATTTGATTTCTTA |
| | TATGGAAATGGAAGATGATGTGATCTTGAATC |
| | AAAGTAGCACCACCACATTTGATGAGCAAGAG |
| | TTTCTCAAAGATATCATCCTTGAAGAACCAGA |
| | ATGTATTGAACTCTCTTCTTATCTTTGTTCCA |

TABLE 2-continued

Gene and promoter sequences

| ID | Sequence |
|---|---|
| | ATAAAACCAAAGACAATAGTACAACTATAATT<br>AATGTTGAAGGTGATGCTACTAGCCCCACAAA<br>TAGTATTTTGTCCTTTGATGAGACAAGTTTAT<br>TTTGTGGTGATTATGAGAATGTTGAAACAAAC<br>CACAAAAGTAATAACTCCAACTCAATCAAGTC<br>TTTGGAAAGATCTTGTGTTAGTTCTCCAGCCA<br>CATACCTTCTATCTTTTGGTAACTCAAGTATT<br>GAACCAATCATTGAACCAATGTCACATAAAAC<br>TAAAAGAAGGACAGATGAATCAAGGGGGGTGA<br>AGGAAGCAACAAAGAAGGTTAGAAGATCATGT<br>GAGACAGTACAAGATCATTTGATGGCTGAGAG<br>GAAAAGGAGAAGGGAATTAACTGAGAATATCA<br>TAGCACTTTCAGCCATGATCACTGGCTTGAAA<br>AAGATGGACAAGTGTTATGTACTTAGCGAAGC<br>TGTGAATTACACAAAACAGCTTCAAAAGCGCA<br>TTAAAGAATTGGAGAATCAAAACAAAGATAGC<br>AAACCAATCCAGCAATATTCAAGTGGAAATC<br>TCAAGTTTCATCAAATAAAAAGAAGTCCTCAG<br>AATCACTGCTCGAGGTTGAAGCTAGAGTCAAA<br>GAAAAGGAAGTACTCATCAGAATTCATTGTGA<br>GAAGCAAAAGACATAGTGCTCAAATACATG<br>AATTGCTTGAAAAGTTCAATATCACTATAACA<br>AGTAGTAGCATGTTACCATTTGGTGATTCTAT<br>TCTTGTAATCAACATTTGTGCTCAGATGGATG<br>AAGAAGACAGCATGACCATGGATGACCTTGTG<br>GAAAATCTGAGAAAATATCTATTGGAAACTCA<br>TGAGAGTTACTTGTGA<br>Protein (SEQ ID NO: 5)<br>MEDSLENLISYMEMEDDVILNQSSTTTFDEQE<br>FLKDIILEEPECIELSSYLCSNKTKDNSTTII<br>NVEGDATSPINSILSFDETSLFCGDYENVETN<br>HKSNNSNSIKSLERSCVSSPATYLLSFGNSSI<br>EPIIEPMSHKTKRRTDESRGVKEATKKVRRSC<br>ETVQDHLMAERKRRRELTENIIALSAMIPGLK<br>KMDKCYVLSEAVNYTKQLQKRIKELENQNKDS<br>KPNPAIFKWKSQVSSNKKKSSESLLEVEARVK<br>EKEVLIRIHCEKQKDIVLKIHELLEKFNITIT<br>SSSMLPFGDSILVINICAQMDEEDSMTMDDLV<br>ENLRKYLLETHESYL |
| MtbHLH25b | Nucleotide (SEQ ID NO: 2)<br>ATGGAGGAGAATCCATGGGCAATTGGTCTTA<br>TGATTTGGAAATGGAAGAACATTGTGTCACA<br>CAAACAACACATTTGACGAAGAGTTCCTCAGA<br>GATATCCTGTATCAGATTCCACAAGATCAATT<br>CAATGTTCCTATTGCCACAACTGACCTAGTAA<br>ACAACTCATCCATCAATGTGTCACAACATGCT<br>GAAGAAATGCCAACCAACTCATTATCAATACC<br>AACAACTGAACAACATCATGATTCTTTGCCTT<br>TGTCATCATCAACAGCTAACCAAGGGTCGAAT<br>TCGAAGAAGCCTCGAAACACTTCGGATACACT<br>AGATCACATAATGTCAGAGAGAAATAGGAGAC<br>AACTACTTACAAGTAAGATCATAGAACTTTCG<br>GCCTTGATACCTGGATTGAAGAAGATTGAAA<br>GGTTCATGTGGTAACGGAAGCTATCAATTACA<br>TGAAACAACTTGAAGAACGTTTGAAAGAGCTA<br>GAAGAAGACATTAAGAAGAAAGATGCAGGATC<br>ATTGAGCACCATAACAAGATCTCGTGTTTTAA<br>TTGACAAGACATTGCAATCGGTGAAATGAAC<br>ACTGAAGAATGTTACGGGAGAAATGAATCACT<br>TCTAGAGGTTGAAGCTAGGATTCTAGAGAAGG<br>AAGTTTTAATCAAGATTTATTGTGGAATGCAA<br>GAAGGGATTGTGGTCAATATAATGTCCCAGCT<br>TCAACTTCTTCATCTGTCCATAACAAGTATCA<br>ATGTCTTGCCATTTGGAAATACTCTTGACATC<br>ACCATTATTGCCAAGATGGGTGACAAATACAA<br>CTTGACAATAAAGGACCTAGTGAAAAACTAA<br>GAGTAGTGGCTACGTTGCAGGTATCTCATAAT<br>GTGCAATTTCATATCTAA<br>Protein (SEQ ID NO: 6)<br>MEENPWGNWSYDLEMEEHLCHTNNTFDEEFLR<br>DILYQIPQDQFNVPIATTDLVNNSSINVSQHA<br>EEMPTNSLSIPTTEQHHDSLPLSSSTANQGSN<br>SKKPRNTSDTLDHIMSERNRRQLLTSKIIELS<br>ALIPGLKKIDKVHVVTEAINYMKQLEERKEL<br>EEDIKKKDAGSLSTITRSRVLIDKDIAIGEMN |
| | TEECYGRNESLLEVEARILEKEVLIKIYCGMQ<br>EGIVVNIMSQLQLLHLSITSINVLPFGNTLDI<br>TIIAKMGDKYNLTIKDLVKKLRVVATLQVSHN<br>VQFHI |
| MtbHLH25c | Nucleotide (SEQ ID NO: 3)<br>ATGGAGGAAATCAACAACTCAGCTATGAAAGT<br>ATCATCATCAATCAGCAGCTGGTTATCTGATT<br>TGGAAATGGACGAATACAATATATTTGCTGAG<br>GAATGCAACCTTAATTTCCTTGATGCTGATGT<br>GGGAGGGTTTCTTTCAAATGACATATCTAATG<br>TATTTCAAGAACAAAACAAACAACAATGTTTA<br>TCTTTGGGGTCCACTTTTCATGAAACAATTGA<br>TAATAGTGACAAAAACAATGAATCTCTTTCTC<br>CATCTTTTCAGTTTCAAGTTCCATCTTTTGAC<br>AACCCCCCAAATTCATCCCCTACTAACTCAAA<br>AGAGAATATTGAAACAATACCATTGTCTCCAA<br>CCGATTTGGAAAATATGAATCACTCAACAGAA<br>ACCTCAAAAGGGTCATTGGAAATAAAAGTT<br>GGAAACAAAAACCTCAAAAAGCAAAAGGCCAC<br>GTGCTCATGGTAGAGATCACATCATGGCTGAG<br>AGAAATCGAAGAGAGAAACTCACCCAAAGCTT<br>CATTGCTCTTGCAGCTCTTGTTCCTAACCTTA<br>AGAAGATGGATAAACTATCTGTACTAATTGAC<br>ACTATCAAATACATGAAAGAGCTTAAAAATCG<br>TTTGGAAGATGTGGAAGAACAAAACAAGAAAA<br>CAAAAAAAAAATCATCGACCAAACCATGCCTA<br>TGCAGCGATGAAGATTCGTCATCATGTGAGGA<br>TAACATTGAATGTGTTGTTGGTTCACCATTTC<br>AAGTGGAAGCAAGAGTGTTAGGAAAACAAGTG<br>CTGATTCGGATCCAATGCAAGGAGCATAAGGG<br>GCTTCTGGTTAAAATTATGGTCGAAATTCAAA<br>AATTTCAACTATTTGTTGTCAATAACAGTGTC<br>TTACCCTTTGGAGATTCTACGCTCGACATTAC<br>CATCATTGCTCAGTTGGGTGAAGGGTACAACT<br>TGAGCATAAAGGAACTTGTGAAGAACGTACGC<br>ATGGCATTATTGAAGTTTACGTCATCATAA<br>Protein (SEQ ID NO: 7)<br>MEEINNSAMKVSSSISSWLSDLEMDEYNIFAE<br>ECNLNFLDADVGGFLSNDISNVFQEQNKQQCL<br>SLGSTFHETIDNSDKNNESLSPSFQFQVPSFD<br>NPPNSSPTNSKENIETIPLSPTDLENMNHSTE<br>TSKGSLENKKLETKTSKSKRPRAHGRDHIMAE<br>RNRREKLTQSFIALAALVPNLKKMDKLSVLID<br>TIKYMKELKNRLEDVEEQNKKTKKKSSTKPCL<br>CSDEDSSSCEDNIECVVGSPFQVEARVLGKQV<br>LIRIQCKEHKGLLVKIMVEIQKFQLFVVNNSV<br>LPFGDSTLDITIIAQLGEGYNLSIKELVKNVR<br>MALLKFTSS |
| MtbHLH25d | Nucleotide (SEQ ID NO: 4)<br>ATGGAGGAAATCAACAACACACCAATGAACGT<br>ATCAGAAGAAACCAGCAAATGGCTATCTGATT<br>TGGAAATGGGATGAGTATAATTTATTTCCTGAA<br>GAATGCAACCTAAACTTCCTTGATGCTGATGA<br>GGAAGAGTTTCTTCCACAAGAACAAACCCAAC<br>AACAATGTTTGAGTTCAGAGTCCAATTCCACA<br>ACTTTCACCAACTCATTCACTGATGAAACAAA<br>TTTTGACTCTTTTGACTTTGATTTTGAAATTG<br>AGAGACCAACCATGGAGCTGAACACAATCTTT<br>AGTGACAACAGCATCATTGAAACCATTTCACC<br>AAAACTTTCTCCATCATCATCTAACTCATCTT<br>TGCACTCTCAGATTTGTCTTTTGACAACCTC<br>CCAAATTCACCTGCTACCAACACCCCTCAATT<br>TTGTGGACTCACCCCTACCTTAATCTCAAAGT<br>CAAAACAAAACAAAACAGTGTTAGTGTCTCCA<br>CCCCAAATAAGAACATTCATGTCTCCAACTCA<br>AAATCCTATAGGGTTATCCAAAAATCAAAACT<br>TTGCAACAAAAACCTCTCAAACCAAAGGTCTC<br>GAGCCAACGCTGATGATCATATCATGGCTGAG<br>AGAGAACGCAGAGAAACTTAGCCAAAGCT<br>TCATTGCTCTTGCAGCTCTTGTTCCTAACTTG<br>AAAAAGATGGACAAGCTTCTGTATTAGCTGA<br>GTCTATAATCTACGTGAAAGAGCTTAAAGAGC<br>GTTTGGAAGTTTTGGAAGAACAAAACAAGAAA<br>ACAAAGGTAGAGTCCGTGGTTGTTCTGAAGAA |

TABLE 2-continued

Gene and promoter sequences

| ID | Sequence |
|---|---|
| | ACCAGACCATAGTATCGATGATGATGATGATG<br>ATGATGATAACTCATCATGTGATGAGAGTATT<br>GAAGGTGCTACTGATTCATCCGTACAAGTGCA<br>AGCAAGAGTGTCAGGGAAAGAGATGCTGATTC<br>GGATTCACTGCGAGAAGCACAAGGGAATTCTG<br>GTGAAAGTCATGGCTGAGATTCAAAGCTTTCA<br>ATTGTTTGCTGTGAATAGTAGTGTCTTACCCT<br>TTGGGGATTCCATTGACATTACTATCATTGCT<br>GAGATGGGTGAAAGGTACAACTTGAGCATAAA<br>GGAACTTGTCAAGAACCTACACATGGCAGCAT<br>TGAAGTTTATGTCATCAAAAATCACAGACTGA<br>Protein (SEQ ID NO: 8)<br>MEEINNTPMNVSEETSKWLSDLEMDEYNLFPE<br>ECNLNFLDADEEEFLPQEQTQQQCLSSESNST<br>TFTNSFTDETNFDSFDFDPEIERPTMELNTIF<br>SDNSIIETISPKLSPSSSNSSLHSQILSFDNL<br>PNSPATNTPQFCGLTPTLISKSKQNKTVLVSP<br>PQIRNIHVSTQNPIGLSKNQNFATKTSQTKRS<br>RANADDHIMAERKRREKLSQSFIALAALVPNL<br>KKMDKASVLAESIIYVKELKERLEVLEEQNKK<br>TKVESVVVLKKPDHSIDDDDDDDNSSCDESI<br>EGATDSSVQVQARVSGKEMLIRIHCEKHKGIL<br>VKVMAEIQSFQLFAVNSSVLPFGDSIDITIIA<br>EMGERYNLSIKELVKNLHMAALKFMSSKITD |
| bHLH domain of MtbHLH25a | TVQDHLMAERKRRRELTENIIALSAMIPGLKK<br>MDKCYVLSEAVNYTKQLQKRIKEL<br>(SEQ ID NO: 9) |
| bHLH domain of MtbHLH25b | DTLDHIMSERNRRQLLTSKIIELSALIPGLKK<br>IDKVHVVTEATNYMKQLEERLKEL<br>(SEQ ID NO: 10) |
| bHLH domain of MtbHLH25c | HGRDHIMAERNRREKLTQSFIALAALVPNLKK<br>MDKLSVLIDTIKYMKELKNRLEDV<br>(SEQ ID NO: 11) |
| bHLH domain of MtbHLH25d | NADDHIMAERKRREKLSQSFIALAALVPNLKK<br>MDKASVLAESIIYVKELKERLEVL<br>(SEQ ID NO: 12) |
| CrbHLH25 | Nucleotide (SEQ ID NO: 15)<br>ATGACAATGATGATGACGATGGATAATTCAGT<br>CAATTCATGGTTCTCTGATCTGGGAATGGAGG<br>ATCCTTTCTCCAGCGATCAATATGACATCACG<br>GACTTTCTGAATGAGGATTTCGCTGCACTTGG<br>AGAGGACTTGCAAGCATTCACTCCAACAGCCG<br>AATCTGATTCATCCAATAACTTCATTAATATT<br>CCAACTAGCAATTCATCAAACACCTTATGTGC<br>ATTGGCTACGGAACTTCCTTCGGTTGTGGCCG<br>AAATTCCAACCACCATCACTGCCACTACCACT<br>ACTAAAAACGAAAATCCAATTCGTCGACAAA<br>TCAAAATGTGCCGAATGCTCGTAGAGCCGCTC<br>GTACTCCCATCGTTCTCACATTTGGGAATACA<br>CGGCAGAAACCAATCCTAATAAACACAGCTTA<br>AGCCCTGATATTAATGATGATTCATTAATATC<br>AACTGAGAATTTGACCTCCCAAGGAAATCTTG<br>AAGAGGCAGTAGCAGCTGCCAAAAGTACAAAA<br>CTAAACAAGAAAACTGGTGGCCGCGTTAGGCC<br>TGCATCCCAAACCTATGATCACATAATTGCTG<br>AAAGAAAGCGACGTGAGCAGCTCAGCCAGCAT<br>TTTGTCGCACTTTCTGCCATTGTTCCTGGCCT<br>TAAGAAGATGGATAAACTTCTGTACTTGGAG<br>ATGCGATTACCTACTTAAAACATATGCAAGAG<br>CGAGTAAAATCACTAGAAGAACAAACAACAAA<br>ACAAACAATGGAATCAGTGGTGCTAGTGAAGA<br>AATCACAAGTGTTAGTTGAAGATGAAGGTTCT<br>TCAGATGAGATTGATCAAGATCAGTCCTCGTC<br>ACAGCTCCCTGAAATTGAAGCCAAAGTTTGT<br>ACAAAACCATTTACTCAGAGTTCACTGCGAA<br>AAGAACAAAAGGGTCCTTATTAATATACTCTC<br>TCAACTTGAAACACTCAATCTTGTTGTTACTA<br>ACACCAGCGTTTCAGCTTTTGGAAGTTTGGCT |

TABLE 2-continued

Gene and promoter sequences

| ID | Sequence |
|---|---|
| | CTTGATATTACTATCATCGTTGAGATGGAGAA<br>AGAATCAAGCATAAACATGAAAGAACTTATTC<br>AAACTCTTCGGTCAGCTGTCATGCGTGCAAAT<br>TTAGAAGATTGA<br>Protein (SEQ ID NO: 17)<br>MTMMMTMDNSVNSWFSDLGMEDPFSSDQYDIT<br>DFLNEDFAALGEDLQAFTPTAESDSSNNFINI<br>PTSNSSNTLCALATELPSVVAEIPTTITATTT<br>TKKRKSNSSTNQNVPNARRAARTPIVLTFGNT<br>TAETNPNKHSLSPQDINDDSLISTENLTSQGN<br>LEEAVAAAKSTKLNKKTGGRVRPASTYDHIIA<br>ERKRREQLSQHFVALSAIVPGLKKMDKTSVLG<br>DAITYLKHMQERVKSLEEQTTKQTMESVVLVK<br>KSQVLVEDEGSSDEIDQDQSSSQLPEIEAKVC<br>DKTILLRVHCEKNKRVLINILSQLETLNLVVT<br>NTSVSAFGSLALDITIIVEMEKESSINMKELI<br>QTLRSAVMRANLED |
| CrbHLH18 | Nucleotide (SEQ ID NO: 16)<br>ATGATGACGATGATGATGGATAATTCAGCAAC<br>GTCCCCTAATTGCTTCTCTGAGCTTCAGCAGG<br>GAATGGAGGATCCTACTAACTTCCTCATTAGC<br>AATGATGATAAATGTGATGTAATGGAGTTTTT<br>GGATGAAGATATATGTGCAGTTCTTGGTCAAG<br>ACTACTTCCAAATTTCCTCTTTCTCCCCCAAT<br>GACTACTCATTTTCTCCAAACTTGGATCCAAA<br>TTCCACTTTATATCCATCTTCTTCTTCAACTC<br>CTACGGATATTCATGACCAATCTCCACCATTT<br>ATGCTTAATGATGATATTGATGAAATAATGAA<br>TAGACGACCAGCCAAACAGCTGAAGAGCACTA<br>GTAATAATAATCAAAATAACCAAAATCCGTCG<br>ACTATTCATGATAGCTTTGATGCTCAAATGTC<br>TACTCCCTACCTTCTTACTTTTGGGAATCCAA<br>ATTCACCTGAAATTATTAATCCACCTCATCAT<br>CAACAACACCATCAACCTAATGCAACATTAAA<br>CTTAAACCCCTCTGATGAAGATGTTCAAGTAT<br>CCGAGGTTTTCAACTCCCAAAGTTCATCATAT<br>GGAAATCTTATTGAAGAGGAGGCAGCAGCACC<br>CAAAAGTTCAAAACCAACGTCCAAGAAAAGTG<br>GAGGCCGTGTAAGGCCGGCTTCTCAAACTTAT<br>GATCACATTATAGCTGAAAGAAAGAGAAGGGA<br>GATCCTCAGCCAGCGCTTTATGGCTCTTTCTA<br>CTCTAGTTCCCGGTCTCAAGAAGATGGATAAA<br>ACATCAGTACTTGGAGATGCAATTAAGTACTT<br>AAAATATCTCCAAGAAAGAGTTCAGATTCTTG<br>AGGATCAAGCAGCCAAACAAACTATGGAATCG<br>GTGGTGATGGTGAAGAAAATCACATGTCTTCAT<br>CCAAGAAGAAGAAGATGATGAAGAAGGATCTT<br>CAGATGATCAGATCACCAGCGATGGCGGAAGC<br>TCAGAAGAACAACCATTACCTGAAATTGAGGT<br>TAAAGTTTGCAATAAAACACTTCTTCTGAGAA<br>TTCACTGCGAGAAGCAAAAAGGGGTGCTTATT<br>AAGTTACTTAATGAGATTGAAAGGCTCAATCT<br>TGGCGTTACCAACATTAACGTTGCACCCATTTG<br>GAAGCTTGGCTCTTGACATTACCATTATTGCT<br>GAGATGGAGAAAGAGTACAATATGACAACGGT<br>ACAAGTGATTAAAAATCTTCGGTCAGTTCTTC<br>TTAACAGTCCACCAATGGCAGACTGA<br>Protein (SEQ ID NO: 18)<br>MMTMMMMDNSATSPNCFSELQQGMEDPTNFLIS<br>NDDKCDVMEFLDEDICAVLGQDYFQISSFSPN<br>DYSFSPNLDPNSTLYPSSSSTPTDIHDQSPPF<br>MLNDDIDEIMNRRPAKQLKSTSNNNQNNQNPS<br>TIHDSFDAQMSTPYLLTFGNPNSPEIINPPHH<br>QQHHQPNATLNLNPSDEDVQVSEVFNSQSSSY<br>GNLIEEEAAAPKSSKPTSKKSGGRVRPASQTY<br>DHIIAERKRREILSQRFMALSTLVPGLKKMDK<br>TSVLGDAIKYLKYLQERVQILEDQAAKQTMES<br>VVMVKKSHVFIQEEEDDEEGSSDDQITSDGGS<br>SEEHPLPEIEVKVCNKTLLLRIHCEKQKGVLI<br>KLLNEIERLNLGVTNINVAPFGSLALDITIIA<br>EMEKEYNMTTVQVIKNLRSVLLNSPPMAD |
| bHLH domain of CrbHLH25 | (SEQ ID NO: 19)<br>QTYDHIIAERKRREQLSQHFVALSAIVPGLKK<br>MDKTSVLGDAITYLKHMQERVKSL |

TABLE 2-continued

Gene and promoter sequences

| ID | Sequence |
|---|---|
| bHLH domain of CrbHLH18 | (SEQ ID NO: 20)<br>QTYDHIIAERKRREILSQRFMALSTLVPGLKK<br>MDKTSVLGDAIKYLKYLQERVQIL |
| pHMGR1 | (SEQ ID NO: 21)<br>ATTGGTAGGATCAATTGTTGATTGTCTTGGTT<br>TATGTAAAATGTTAAATGTGACAATTAAAA<br>GAAACGGAGGTAGTACTTCTATCATATTTAAT<br>GCTATTACTTCTAAATTCGTTTTCAATTATTT<br>ATGTTTGAATCCTCCGAGTGTCAATTTTTGTT<br>GATTTGTTTATAGTGGGATTGGTCCTTTGGAT<br>TAGTCGGTTCTTGAATCAAATACTAAATTTTC<br>AAACAAAAATTAGATTTTACTTTTCTATAAC<br>CATTTTATTATCATAGAAAAAAAAATTAAATC<br>TCCGAAAAATTATCATGAACAAGTTTTCATGA<br>GGGACAATTTAGAAAATGCAATTATGGCTAAA<br>CTATGTTTCAAGTCCCTTAAATTGTTCATTTT<br>GTTCACTTAAATTACAAACATTGAGTTATTCA<br>AATAAAAATTACAAACATTGAGTAAGAAAACA<br>AAATTAAACACGTTTTTGACTTTAGATTCGAT<br>TCATATTAAACACATTTGAGTCAAAAACAAA<br>TTAAACACGTTTTTTTTGCAGCACAAGTGATG<br>TATAAAACTAATTAGTTTTTATTTCAGCAACA<br>AAAAATGTACTTATAGTTTGATTAGTTTGTGC<br>AAATAAGAAATATATATAGTATTTTAGAAACG<br>TCAAGTAAAGGCTTCTTCTAGTGATGTGTAAT<br>GTTGGCATCTCTCCTCCATAAAATATGTTATC<br>TTGGAGTAAAAGTTAGGTACTGATTACAATAT<br>TCTTCCCTCGTTGTTCACGAGTTCCTTACGAT<br>CTAGCTATCAAGCTACTGTTACTTGACTTCTT<br>AAAATATTGGCATATACCTAATTCCTCACTCA<br>CTCCCTGAGTACTCTTTATCTATAAATAACAT<br>TCAAAATAAATCTTGGCATTCATTTTCAAGTT<br>AAGTTTCAATCATCCCCTAACCTGAACTCCTT<br>TTTCTCCTTTCTTTTTCCATTTTCGGATTTCA<br>AATCCTTCACTTAATAACCAAGAGAAAGAGAG<br>AGAGAGAG |
| pBAS | (SEQ ID NO: 22)<br>TAATTAATTAATTTGTAGTAGTCCTCGTTTGT<br>GACCACGCTTCCCTCGTGTTTCATTTATTTTA<br>TCCTGCTCTCCACGCTACTCGCTACATATA<br>TAATAATAATCAATGAATGTATATTGTTAAAT<br>TCCATCCTGTTCACCAATAATGATTGAATTCA<br>AGAATTAATTTTAAATATATATTCTAAAATAA<br>AAGGAAACTGCAAAAAATAAACATGAATCAT<br>ATGAGACAAAAATGAAGAGATAACACTTATAC<br>TGCTTAATTATTATCATTGTAAAGATAAATTG<br>AGAAGAATACATGACGGCAACTGCAACTCAAT<br>GGAAGAACACTTACAAGATGTATATGAAAACA<br>CCTACTTCAAAAATGTACATTAAAGCGAAAAA<br>GGCATTGTAGTTAGGAGTCACGAATATTTTAT<br>ATTTTTCAAAGCGAAAAAGGATCGATCCATTT<br>ATTTATATATTAATATTAAATGAATATA<br>TGTTTTTGTTGGTATATTAAAGCGGTGGTCAT<br>TGTTTAATAAGAAAAGCTGTGCACATATGTGA<br>AAAGAAAATGACAAAATCAGTATGAGTGGTCT<br>TATTTAGGAAGTTATGATGGTCATGTTAACAA<br>ATGCTTTAAGAATATTAGTAAAAGTAATAAC<br>GTCACTTTTGTATTGACAATAATGATTTTTAA<br>ATTTAAAAAAAAAAAAAGAAAAAATTAAGTA<br>CAGCAATTTGAAATACGATTTTGTTAACATAA<br>TCATGTAATAATAATTATTGCAAAAATGA<br>ATAGTTGTAATTAGGTGTCACGCTATAAAATA<br>AAATTAAACAAAAGGTGGGTTTGGTTCGAAAA<br>GTAAGAAATAGTTTTAAATTAGATTGAGAGAG<br>TTGTTGTGGATATCTACTATAAGTAGCGGCAA<br>TATGAATGAGTCTTTCCTCATATCAATCAAAT<br>TAAGGAGGTCTTGCTAGCTTCCATATATAACT<br>CATCACTAAAACTTCTAATAATTGAAAAAAAG<br>TAATTAAG |
| pCYP93E2 | (SEQ ID NO: 23)<br>AAAATAATATGTCATTGTAGACATGTTTTCTT<br>TTTGCCTACTACCATAAGAATCTTTTCCTAGT<br>AGGCGTCCAAAATATTTAGATTTAAATATTAT<br>AATTATTATTTTAGATTTAAATGTATTTATTA<br>TTACTTTTAATCGAATAGTTTAGAGGCGAGAA<br>GAAACACACAATAAATATTAAGAAGTGGAAAA<br>TTCAAAATTAGAACCCGAGATCAAAAACTTGC<br>GGTTTTCAACCCGGGATCATACTAACAAGTGT<br>CATAAATATTTTGTTTAAAGAATACTCTCTGG<br>TAACATTTATAAGCAAAAAAAACTTTTTAGGT<br>ACATTGAATAACTAATATATATGACATATAAA<br>TGTGACCAGATACATTGATTATTCAATGAATT<br>TAAAATGCTGATTTTTACTTACAAATTTGATC<br>GGAGGGAGTACATAAAAAGAAAATTTATATTA<br>GAAATATAAATCAAACATACGTCGAAGTCATA<br>TATACATCATTTTTTATGCAAAAGTTGCAATT<br>CCTAACAATGTTCTCACGATATTTGTTAGCCT<br>TTCTCAATTAAAAATGTATTTTTAAAATAATT<br>TGCGAGTGTGTAAATTAACATTGGGATTATAC<br>AAGTATTCTCAACCATTTATTCATCAAGACAA<br>AACAAAATCTTAACAATTTACCATAAATAAAC<br>ATAAAAAACACGTATCAATCACACACCGTTAG<br>CTGACAAACAACGTCAGCAATCATGAAATTAT<br>TTTATGTACCACGAGGGACACATAAGCAACAT<br>TCTTATTATAATATTCGACCACGAGGATCGCA<br>AAAATTAATAACTTAACTTCACTCAACAGTAC<br>CATTCAAAATCATACTAGACCAAGTCAAATTT<br>GTTCTTCTATTTATGTTCCATCATAGTTCAAG<br>AATTTAGATTCATCTTAAGCATAGACGTTGAG<br>TTGTGTTTGGTATTTTGCATTGACAACATTGT<br>CCTTTTTTGTCACACCAATTACCAAATCAAGT<br>ACTCAACC |
| pUGT73F3 | (SEQ ID NO: 24)<br>TTATCGTAATATATGATCAATATTCTCTATTA<br>TGAGTTACAAAAAAAGAAAAAAAATCAATTT<br>TATTTCGCCAACACGTTTTGTAAATAAGATTT<br>AGTTATTAAAGTTATAAAGACTAGCGAAAAGA<br>CGGGTACTCACGTGCCCGTCTTTCCGCTCTTT<br>TTATTGCGCTAATGTTTGAAAATTATGAATGA<br>TGTTTTTTTTATGAAATTTTGATTTTGATTAA<br>AACTAAAAAATATATAAATGTTTGTTTCTTTC<br>AACTTATAAAATCAACTAACTATGATTATCT<br>ATTTTCAACAACACCCACAATAATACAATATAA<br>CAAAAATATAATCTAAATTCCTTTTTAATGA<br>CAGCAACAACAATTTTATTATAGAAAAGTTG<br>TTTAAGGATATAATTGGAATGATGAAAAGTA<br>AGTATATTCATATCGTGTTTGTTACATTTGTT<br>TTAATATTCAAATTTATTCTTATCTAATTGTT<br>ACATGTATTATTTGTATTAAAAAATTTTGGAA<br>AGAAAAATATAACCAAAAATACTGAAAGGGA<br>TAGTTCTCTTTATATATAGTATAGATAAAAAA<br>TATTTCTTTTTCAAAATAAAAACTCATTTAA<br>TTATTAATATAAATCATATGTATCTGATACA<br>TTTAAATTTTCGAGTGTAGCATGTAGTTGTCA<br>TTTGGGAATGCACAACAAATTGTATCTGATAC<br>AATTTTTTCTTTTGAAGGATGAAGTTACAATC<br>TTTAATTTAGTATTAATAGTCGGCATTCAAAA<br>CTAAGATGGAAATCTCGCGGAAAAGATTCCTC<br>TCCTCGTGGGACACGAGCACATAGATCATAGA<br>TAAACTAATAACAAAAACAACATATAATATTA<br>AAGAAGTAAATTATTTATGTTAAACCAAAGTA<br>TGGTTGAAATTGAATATATAGAGATGCACTCA<br>CAGTGACAAACACAAACATAGAAACGTGAATA<br>GAATAGAATAGAATAGAGAATAAATTTGATC<br>CATAAGCA |
| pUGT73K1 | (SEQ ID NO: 25)<br>TTTTATCTATGGAGTGACTTTATGAAGACATC<br>CACCAAATTATCTTTCGATGCAACTTTCTCAG<br>TAATAATTTTCTTAAGTCTGATCTACAACAAA<br>CCATATCATACATGGTGCTTCCTACGACACTT<br>GCATATGGTGTACCCTCCATCTTCTCATCCTC<br>AAATTGAGGATAATGCATAGTCAAAAGTTTTG<br>TGTGATGATCCAAAGGAATCTCAGTGGTCATA<br>GCACTACTCTTTATGAGTTGTCCCACCACTTT<br>CTTTAGGTAAACATATTGAGATAAGAAAAATT<br>CATCCTTGTCCTAGTTTTTCCGGTATTTTTT |

TABLE 2-continued

Gene and promoter sequences

| ID | Sequence |
|---|---|
| | CAAGTATACTCTTAGCAACAACAAAAAATTTC<br>ATCTCAAGCTAGGGGACTAAGTTGTCCCTTGT<br>ATAAAAAACGAGACACTAATTTGGTATTATCT<br>CTTGTCAGGAACTAATTTGTGTGATGAAACTC<br>AGATACACTAAATGTTTCATTATACGTAGTCT<br>TCGTGAGCATAGCTCAGTTGACAAGGCAATA<br>CATAATATCGCAAGGTTTGAGTTCAAATCTCA<br>GACACAAAAAAAAAAATGTAAAAAATTATATG<br>TACGAATTTGTGCTTCAATATATTAAATATTG<br>TTAAACTTTATCATCTGAATTGTACTTATAAA<br>AATGTCCACTCTAGGATCAAATATAGAAAATA<br>ATAAGATTCAATCATTTACAAAAAATATTTTA<br>AAAATTATTCACGCAGTTCACGAGTACAGTTT<br>TTATCAATATAAACAATGAACAATAAACTAAT<br>AAAATATGCAGCCCGTGTATCTCGCTATTGCA<br>AGTATATATATTTTAATGAATCATTTCGTTTT<br>CTTTGGACCGTCTTTTAATTTAGATAAATAATA<br>GTGACAAATAATACATTCATAATTCATCAATC<br>AACCCCTTTTATAAACACTTCTAAGTTGTAAC<br>AGATTTAGAACACAGAGCACTAAACCAAGAAG<br>AAGAAAAAAGAGAAGTAGAAGAATCACATAAG<br>CTAAAAAA |

TABLE 3

Primer sequences

| Primer | SEQ ID | Sequence 5' to 3' |
|---|---|---|
| P1 | 26 | GGGGACAAGTTTGTACAAAAAAGCAGGC<br>TTAATGGAGGATTCACTGGAAAATTTG |
| P2 | 27 | GGGGACCACTTTGTACAAGAAAGCTGGG<br>TATCMCAAGTAACTCTCATGAG |
| P3 | 28 | GGGGACAAGTTTGTACAAAAAAGCAGGC<br>TTAATGGAGGAGAATCCATGGG |
| P4 | 29 | GGGGACCACTTTGTACAAGAAAGCTGGG<br>TATCMGATATGAAATTGCACATTATG |
| P5 | 30 | GGGGACAAGTTTGTACAAAAAAGCAGGC<br>TTAATGGAGGAAATCAACAACTC |
| P6 | 31 | GGGGACCACTTTGTACAAGAAAGCTGGG<br>TATTATGATGACGTAAACTTCAATAATG |
| P7 | 32 | GGGGACAAGTTTGTACAAAAAAGCAGGC<br>TTAATGGAGGAAATCAACAACAC |
| P8 | 33 | GGGGACCACTTTGTACAAGAAAGCTGGG<br>TATCAGTCTGTGATTTTTGATGAC |
| P9 | 34 | GGGGACAAGTTTGTACAAAAAAGCAGGC<br>TTAATTGGTAGGATCAATTGTTG |
| P10 | 35 | GGGGACCACTTTGTACAAGAAAGCTGGG<br>TACTCTCTCTCTCTTTCTCTTGG |
| P11 | 36 | GGGGACAAGTTTGTACAAAAAAGCAGGC<br>TTATAATTAATTAATTTGTAGTAGTC |
| P12 | 37 | GGGGACCACTTTGTACAAGAAAGCTGGG<br>TACTTAATTACTTTTTTCAATTATTAG |
| P13 | 38 | GGGGACAAGTTTGTACAAAAAAGCAGGC<br>TTAAAAATAATATGTCATTGTAGACATG |
| P14 | 39 | GGGGACCACTTTGTACAAGAAAGCTGGG<br>TAGGTTGAGTACTTGATTTGG |
| P15 | 40 | GGGGACAAGTTTGTACAAAAAAGCAGGC<br>TTATTATCGTAATATATGATCAATATTC |
| P16 | 41 | GGGGACCACTTTGTACAAGAAAGCTGGG<br>TATGCTTATGGATCAAATTATTCTC |
| P17 | 42 | GGGGACAAGTITGTACAAAAAAGCAGGC<br>TTATITTATCTATGGAGTGACTTTATG |
| P18 | 43 | GGGGACCACTTTGTACAAGAAAGCTGGG<br>TATTTTTTAGCTTATGTGATTCTTC |
| P19 | 44 | GGGGACAAGTTTGTACAAAAAAGCAGGC<br>TGTATGACAATGATGATGACGATG |
| P20 | 45 | GGGGACCACTTTGTACAAGAAAGCTGGG<br>TATCAATCTTCTAAATTTGCACGC |
| P21 | 46 | GGGGACAAGTTTGTACAAAAAAGCAGGC<br>TGTATGATGACGATGATGATGGATAA |
| P22 | 47 | GGGGACCACTTTGTACAAGAAAGCTGGG<br>TATCAGTCTGCCATTGGTGGACTG |

The invention claimed is:

1. A chimeric gene comprising the following operably-linked nucleic acid sequences:

one or more control sequences able to drive expression of a nucleic acid sequence in a plant cell; and a nucleic acid sequence encoding a BHLH protein of subfamily IVa comprising a bHLH domain wherein the nucleic acid sequence is SEQ ID NO: 15.

2. A transgenic plant comprising:
   the chimeric gene of claim 1.

3. A plant cell comprising:
   the chimeric gene of claim 1.

4. A vector comprising the chimeric gene of claim 1.

5. The chimeric gene of claim 1, further comprising:
   a transcript termination nucleic acid sequence operably-linked thereto.

* * * * *

UNITED STATES PATENT AND TRADEMARK OFFICE
CERTIFICATE OF CORRECTION

PATENT NO. : 10,370,672 B2  
APPLICATION NO. : 15/119681  
DATED : August 6, 2019  
INVENTOR(S) : Alain Goossens et al.

Page 1 of 1

It is certified that error appears in the above-identified patent and that said Letters Patent is hereby corrected as shown below:

On the Title Page

Item (73), please replace "VIB XVZW" with --VIB VZW--

Signed and Sealed this  
Seventeenth Day of September, 2019

Andrei Iancu  
*Director of the United States Patent and Trademark Office*

SEQUENCE LISTING

<160> NUMBER OF SEQ ID NOS: 83

<210> SEQ ID NO 1
<211> LENGTH: 1008
<212> TYPE: DNA
<213> ORGANISM: Medicago truncatula

<400> SEQUENCE: 1

```
atggaggatt cactggaaaa tttgatttct tatatggaaa tggaagatga tgtgatcttg      60
aatcaaagta gcaccaccac atttgatgag caagagtttc tcaaagatat catccttgaa     120
gaaccagaat gtattgaact ctcttcttat ctttgttcca ataaaaccaa agacaatagt     180
acaactataa ttaatgttga aggtgatgct actagcccca caaatagtat tttgtccttt     240
gatgagacaa gtttatttg tggtgattat gagaatgttg aaacaaacca caaaagtaat     300
aactccaact caatcaagtc tttggaaaga tcttgtgtta gttctccagc cacatacctt     360
```

```
ctatcttttg gtaactcaag tattgaacca atcattgaac caatgtcaca taaaactaaa    420
agaaggacag atgaatcaag gggggtgaag gaagcaacaa agaaggttag aagatcatgt    480
gagacagtac aagatcattt gatggctgag aggaaaagga aagggaatt aactgagaat     540 atcatagcac tttcagccat gatacctggc ttgaaaaaga tggacaagtg ttatgtactt    600
agcgaagctg tgaattacac aaaacagctt caaaagcgca ttaaagaatt ggagaatcaa    660
aacaaagata gcaaaccaaa tccagcaata ttcaagtgga aatctcaagt ttcatcaaat    720
aaaaagaagt cctcagaatc actgctcgag gttgaagcta gagtcaaaga aaggaagta    780 ctcatcagaa ttcattgtga aagcaaaaa gacatagtgc tcaaaataca tgaattgctt    840
gaaaagttca atatcactat aacaagtagt agcatgttac catttggtga ttctattctt    900
gtaatcaaca tttgtgctca gatggatgaa gaagacagca tgaccatgga tgaccttgtg    960
gaaaatctga gaaatatct attggaaact catgagagtt acttgtga                 1008
```

```
<210> SEQ ID NO 2
<211> LENGTH: 882
<212> TYPE: DNA
<213> ORGANISM: Medicago truncatula

<400> SEQUENCE: 2
atggaggaga atccatgggg caattggtct tatgatttgg aaatggaaga acatttgtgt     60
cacacaaaca acacatttga cgaagagttc ctcagagata tcctgtatca gattccacaa    120
gatcaattca atgttcctat tgccacaact gacctagtaa acaactcatc catcaatgtg    180
tcacaacatg ctgaagaaat gccaaccaac tcattatcaa taccaacaac tgaacaacat    240
catgattctt tgcctttgtc atcatcaaca gctaaccaag ggtcgaattc gaagaagcct    300
cgaaacactt cggatacact agatcacata atgtcagaga gaaataggag acaactactt    360
acaagtaaga tcatagaact ttcggccttg atacctggat tgaagaagat tgataaggtt    420
catgtggtaa cggaagctat caattacatg aaacaacttg aagaacgttt gaaagagcta    480
gaagaagaca ttaagaagaa agatgcagga tcattgagca ccataacaag atctcgtgtt    540
ttaattgaca aagacattgc aatcggtgaa atgaacactg aagaatgtta cgggagaaat    600
gaatcacttc tagaggttga agctaggatt ctagagaagg aagttttaat caagatttat    660
tgtggaatgc aagaagggat tgtggtcaat ataatgtccc agcttcaact tcttcatctg    720
tccataacaa gtatcaatgt cttgccattt ggaaatactc ttgacatcac cattattgcc    780
aagatgggtg acaaatacaa cttgacaata aaggacctag tgaaaaaact aagagtagtg    840
gctacgttgc aggtatctca taatgtgcaa tttcatatct aa                       882
```

```
<210> SEQ ID NO 3
<211> LENGTH: 990
<212> TYPE: DNA
<213> ORGANISM: Medicago truncatula

<400> SEQUENCE: 3
atggaggaaa tcaacaactc agctatgaaa gtatcatcat caatcagcag ctggttatct     60
gatttggaaa tggacgaata caatatattt gctgaggaat gcaaccttaa ttccttgat    120 gctgatgtgg gagggtttct ttcaaatgac atatctaatg tatttcaaga acaaaacaaa    180
caacaatgtt tatctttggg gtccactttt catgaaacaa ttgataatag tgacaaaaac    240
aatgaatctc tttctccatc ttttcagttt caagttccat cttttgacaa cccccccaaat    300
```

```
tcatccccta ctaactcaaa agagaatatt gaaacaatac cattgtctcc aaccgatttg      360
gaaaatatga atcactcaac agaaacctca aaagggtcat tggaaaataa aaagttggaa      420
acaaaaacct caaaaagcaa aaggccacgt gctcatggta gagatcacat catggctgag      480
agaaatcgaa gagagaaact cacccaaagc ttcattgctc ttgcagctct tgttcctaac      540
cttaagaaga tggataaact atctgtacta attgacacta tcaaatacat gaaagagctt      600
aaaaatcgtt tggaagatgt ggaagaacaa acaagaaaaa caaaaaaaaa atcatcgacc      660
aaaccatgcc tatgcagcga tgaagattcg tcatcatgtg aggataacat tgaatgtgtt      720
gttggttcac catttcaagt ggaagcaaga gtgttaggaa acaagtgct gattcggatc       780 caatgcaagg agcataaggg gcttctggtt aaaattatgg tcgaaattca aaaatttcaa      840
ctatttgttg tcaataacag tgtcttaccc tttggagatt ctacgctcga cattaccatc      900
attgctcagt tgggtgaagg gtacaacttg agcataaagg aacttgtgaa gaacgtacgc      960
atggcattat tgaagtttac gtcatcataa                                      990

<210> SEQ ID NO 4
<211> LENGTH: 1152
<212> TYPE: DNA
<213> ORGANISM: Medicago truncatula

<400> SEQUENCE: 4
atggaggaaa tcaacaacac accaatgaac gtatcagaag aaaccagcaa atggctatct       60
gatttggaaa tggatgagta taatttattt cctgaagaat gcaacctaaa cttccttgat      120
gctgatgagg aagagtttct tccacaagaa caaacccaac aacaatgttt gagttcagag      180
tccaattcca caactttcac caactcattc actgatgaaa caaattttga ctcttttgac      240
tttgattttg aaattgagag accaaccatg gagctgaaca caatctttag tgacaacagc      300
atcattgaaa ccatttcacc aaaactttct ccatcatcat ctaactcatc tttgcactct      360
cagattttgt cttttgacaa cctcccaaat tcacctgcta ccaacacccc tcaattttgt      420
ggactcaccc ctaccttaat ctcaaagtca aaacaaaaca aaacagtgtt agtgtctcca      480
ccccaaataa gaaacattca tgtctcaact caaaatccta tagggttatc caaaaatcaa      540
aactttgcaa caaaaacctc tcaaaccaaa aggtctcgag ccaacgctga tgatcatatc      600
atggctgaga gaaagcgaag agagaaactt agccaaagct tcattgctct tgcagctctt      660
gttcctaact tgaaaaagat ggacaaggct tctgtattag ctgagtctat aatctacgtg      720
aaagagctta agagcgtttt ggaagttttg gaagaacaaa acaagaaaac aaaggtagag      780
tccgtggttg ttctgaagaa accagaccat agtatcgatg atgatgatga tgatgatgat      840
aactcatcat gtgatgagag tattgaaggt gctactgatt catccgtaca agtgcaagca      900
agagtgtcag ggaaagagat gctgattcgg attcactgcg agaagcacaa gggaattctg      960
gtgaaagtca tggctgagat tcaaagcttt caattgtttg ctgtgaatag tagtgtctta     1020
ccctttgggg attccattga cattactatc attgctgaga tgggtgaaag gtacaacttg     1080
agcataaagg aacttgtcaa gaacctacac atggcagcat tgaagtttat gtcatcaaaa     1140
atcacagact ga                                                        1152

<210> SEQ ID NO 5
<211> LENGTH: 335
<212> TYPE: PRT
<213> ORGANISM: Medicago truncatula

<400> SEQUENCE: 5
```

Met Glu Asp Ser Leu Glu Asn Leu Ile Ser Tyr Met Glu Met Glu Asp
1               5                   10                  15

Asp Val Ile Leu Asn Gln Ser Ser Thr Thr Phe Asp Glu Gln Glu
            20                  25                  30

Phe Leu Lys Asp Ile Ile Leu Glu Glu Pro Glu Cys Ile Glu Leu Ser
            35                  40                  45

Ser Tyr Leu Cys Ser Asn Lys Thr Lys Asp Asn Ser Thr Thr Ile Ile
50                  55                  60

Asn Val Glu Gly Asp Ala Thr Ser Pro Thr Asn Ser Ile Leu Ser Phe
65                  70                  75                  80

Asp Glu Thr Ser Leu Phe Cys Gly Asp Tyr Glu Asn Val Glu Thr Asn
            85                  90                  95

His Lys Ser Asn Asn Ser Asn Ser Ile Lys Ser Leu Glu Arg Ser Cys
            100                 105                 110

Val Ser Ser Pro Ala Thr Tyr Leu Leu Ser Phe Gly Asn Ser Ser Ile
            115                 120                 125

Glu Pro Ile Ile Glu Pro Met Ser His Lys Thr Lys Arg Arg Thr Asp
            130                 135                 140

Glu Ser Arg Gly Val Lys Glu Ala Thr Lys Lys Val Arg Arg Ser Cys
145                 150                 155                 160

Glu Thr Val Gln Asp His Leu Met Ala Glu Arg Lys Arg Arg Arg Glu
            165                 170                 175

Leu Thr Glu Asn Ile Ile Ala Leu Ser Ala Met Ile Pro Gly Leu Lys
            180                 185                 190

Lys Met Asp Lys Cys Tyr Val Leu Ser Glu Ala Val Asn Tyr Thr Lys
            195                 200                 205

Gln Leu Gln Lys Arg Ile Lys Glu Leu Glu Asn Gln Asn Lys Asp Ser
            210                 215                 220

Lys Pro Asn Pro Ala Ile Phe Lys Trp Lys Ser Gln Val Ser Ser Asn
225                 230                 235                 240

Lys Lys Lys Ser Ser Glu Ser Leu Leu Glu Val Glu Ala Arg Val Lys
            245                 250                 255

Glu Lys Glu Val Leu Ile Arg Ile His Cys Gly Lys Gln Lys Asp Ile
            260                 265                 270

Val Leu Lys Ile His Glu Leu Leu Glu Lys Phe Asn Ile Thr Ile Thr
            275                 280                 285

Ser Ser Ser Met Leu Pro Phe Gly Asp Ser Ile Leu Val Ile Asn Ile
            290                 295                 300

Cys Ala Gln Met Asp Glu Glu Asp Ser Met Thr Met Asp Asp Leu Val
305                 310                 315                 320

Glu Asn Leu Arg Lys Tyr Leu Leu Glu Thr His Glu Ser Tyr Leu
            325                 330                 335

<210> SEQ ID NO 6
<211> LENGTH: 293
<212> TYPE: PRT
<213> ORGANISM: Medicago truncatula

<400> SEQUENCE: 6

Met Glu Glu Asn Pro Trp Gly Asn Trp Ser Tyr Asp Leu Glu Met Glu
1               5                   10                  15

Glu His Leu Cys His Thr Asn Asn Thr Phe Asp Glu Glu Phe Leu Arg
            20                  25                  30

Asp Ile Leu Tyr Gln Ile Pro Gln Asp Gln Phe Asn Val Pro Ile Ala

```
            35                  40                  45
Thr Thr Asp Leu Val Asn Asn Ser Ser Ile Asn Val Ser Gln His Ala
 50                  55                  60
Glu Glu Met Pro Thr Asn Ser Leu Ser Ile Pro Thr Thr Glu Gln His
 65                  70                  75                  80
His Asp Ser Leu Pro Leu Ser Ser Ser Thr Ala Asn Gln Gly Ser Asn
                 85                  90                  95
Ser Lys Lys Pro Arg Asn Thr Ser Asp Thr Leu Asp His Ile Met Ser
            100                 105                 110
Glu Arg Asn Arg Arg Gln Leu Leu Thr Ser Lys Ile Ile Glu Leu Ser
        115                 120                 125
Ala Leu Ile Pro Gly Leu Lys Lys Ile Asp Lys Val His Val Val Thr
    130                 135                 140
Glu Ala Ile Asn Tyr Met Lys Gln Leu Glu Gly Arg Leu Lys Glu Leu
145                 150                 155                 160
Glu Glu Asp Ile Lys Lys Asp Ala Gly Ser Leu Ser Thr Ile Thr
                165                 170                 175
Arg Ser Arg Val Leu Ile Asp Lys Asp Ile Ala Ile Gly Glu Met Asn
            180                 185                 190
Thr Glu Glu Cys Tyr Gly Arg Asn Glu Ser Leu Leu Glu Val Glu Ala
        195                 200                 205
Arg Ile Leu Glu Lys Glu Val Leu Ile Lys Ile Tyr Cys Gly Met Gln
    210                 215                 220
Glu Gly Ile Val Val Asn Ile Met Ser Gln Leu Gln Leu Leu His Leu
225                 230                 235                 240
Ser Ile Thr Ser Ile Asn Val Leu Pro Phe Gly Asn Thr Leu Asp Ile
                245                 250                 255
Thr Ile Ile Ala Lys Met Gly Asp Lys Tyr Asn Leu Thr Ile Lys Asp
            260                 265                 270
Leu Val Lys Lys Leu Arg Val Val Ala Thr Leu Gln Val Ser His Asn
        275                 280                 285
Val Gln Phe His Ile
    290

<210> SEQ ID NO 7
<211> LENGTH: 329
<212> TYPE: PRT
<213> ORGANISM: Medicago truncatula

<400> SEQUENCE: 7

Met Glu Glu Ile Asn Asn Ser Ala Met Lys Val Ser Ser Ser Ile Ser
 1               5                  10                  15
Ser Trp Leu Ser Asp Leu Glu Met Asp Glu Tyr Asn Ile Phe Ala Glu
            20                  25                  30
Glu Cys Asn Leu Asn Phe Leu Asp Ala Asp Val Gly Gly Phe Leu Ser
        35                  40                  45
Asn Asp Ile Ser Asn Val Phe Gln Glu Gln Asn Lys Gln Gln Cys Leu
    50                  55                  60
Ser Leu Gly Ser Thr Phe His Glu Thr Ile Asp Asn Ser Asp Lys Asn
 65                  70                  75                  80
Asn Glu Ser Leu Ser Pro Ser Phe Gln Phe Gln Val Pro Ser Phe Asp
                 85                  90                  95
Asn Pro Pro Asn Ser Ser Pro Thr Asn Ser Lys Glu Asn Ile Glu Thr
            100                 105                 110
```

```
Ile Pro Leu Ser Pro Thr Asp Leu Glu Asn Met Asn His Ser Thr Glu
            115                 120                 125

Thr Ser Lys Gly Ser Leu Glu Asn Lys Leu Glu Thr Lys Thr Ser
130                 135                 140

Lys Ser Lys Arg Pro Arg Ala His Gly Arg Asp His Ile Met Ala Glu
145                 150                 155                 160

Arg Asn Arg Arg Glu Lys Leu Thr Gln Ser Phe Ile Ala Leu Ala Ala
                165                 170                 175

Leu Val Pro Asn Leu Lys Lys Met Asp Lys Leu Ser Val Leu Ile Asp
            180                 185                 190

Thr Ile Lys Tyr Met Lys Glu Leu Lys Asn Arg Leu Glu Asp Val Glu
        195                 200                 205

Glu Gln Asn Lys Lys Thr Lys Lys Ser Ser Thr Lys Pro Cys Leu
    210                 215                 220

Cys Ser Asp Glu Asp Ser Ser Cys Glu Asp Asn Ile Glu Cys Val
225                 230                 235                 240

Val Gly Ser Pro Phe Gln Val Glu Ala Arg Val Leu Gly Lys Gln Val
                245                 250                 255

Leu Ile Arg Ile Gln Cys Lys Glu His Lys Gly Leu Leu Val Lys Ile
            260                 265                 270

Met Val Glu Ile Gln Lys Phe Gln Leu Phe Val Val Asn Asn Ser Val
        275                 280                 285

Leu Pro Phe Gly Asp Ser Thr Leu Asp Ile Thr Ile Ala Gln Leu
    290                 295                 300

Gly Glu Gly Tyr Asn Leu Ser Ile Lys Glu Leu Val Lys Asn Val Arg
305                 310                 315                 320

Met Ala Leu Leu Lys Phe Thr Ser Ser
                325

<210> SEQ ID NO 8
<211> LENGTH: 383
<212> TYPE: PRT
<213> ORGANISM: Medicago truncatula

<400> SEQUENCE: 8

Met Glu Glu Ile Asn Asn Thr Pro Met Asn Val Ser Glu Glu Thr Ser
1               5                   10                  15

Lys Trp Leu Ser Asp Leu Glu Met Asp Glu Tyr Asn Leu Phe Pro Glu
            20                  25                  30

Glu Cys Asn Leu Asn Phe Leu Asp Ala Asp Glu Glu Glu Phe Leu Pro
        35                  40                  45

Gln Glu Gln Thr Gln Gln Gln Cys Leu Ser Ser Glu Ser Asn Ser Thr
    50                  55                  60

Thr Phe Thr Asn Ser Phe Thr Asp Glu Thr Asn Phe Asp Ser Phe Asp
65                  70                  75                  80

Phe Asp Phe Glu Ile Glu Arg Pro Thr Met Glu Leu Asn Thr Ile Phe
                85                  90                  95

Ser Asp Asn Ser Ile Ile Glu Thr Ile Ser Pro Lys Leu Ser Pro Ser
            100                 105                 110

Ser Ser Asn Ser Ser Leu His Ser Gln Ile Leu Ser Phe Asp Asn Leu
        115                 120                 125

Pro Asn Ser Pro Ala Thr Asn Thr Pro Gln Phe Cys Gly Leu Thr Pro
    130                 135                 140

Thr Leu Ile Ser Lys Ser Lys Gln Asn Lys Thr Val Leu Val Ser Pro
145                 150                 155                 160
```

```
Pro Gln Ile Arg Asn Ile His Val Ser Thr Gln Asn Pro Ile Gly Leu
            165                 170                 175

Ser Lys Asn Gln Asn Phe Ala Thr Lys Thr Ser Gln Thr Lys Arg Ser
        180                 185                 190

Arg Ala Asn Ala Asp Asp His Ile Met Ala Glu Arg Lys Arg Arg Glu
        195                 200                 205

Lys Leu Ser Gln Ser Phe Ile Ala Leu Ala Ala Leu Val Pro Asn Leu
    210                 215                 220

Lys Lys Met Asp Lys Ala Ser Val Leu Ala Glu Ser Ile Ile Tyr Val
225                 230                 235                 240

Lys Glu Leu Lys Glu Arg Leu Glu Val Leu Glu Gln Asn Lys Lys
                245                 250                 255

Thr Lys Val Glu Ser Val Val Leu Lys Lys Pro Asp His Ser Ile
                260                 265                 270

Asp Asp Asp Asp Asp Asp Asp Asn Ser Ser Cys Asp Glu Ser Ile
        275                 280                 285

Glu Gly Ala Thr Asp Ser Ser Val Gln Val Gln Ala Arg Val Ser Gly
        290                 295                 300

Lys Glu Met Leu Ile Arg Ile His Cys Glu Lys His Lys Gly Ile Leu
305                 310                 315                 320

Val Lys Val Met Ala Glu Ile Gln Ser Phe Gln Leu Phe Ala Val Asn
                325                 330                 335

Ser Ser Val Leu Pro Phe Gly Asp Ser Ile Asp Ile Thr Ile Ile Ala
                340                 345                 350

Glu Met Gly Glu Arg Tyr Asn Leu Ser Ile Lys Glu Leu Val Lys Asn
                355                 360                 365

Leu His Met Ala Ala Leu Lys Phe Met Ser Ser Lys Ile Thr Asp
    370                 375                 380

<210> SEQ ID NO 9
<211> LENGTH: 56
<212> TYPE: PRT
<213> ORGANISM: Medicago truncatula

<400> SEQUENCE: 9

Thr Val Gln Asp His Leu Met Ala Glu Arg Lys Arg Arg Glu Leu
1               5                   10                  15

Thr Glu Asn Ile Ile Ala Leu Ser Ala Met Ile Pro Gly Leu Lys Lys
                20                  25                  30

Met Asp Lys Cys Tyr Val Leu Ser Glu Ala Val Asn Tyr Thr Lys Gln
            35                  40                  45

Leu Gln Lys Arg Ile Lys Glu Leu
    50                  55

<210> SEQ ID NO 10
<211> LENGTH: 56
<212> TYPE: PRT
<213> ORGANISM: Medicago truncatula

<400> SEQUENCE: 10

Asp Thr Leu Asp His Ile Met Ser Glu Arg Asn Arg Arg Gln Leu Leu
1               5                   10                  15

Thr Ser Lys Ile Ile Glu Leu Ser Ala Leu Ile Pro Gly Leu Lys Lys
                20                  25                  30

Ile Asp Lys Val His Val Val Thr Glu Ala Ile Asn Tyr Met Lys Gln
            35                  40                  45
```

```
Leu Glu Glu Arg Leu Lys Glu Leu
    50                  55
```

<210> SEQ ID NO 11
<211> LENGTH: 56
<212> TYPE: PRT
<213> ORGANISM: Medicago truncatula

<400> SEQUENCE: 11

```
His Gly Arg Asp His Ile Met Ala Glu Arg Asn Arg Arg Glu Lys Leu
1               5                   10                  15

Thr Gln Ser Phe Ile Ala Leu Ala Ala Leu Val Pro Asn Leu Lys Lys
            20                  25                  30

Met Asp Lys Leu Ser Val Leu Ile Asp Thr Ile Lys Tyr Met Lys Glu
        35                  40                  45

Leu Lys Asn Arg Leu Glu Asp Val
    50                  55
```

<210> SEQ ID NO 12
<211> LENGTH: 56
<212> TYPE: PRT
<213> ORGANISM: Medicago truncatula

<400> SEQUENCE: 12

```
Asn Ala Asp Asp His Ile Met Ala Glu Arg Lys Arg Arg Glu Lys Leu
1               5                   10                  15

Ser Gln Ser Phe Ile Ala Leu Ala Ala Leu Val Pro Asn Leu Lys Lys
            20                  25                  30

Met Asp Lys Ala Ser Val Leu Ala Glu Ser Ile Ile Tyr Val Lys Glu
        35                  40                  45

Leu Lys Glu Arg Leu Glu Val Leu
    50                  55
```

<210> SEQ ID NO 13
<211> LENGTH: 32
<212> TYPE: PRT
<213> ORGANISM: Artificial Sequence
<220> FEATURE:
<223> OTHER INFORMATION: bHLH domain
<220> FEATURE:
<221> NAME/KEY: MISC_FEATURE
<222> LOCATION: (1)..(1)
<223> OTHER INFORMATION: Xaa can be D or E
<220> FEATURE:
<221> NAME/KEY: MISC_FEATURE
<222> LOCATION: (3)..(3)
<223> OTHER INFORMATION: Xaa can be I, V or L
<220> FEATURE:
<221> NAME/KEY: MISC_FEATURE
<222> LOCATION: (4)..(4)
<223> OTHER INFORMATION: Xaa can be L, M, V or I
<220> FEATURE:
<221> NAME/KEY: MISC_FEATURE
<222> LOCATION: (8)..(8)
<223> OTHER INFORMATION: Xaa can be K, R or N
<220> FEATURE:
<221> NAME/KEY: MISC_FEATURE
<222> LOCATION: (11)..(11)
<223> OTHER INFORMATION: Xaa can be R, Q or E
<220> FEATURE:
<221> NAME/KEY: MISC_FEATURE
<222> LOCATION: (12)..(12)
<223> OTHER INFORMATION: Xaa can be any amino acid, preferably K, Q, E
    or D
<220> FEATURE:
<221> NAME/KEY: MISC_FEATURE
<222> LOCATION: (14)..(14)

```
<223> OTHER INFORMATION: Xaa can be T or S
<220> FEATURE:
<221> NAME/KEY: MISC_FEATURE
<222> LOCATION: (15)..(15)
<223> OTHER INFORMATION: Xaa can be E or Q
<220> FEATURE:
<221> NAME/KEY: MISC_FEATURE
<222> LOCATION: (16)..(16)
<223> OTHER INFORMATION: Xaa can be R, S, K or N
<220> FEATURE:
<221> NAME/KEY: MISC_FEATURE
<222> LOCATION: (17)..(17)
<223> OTHER INFORMATION: Xaa can be F, I or L
<220> FEATURE:
<221> NAME/KEY: MISC_FEATURE
<222> LOCATION: (18)..(18)
<223> OTHER INFORMATION: Xaa can be I, V or M
<220> FEATURE:
<221> NAME/KEY: MISC_FEATURE
<222> LOCATION: (21)..(21)
<223> OTHER INFORMATION: Xaa can be S or A
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: MISC_FEATURE
<222> LOCATION: (24)..(24)
<223> OTHER INFORMATION: Xaa can be V, I, L or P
<220> FEATURE:
<221> NAME/KEY: MISC_FEATURE
<222> LOCATION: (26)..(26)
<223> OTHER INFORMATION: Xaa can be G or N
<220> FEATURE:
<221> NAME/KEY: MISC_FEATURE
<222> LOCATION: (28)..(28)
<223> OTHER INFORMATION: Xaa can be K, N, S or R
<220> FEATURE:
<221> NAME/KEY: MISC_FEATURE
<222> LOCATION: (30)..(30)
<223> OTHER INFORMATION: Xaa can be any amino acid, preferably M or T

<400> SEQUENCE: 13

Xaa His Xaa Xaa Ala Glu Arg Xaa Arg Arg Xaa Xaa Leu Xaa Xaa Xaa
1               5                   10                  15

Xaa Xaa Ala Leu Xaa Ala Xaa Xaa Pro Xaa Leu Xaa Lys Xaa Asp Lys
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: Consensus motif characteristic for the group of
      bHLH25-like polypeptides

<400> SEQUENCE: 14

Asp His Ile Met Ala Glu Arg Lys Arg Arg Glu Lys Leu Thr Gln Arg
1               5                   10                  15

Phe Ile Ala Leu Ser Ala Leu Ile Pro Gly Leu Lys Lys Met Asp Lys
            20                  25                  30

<210> SEQ ID NO 15
<211> LENGTH: 1100
<212> TYPE: DNA
<213> ORGANISM: Catharanthus roseus

<400> SEQUENCE: 15
atgacaatga tgatgacgat ggataattca gtcaattcat ggttctctga tctgggaatg      60
gaggatcctt tctccagcga tcaatatgac atcacggact ttctgaatga ggatttcgct     120
```

```
gcacttggag aggacttgca agcattcact ccaacagccg aatctgattc atccaataac    180
ttcattaata ttccaactag caattcatca aacaccttat gtgcattggc tacggaactt    240
ccttcggttg tggccgaaat tccaaccacc atcactgcca ctaccactac taaaaaacga    300
aaatccaatt cgtcgacaaa tcaaaatgtg ccgaatgctc gtagagccgc tcgtactccc    360
atcgttctca catttgggaa tacacggcag aaaccaatcc taataaacac agcttaagcc    420
ctgatattaa tgatgattca ttaatatcaa ctgagaattt gacctcccaa ggaaatcttg    480
aagaggcagt agcagctgcc aaaagtacaa aactaaacaa gaaaactggt ggccgcgtta    540
ggcctgcatc ccaaacctat gatcacataa ttgctgaaag aaagcgacgt gagcagctca    600
gccagcattt tgtcgcactt tctgccattg ttcctggcct taagaagatg gataaaactt    660
ctgtacttgg agatgcgatt acctacttaa aacatatgca agagcgagta aaatcactag    720
aagaacaaac aacaaaacaa acaatggaat cagtggtgct agtgaagaaa tcacaagtgt    780
tagttgaaga tgaaggttct tcagatgaga ttgatcaaga tcagtcctcg tcacagctcc    840
ctgaaattga agccaaagtt tgtgacaaaa ccatttttact cagagttcac tgcgaaaaga    900
acaaaagggt ccttattaat atactctctc aacttgaaac actcaatctt gttgttacta    960
acaccagcgt ttcagctttt ggaagtttgg ctcttgatat tactatcatc gttgagatgg   1020
agaaagaatc aagcataaac atgaagaac ttattcaaac tcttcggtca gctgtcatgc   1080
gtgcaaattt agaagattga                                                1100

<210> SEQ ID NO 16
<211> LENGTH: 1242
<212> TYPE: DNA
<213> ORGANISM: Catharanthus roseus

<400> SEQUENCE: 16
atgatgacga tgatgatgga taattcagca acgtccccta attgcttctc tgagcttcag     60
cagggaatgg aggatcctac taacttcctc attagcaatg atgataaatg tgatgtaatg    120 gagttttttgg atgaagatat atgtgcagtt cttggtcaag actacttcca aatttcctct    180
ttctccccaa atgactactc attttctcca aacttggatc caaattccac tttatatcca    240
tcttcttctt caactcctac ggatattcat gaccaatctc caccatttat gcttaatgat    300
gatattgatg aaataatgaa tagacgacca gccaaacagc tgaagagcac tagtaataat    360
aatcaaaata accaaaatcc gtcgactatt catgatagct ttgatgctca aatgtctact    420
ccctaccttc ttacttttgg gaatccaaat tcacctgaaa ttattaatcc acctcatcat    480
caacaacacc atcaacctaa tgcaacatta aacttaaacc cctctgatga agatgttcaa    540
gtatccgagg ttttcaactc ccaaagttca tcatatggaa atcttattga agaggaggca    600
gcagcaccca aaagttcaaa accaacgtcc aagaaaagtg gaggccgtgt aaggccggct    660 tctcaaaactt atgatcacat tatagctgaa agaaagagaa gggagatcct cagccagcgc    720
tttatggctc tttctactct agttcccggt ctcaagaaga tggataaaac atcagtactt    780
ggagatgcaa ttaagtactt aaaatatctc caagaaagag ttcagattct tgaggatcaa    840
gcagccaaac aaactatgga atcggtggtg atggtgaaga atcacatgt cttcatccaa    900 gaagaagaag atgatgaaga aggatcttca gatgatcaga tcaccagcga tggcggaagc    960
tcagaagaac acccattacc tgaaattgag gttaaagttt gcaataaaac acttcttctg   1020
agaattcact gcgagaagca aaaagggggtg cttattaagt tacttaatga gattgaaagg   1080
ctcaatcttg gcgttaccaa cattaacgtt gcaccatttg gaagcttggc tcttgacatt   1140
```

-continued

```
accattattg ctgagatgga gaaagagtac aatatgacaa cggtacaagt gattaaaaat      1200
cttcggtcag ttcttcttaa cagtccacca atggcagact ga                        1242
```

<210> SEQ ID NO 17
<211> LENGTH: 366
<212> TYPE: PRT
<213> ORGANISM: Catharanthus roseus

<400> SEQUENCE: 17

```
Met Thr Met Met Met Thr Met Asp Asn Ser Val Asn Ser Trp Phe Ser
1               5                   10                  15

Asp Leu Gly Met Glu Asp Pro Phe Ser Asp Gln Tyr Asp Ile Thr
            20                  25                  30

Asp Phe Leu Asn Glu Asp Phe Ala Ala Leu Gly Glu Asp Leu Gln Ala
        35                  40                  45

Phe Thr Pro Thr Ala Glu Ser Asp Ser Ser Asn Asn Phe Ile Asn Ile
    50                  55                  60

Pro Thr Ser Asn Ser Ser Asn Thr Leu Cys Ala Leu Ala Thr Glu Leu
65                  70                  75                  80

Pro Ser Val Val Ala Glu Ile Pro Thr Thr Ile Thr Ala Thr Thr Thr
                85                  90                  95

Thr Lys Lys Arg Lys Ser Asn Ser Ser Thr Asn Gln Asn Val Pro Asn
            100                 105                 110

Ala Arg Arg Ala Ala Arg Thr Pro Ile Val Leu Thr Phe Gly Asn Thr
        115                 120                 125

Thr Ala Glu Thr Asn Pro Asn Lys His Ser Leu Ser Pro Asp Ile Asn
    130                 135                 140

Asp Asp Ser Leu Ile Ser Thr Glu Asn Leu Thr Ser Gln Gly Asn Leu
145                 150                 155                 160

Glu Glu Ala Val Ala Ala Ala Lys Ser Thr Lys Leu Asn Lys Lys Thr
                165                 170                 175

Gly Gly Arg Val Arg Pro Ala Ser Gln Thr Tyr Asp His Ile Ile Ala
            180                 185                 190

Glu Arg Lys Arg Arg Glu Gln Leu Ser Gln His Phe Val Ala Leu Ser
        195                 200                 205

Ala Ile Val Pro Gly Leu Lys Lys Met Asp Lys Thr Ser Val Leu Gly
    210                 215                 220

Asp Ala Ile Thr Tyr Leu Lys His Met Gln Glu Arg Val Lys Ser Leu
225                 230                 235                 240

Glu Glu Gln Thr Thr Lys Gln Thr Met Glu Ser Val Val Leu Val Lys
                245                 250                 255

Lys Ser Gln Val Leu Val Glu Asp Glu Gly Ser Ser Asp Glu Ile Asp
            260                 265                 270

Gln Asp Gln Ser Ser Ser Gln Leu Pro Glu Ile Glu Ala Lys Val Cys
        275                 280                 285

Asp Lys Thr Ile Leu Leu Arg Val His Cys Glu Lys Asn Lys Arg Val
    290                 295                 300

Leu Ile Asn Ile Leu Ser Gln Leu Glu Thr Leu Asn Leu Val Val Thr
305                 310                 315                 320

Asn Thr Ser Val Ser Ala Phe Gly Ser Leu Ala Leu Asp Ile Thr Ile
                325                 330                 335

Ile Val Glu Met Glu Lys Glu Ser Ser Ile Asn Met Lys Glu Leu Ile
            340                 345                 350
```

Gln Thr Leu Arg Ser Ala Val Met Arg Ala Asn Leu Glu Asp
            355                 360                 365

<210> SEQ ID NO 18
<211> LENGTH: 413
<212> TYPE: PRT
<213> ORGANISM: Catharanthus roseus

<400> SEQUENCE: 18

Met Met Thr Met Met Met Asp Asn Ser Ala Thr Ser Pro Asn Cys Phe
1               5                   10                  15

Ser Glu Leu Gln Gln Gly Met Glu Asp Pro Thr Asn Phe Leu Ile Ser
            20                  25                  30

Asn Asp Asp Lys Cys Asp Val Met Glu Phe Leu Asp Glu Asp Ile Cys
        35                  40                  45

Ala Val Leu Gly Gln Asp Tyr Phe Gln Ile Ser Ser Phe Ser Pro Asn
    50                  55                  60

Asp Tyr Ser Phe Ser Pro Asn Leu Asp Pro Asn Ser Thr Leu Tyr Pro
65                  70                  75                  80

Ser Ser Ser Ser Thr Pro Thr Asp Ile His Asp Gln Ser Pro Pro Phe
                85                  90                  95

Met Leu Asn Asp Asp Ile Asp Glu Ile Met Asn Arg Arg Pro Ala Lys
            100                 105                 110

Gln Leu Lys Ser Thr Ser Asn Asn Asn Gln Asn Gln Asn Pro Ser
        115                 120                 125

Thr Ile His Asp Ser Phe Asp Ala Gln Met Ser Thr Pro Tyr Leu Leu
    130                 135                 140

Thr Phe Gly Asn Pro Asn Ser Pro Glu Ile Ile Asn Pro Pro His His
145                 150                 155                 160

Gln Gln His His Gln Pro Asn Ala Thr Leu Asn Leu Asn Pro Ser Asp
                165                 170                 175

Glu Asp Val Gln Val Ser Glu Val Phe Asn Ser Gln Ser Ser Ser Tyr
            180                 185                 190

Gly Asn Leu Ile Glu Glu Ala Ala Ala Pro Lys Ser Ser Lys Pro
        195                 200                 205

Thr Ser Lys Lys Ser Gly Gly Arg Val Arg Pro Ala Ser Gln Thr Tyr
    210                 215                 220

Asp His Ile Ile Ala Glu Arg Lys Arg Arg Glu Ile Leu Ser Gln Arg
225                 230                 235                 240

Phe Met Ala Leu Ser Thr Leu Val Pro Gly Leu Lys Lys Met Asp Lys
                245                 250                 255

Thr Ser Val Leu Gly Asp Ala Ile Lys Tyr Leu Lys Tyr Leu Gln Glu
            260                 265                 270

Arg Val Gln Ile Leu Glu Asp Gln Ala Ala Lys Gln Thr Met Glu Ser
        275                 280                 285

Val Val Met Val Lys Lys Ser His Val Phe Ile Gln Glu Glu Glu Asp
    290                 295                 300

Asp Glu Glu Gly Ser Ser Asp Asp Gln Ile Thr Ser Asp Gly Gly Ser
305                 310                 315                 320

Ser Glu Glu His Pro Leu Pro Glu Ile Glu Val Lys Val Cys Asn Lys
                325                 330                 335

Thr Leu Leu Leu Arg Ile His Cys Glu Lys Gln Lys Gly Val Leu Ile
            340                 345                 350

Lys Leu Leu Asn Glu Ile Glu Arg Leu Asn Leu Gly Val Thr Asn Ile
        355                 360                 365

```
Asn Val Ala Pro Phe Gly Ser Leu Ala Leu Asp Ile Thr Ile Ile Ala
    370                 375                 380

Glu Met Glu Lys Glu Tyr Asn Met Thr Thr Val Gln Val Ile Lys Asn
385                 390                 395                 400

Leu Arg Ser Val Leu Leu Asn Ser Pro Pro Met Ala Asp
            405                 410

<210> SEQ ID NO 19
<211> LENGTH: 56
<212> TYPE: PRT
<213> ORGANISM: Catharanthus roseus

<400> SEQUENCE: 19

Gln Thr Tyr Asp His Ile Ile Ala Glu Arg Lys Arg Arg Glu Gln Leu
1               5                   10                  15

Ser Gln His Phe Val Ala Leu Ser Ala Ile Val Pro Gly Leu Lys Lys
                20                  25                  30

Met Asp Lys Thr Ser Val Leu Gly Asp Ala Ile Thr Tyr Leu Lys His
            35                  40                  45

Met Gln Glu Arg Val Lys Ser Leu
    50                  55

<210> SEQ ID NO 20
<211> LENGTH: 56
<212> TYPE: PRT
<213> ORGANISM: Catharanthus roseus

<400> SEQUENCE: 20

Gln Thr Tyr Asp His Ile Ile Ala Glu Arg Lys Arg Arg Glu Ile Leu
1               5                   10                  15

Ser Gln Arg Phe Met Ala Leu Ser Thr Leu Val Pro Gly Leu Lys Lys
                20                  25                  30

Met Asp Lys Thr Ser Val Leu Gly Asp Ala Ile Lys Tyr Leu Lys Tyr
            35                  40                  45

Leu Gln Glu Arg Val Gln Ile Leu
    50                  55

<210> SEQ ID NO 21
<211> LENGTH: 1000
<212> TYPE: DNA
<213> ORGANISM: Artificial Sequence
<220> FEATURE:
<223> OTHER INFORMATION: Promoter

<400> SEQUENCE: 21
attggtagga tcaattgttg attgtcttgg tttatgtaaa atgttaaaat gtgacaatta      60
aaaagaaacg gaggtagtac ttctatcata tttaatgcta ttacttctaa attcgttttc     120
aattatttat gtttgaatcc tccgagtgtc aattttttgtt gatttgttta tagtgggatt    180
ggtcctttgg attagtcggt tcttgaatca atactaaat  tttcaaacaa aaatttagat     240
tttacttttc tataaccatt ttattatcat agaaaaaaaa attaaatctc cgaaaaatta    300
tcatgaacaa gttttcatga gggacaattt agaaatgca  attatggcta aactatgttt    360
caagtccctt aaattgttca ttttgttcac ttaaattaca acattgagt  tattcaaata    420 aaaattacaa acattgagta agaaaacaaa attaaacacg ttttttgactt tagattcgat   480 tcatattaaa cacatttgag tcaaaaacaa aattaaacac gttttttttg cagcacaagt    540
gatgtataaa actaattagt ttttatttca gcaacaaaaa atgtacttat agtttgatta    600
```

```
gtttgtgcaa ataagaaata tatatagtat tttagaaacg tcaagtaaag gcttcttcta    660
gtgatgtgta atgttggcat ctctcctcca taaaatatgt tatcttggag taaaagttag    720
gtactgatta caatattctt ccctcgttgt tcacgagttc cttacgatct agctatcaag    780
ctactgttac ttgacttctt aaaatattgg catataccta attcctcact cactccctga    840
gtactcttta tctataaata acattcaaaa taaatcttgg cattcatttt caagttaagt    900
ttcaatcatc ccctaacctg aactccttt tctccttct ttttccattt tcggatttca    960
aatccttcac ttaataacca agagaaagag agagagagag                         1000
```

```
<210> SEQ ID NO 22
<211> LENGTH: 1000
<212> TYPE: DNA
<213> ORGANISM: Artificial Sequence
<220> FEATURE:
<223> OTHER INFORMATION: Promoter

<400> SEQUENCE: 22
taattaatta atttgtagta gtcctcgttt gtgaccacgc ttccctcgtg tttcatttat    60
tttatcctgc tctccacgct atactcgcta catatataat aataatcaat gaatgtatat    120
tgttaaattc catcctgttc accaataatg attgaattca agaattaatt ttaaatatat    180
attctaaaat aaaaggaaac tgcaaaaaat aaacgatgaa tcatatgaga caaaaatgaa    240
gagataacac ttatactgct taattattat cattgtaaag ataaattgag aagaatacat    300
gacggcaact gcaactcaat ggaagaacac ttacaagatg tatatgaaaa cacctacttc    360
aaaaatgtac attaaagcga aaaaggcatt gtagttagga gtcacgaata ttttatattt    420
ttcaaagcga aaaaggatcg atccatttat ttatatatta ttaatattaa atgaatata    480 tgttttttgtt ggtatattaa agcggtggtc attgtttaat aagaaaagct gtgcacatat    540
gtgaaaagaa aatgacaaaa tcagtatgag tggtcttatt taggaagtta tgatggtcat    600
gttaacaaat gctttaagaa tattagtaaa aagtaataac gtcacttttg tattgacaat    660
aatgattttt aaatttaaaa aaaaaaaaa gaaaaaatta agtacagcaa tttgaaatac    720 gatttttgtta acataatcat gtaataaata atattattgc aaaaatgaat agttgtaatt    780
aggtgtcacg ctataaaata aaataaacaa aaaggtgggt ttggttcgaa agtaagaaa    840 tagttttaaa ttagattgag agagttgttg tggatatcta ctataagtag cggcaatatg    900
aatgagtctt tcctcatatc aatcaaatta aggaggtctt gctagcttcc atatataact    960
catcactaaa acttctaata attgaaaaaa agtaattaag                         1000
```

```
<210> SEQ ID NO 23
<211> LENGTH: 1000
<212> TYPE: DNA
<213> ORGANISM: Artificial Sequence
<220> FEATURE:
<223> OTHER INFORMATION: Promoter

<400> SEQUENCE: 23
aaaataatat gtcattgtag acatgttttc tttttgccta ctaccataag aatcttttcc    60
tagtaggcgt ccaaaatatt tagatttaaa tattataatt attatttag atttaaatgt    120 atttattatt actttttaatc gaatagttta gaggcgagaa gaaacacaca ataaatatta    180
agaagtggaa aattcaaaat tagaacccga gatcaaaaac ttgcggtttt caacccggga    240
tcatactaac aagtgtcata atatttttgt ttaaagaata ctctctggta acatttataa    300
```

```
gcaaaaaaaa cttttttaggt acattgaata actaatatat atgacatata aatgtgacca    360
gatacattga ttattcaatg aatttaaaat gctgattttt acttacaaat ttgatcggag    420
ggagtacata aaaagaaaat ttatattaga aatataaatc aaacatacgt cgaagtcata    480
tatacatcat ttttatgca aaagttgcaa ttcctaacaa tgttctcacg atatttgtta    540
gcctttctca attaaaaatg tatttttaaa ataatttgcg agtgtgtaaa ttaacattgg    600
gattatacaa gtattctcaa ccatttattc atcaagacaa aacaaaatct taacaattta    660
ccataaataa acataaaaaa cacgtatcaa tcacacaccg ttagctgaca aacaacgtca    720
gcaatcatga aattatttta tgtaccacga gggacacata agcaacattc ttattataat    780
attcgaccac gaggatcgca aaaattaata acttaacttc actcaacagt accattcaaa    840
atcatactag accaagtcaa atttgttctt ctatttatgt tccatcatag ttcaagaatt    900
tagattcatc ttaagcatag acgttgagtt gtgtttggta ttttgcattg acaacattgt    960
ccttttttgt cacaccaatt accaaatcaa gtactcaacc                         1000
```

<210> SEQ ID NO 24
<211> LENGTH: 1000
<212> TYPE: DNA
<213> ORGANISM: Artificial Sequence
<220> FEATURE:
<223> OTHER INFORMATION: Promoter

<400> SEQUENCE: 24

```
ttatcgtaat atatgatcaa tattctctat tatgagttac aaaaaaaga aaaaaaatca     60 attttatttc gccaacacgt tttgtaaata agatttagtt attaaagtta taagagactag   120 cgaaaagacg ggtactcacg tgcccgtctt tccgctcttt ttattgcgct aatgtttgaa   180
aattatgaat gatgtttttt ttatgaaatt ttgattttga ttaaaactaa aaaatatata   240
aatgtttgtt tctttcaact tataaaaatc aactaactat gattatctat ttcaacaaca   300
cccacaataa tacaatataa caaaaaatat aatctaaatt ccttttttaat gacagcaaca   360 acaattttat tatagaaaaa gttgtttaag gatataattg gaatgatgaa aaagtaagta   420
tattcatatc gtgtttgtta catttgtttt aatattcaaa tttattctta tctaattgtt   480
acatgtatta tttgtattaa aaaattttgg aaagaaaaat ataaccaaaa aatactgaaa   540
gggatagttc tctttatata tagtatagat aaaaaatatt tcttttttcaa aataaaaaac   600 tcatttaatt attaatataa aatcatatgt atctgataca tttaaatttt cgagtgtagc   660
atgtagttgt catttgggaa tgcacaacaa attgtatctg atacaatttt ttcttttgaa   720
ggatgaagtt acaatcttta atttagtatt aatagtcggc attcaaaact aagatggaaa   780
tctcgcggaa aagattcctc tcctcgtggg acacgagcac atagatcata gataaactaa   840
taacaaaaac aacatataat attaaagaag taaattattt atgttaaacc aaagtatggt   900
tgaaattgaa tatatagaga tgcactcaca gtgacaaaca caaacataga aacgtgaata   960
gaatagaata gaatagagag aataaatttga tccataagca                        1000
```

<210> SEQ ID NO 25
<211> LENGTH: 1000
<212> TYPE: DNA
<213> ORGANISM: Artificial Sequence
<220> FEATURE:
<223> OTHER INFORMATION: Promoter

<400> SEQUENCE: 25

```
ttttatctat ggagtgactt tatgaagaca tccaccaaat tatctttcga tgcaactttc     60
```

```
tcagtaataa ttttcttaag tctgatctac aacaaaccat atcatacatg gtgcttccta      120
cgacacttgc atatggtgta ccctccatct tctcatcctc aaattgagga taatgcatag      180
tcaaaagttt tgtgtgatga tccaaaggaa tctcagtggt catagcacta ctctttatga      240
gttgtcccac cactttcttt aggtaaacat attgagataa gaaaaattca tccttgtcct      300 agttttccg gtattttttt caagtatact cttagcaaca acaaaaaatt tcatctcaag       360
ctaggggact aagttgtccc ttgtataaaa acgagacac taatttggta ttatctcttg       420
tcaggaacta atttgtgtga tgaaactcag atacactaaa tgtttcatta tacgtagtct      480
tcgtgagcat agctcagttg acaaggacaa tacataatat cgcaaggttt gagttcaaat      540
ctcagacaca aaaaaaaaaa tgtaaaaaat tatatgtacg aatttgtgct tcaatatatt      600
aaatattgtt aaactttatc atctgaattg tacttataaa aatgtccact ctaggatcaa      660
atatagaaaa taataagatt caatcattta caaaaaatat tttaaaaatt attcacgcag      720
ttcacgagta cagtttttat caatataaac aatgaacaat aaactaataa aatatgcagc      780
ccgtgtatct cgctattgca agtatatata ttttaatgaa tcatttcgtt ttctttggac      840
cgtctttaat ttagataaat aatagtgaca aataatacat tcataattca tcaatcaacc      900 cctttttataa acacttctaa gttgtaacag atttagaaca cagagcacta aaccaagaag     960
aagaaaaaag agaagtagaa gaatcacata agctaaaaaa                           1000
```

```
<210> SEQ ID NO 26
<211> LENGTH: 55
<212> TYPE: DNA
<213> ORGANISM: artificial
<220> FEATURE:
<223> OTHER INFORMATION: Primer

<400> SEQUENCE: 26
ggggacaagt ttgtacaaaa aagcaggctt aatggaggat tcactggaaa atttg          55

<210> SEQ ID NO 27
<211> LENGTH: 50
<212> TYPE: DNA
<213> ORGANISM: artificial
<220> FEATURE:
<223> OTHER INFORMATION: Primer

<400> SEQUENCE: 27
ggggaccact ttgtacaaga aagctgggta tcmcaagtaa ctctcatgag                 50

<210> SEQ ID NO 28
<211> LENGTH: 50
<212> TYPE: DNA
<213> ORGANISM: artificial
<220> FEATURE:
<223> OTHER INFORMATION: Primer

<400> SEQUENCE: 28
ggggacaagt ttgtacaaaa aagcaggctt aatggaggag aatccatggg                 50

<210> SEQ ID NO 29
<211> LENGTH: 54
<212> TYPE: DNA
<213> ORGANISM: artificial
<220> FEATURE:
<223> OTHER INFORMATION: Primer

<400> SEQUENCE: 29
```

```
gggaccact ttgtacaaga aagctgggta tcmgatatga aattgcacat tatg        54
```

<210> SEQ ID NO 30
<211> LENGTH: 51
<212> TYPE: DNA
<213> ORGANISM: artificial
<220> FEATURE:
<223> OTHER INFORMATION: Primer

<400> SEQUENCE: 30

```
ggggacaagt ttgtacaaaa aagcaggctt aatggaggaa atcaacaact c          51
```

<210> SEQ ID NO 31
<211> LENGTH: 56
<212> TYPE: DNA
<213> ORGANISM: artificial
<220> FEATURE:
<223> OTHER INFORMATION: Primer

<400> SEQUENCE: 31

```
ggggaccact ttgtacaaga aagctgggta ttatgatgac gtaaacttca ataatg     56
```

<210> SEQ ID NO 32
<211> LENGTH: 51
<212> TYPE: DNA
<213> ORGANISM: artificial
<220> FEATURE:
<223> OTHER INFORMATION: Primer

<400> SEQUENCE: 32

```
ggggacaagt ttgtacaaaa aagcaggctt aatggaggaa atcaacaaca c          51
```

<210> SEQ ID NO 33
<211> LENGTH: 52
<212> TYPE: DNA
<213> ORGANISM: artificial
<220> FEATURE:
<223> OTHER INFORMATION: Primer

<400> SEQUENCE: 33

```
ggggaccact ttgtacaaga aagctgggta tcagtctgtg attttgatg ac          52
```

<210> SEQ ID NO 34
<211> LENGTH: 51
<212> TYPE: DNA
<213> ORGANISM: artificial
<220> FEATURE:
<223> OTHER INFORMATION: Primer

<400> SEQUENCE: 34

```
ggggacaagt ttgtacaaaa aagcaggctt aattggtagg atcaattgtt g          51
```

<210> SEQ ID NO 35
<211> LENGTH: 53
<212> TYPE: DNA
<213> ORGANISM: artificial
<220> FEATURE:
<223> OTHER INFORMATION: Primer

<400> SEQUENCE: 35

```
ggggaccact ttgtacaaga aagctgggta ctctctctct ctctttctct tgg        53
```

<210> SEQ ID NO 36
<211> LENGTH: 54
<212> TYPE: DNA
<213> ORGANISM: artificial

```
<220> FEATURE:
<223> OTHER INFORMATION: Primer

<400> SEQUENCE: 36
ggggacaagt ttgtacaaaa aagcaggctt ataattaatt aatttgtagt agtc        54

<210> SEQ ID NO 37
<211> LENGTH: 56
<212> TYPE: DNA
<213> ORGANISM: artificial
<220> FEATURE:
<223> OTHER INFORMATION: Primer

<400> SEQUENCE: 37
ggggaccact ttgtacaaga aagctgggta cttaattact tttttcaat tattag       56

<210> SEQ ID NO 38
<211> LENGTH: 56
<212> TYPE: DNA
<213> ORGANISM: artificial
<220> FEATURE:
<223> OTHER INFORMATION: Primer

<400> SEQUENCE: 38
ggggacaagt ttgtacaaaa aagcaggctt aaaaataata tgtcattgta gacatg      56

<210> SEQ ID NO 39
<211> LENGTH: 49
<212> TYPE: DNA
<213> ORGANISM: artificial
<220> FEATURE:
<223> OTHER INFORMATION: Primer

<400> SEQUENCE: 39
ggggaccact ttgtacaaga aagctgggta ggttgagtac ttgatttgg              49

<210> SEQ ID NO 40
<211> LENGTH: 56
<212> TYPE: DNA
<213> ORGANISM: artificial
<220> FEATURE:
<223> OTHER INFORMATION: Primer

<400> SEQUENCE: 40
ggggacaagt ttgtacaaaa aagcaggctt attatcgtaa tatatgatca atattc      56

<210> SEQ ID NO 41
<211> LENGTH: 53
<212> TYPE: DNA
<213> ORGANISM: artificial
<220> FEATURE:
<223> OTHER INFORMATION: Primer

<400> SEQUENCE: 41
ggggaccact ttgtacaaga aagctgggta tgcttatgga tcaaattatt ctc         53

<210> SEQ ID NO 42
<211> LENGTH: 55
<212> TYPE: DNA
<213> ORGANISM: artificial
<220> FEATURE:
<223> OTHER INFORMATION: Primer

<400> SEQUENCE: 42
ggggacaagt ttgtacaaaa aagcaggctt attttatcta tggagtgact ttatg       55
```

-continued

<210> SEQ ID NO 43
<211> LENGTH: 53
<212> TYPE: DNA
<213> ORGANISM: artificial
<220> FEATURE:
<223> OTHER INFORMATION: Primer

<400> SEQUENCE: 43
ggggaccact ttgtacaaga aagctgggta ttttttagct tatgtgattc ttc        53

<210> SEQ ID NO 44
<211> LENGTH: 52
<212> TYPE: DNA
<213> ORGANISM: artificial
<220> FEATURE:
<223> OTHER INFORMATION: Primer

<400> SEQUENCE: 44
ggggacaagt ttgtacaaaa aagcaggctg tatgacaatg atgatgacga tg         52

<210> SEQ ID NO 45
<211> LENGTH: 52
<212> TYPE: DNA
<213> ORGANISM: artificial
<220> FEATURE:
<223> OTHER INFORMATION: Primer

<400> SEQUENCE: 45
ggggaccact ttgtacaaga aagctgggta tcaatcttct aaatttgcac gc         52

<210> SEQ ID NO 46
<211> LENGTH: 54
<212> TYPE: DNA
<213> ORGANISM: artificial
<220> FEATURE:
<223> OTHER INFORMATION: Primer

<400> SEQUENCE: 46
ggggacaagt ttgtacaaaa aagcaggctg tatgatgacg atgatgatgg ataa       54

<210> SEQ ID NO 47
<211> LENGTH: 52
<212> TYPE: DNA
<213> ORGANISM: artificial
<220> FEATURE:
<223> OTHER INFORMATION: Primer

<400> SEQUENCE: 47
ggggaccact ttgtacaaga aagctgggta tcagtctgcc attggtggac tg         52

<210> SEQ ID NO 48
<211> LENGTH: 32
<212> TYPE: PRT
<213> ORGANISM: Theobroma cacao

<400> SEQUENCE: 48

Asp His Ile Met Ala Glu Arg Lys Arg Arg Glu Lys Leu Ser Gln Arg
1               5                   10                  15

Phe Ile Ala Leu Ser Ala Ile Val Pro Gly Leu Lys Lys Met Asp Lys
            20                  25                  30

<210> SEQ ID NO 49
<211> LENGTH: 32
<212> TYPE: PRT
<213> ORGANISM: Fragaria vesca

<400> SEQUENCE: 49

Asp His Ile Met Ala Glu Arg Lys Arg Arg Glu Lys Leu Ser Gln Arg
1               5                   10                  15

Phe Ile Ala Leu Ser Ala Ile Val Pro Gly Leu Lys Lys Met Asp Lys
            20                  25                  30

<210> SEQ ID NO 50
<211> LENGTH: 32
<212> TYPE: PRT
<213> ORGANISM: Malus domestica
<220> FEATURE:
<221> NAME/KEY: misc_feature
<222> LOCATION: (24)..(24)
<223> OTHER INFORMATION: Xaa can be any naturally occurring amino acid

<400> SEQUENCE: 50

Asp His Ile Met Ala Glu Arg Lys Arg Arg Glu Lys Leu Ser Gln Arg
1               5                   10                  15

Phe Ile Ala Leu Ser Ala Ile Xaa Pro Gly Leu Lys Lys Met Asp Lys
            20                  25                  30

<210> SEQ ID NO 51
<211> LENGTH: 32
<212> TYPE: PRT
<213> ORGANISM: Carica papaya

<400> SEQUENCE: 51

Asp His Ile Val Ala Glu Arg Lys Arg Arg Glu Lys Leu Ser Gln Arg
1               5                   10                  15

Phe Ile Ala Leu Ser Ala Ile Val Pro Gly Leu Lys Lys Met Asp Lys
            20                  25                  30

<210> SEQ ID NO 52
<211> LENGTH: 32
<212> TYPE: PRT
<213> ORGANISM: Zea mays

<400> SEQUENCE: 52

Asp His Ile Leu Ala Glu Arg Lys Arg Arg Glu Lys Leu Ser Gln Arg
1               5                   10                  15

Phe Ile Ala Leu Ser Lys Ile Val Pro Gly Leu Lys Lys Met Asp Lys
            20                  25                  30

<210> SEQ ID NO 53
<211> LENGTH: 32
<212> TYPE: PRT
<213> ORGANISM: Oryza sativa

<400> SEQUENCE: 53

Glu His Ile Leu Ala Glu Arg Lys Arg Arg Glu Lys Leu Ser Gln Arg
1               5                   10                  15

Phe Ile Ala Leu Ser Lys Ile Val Pro Gly Leu Lys Lys Met Asp Lys
            20                  25                  30

<210> SEQ ID NO 54
<211> LENGTH: 32
<212> TYPE: PRT
<213> ORGANISM: Manihot esculenta

<400> SEQUENCE: 54

Asp His Ile Leu Ala Glu Arg Lys Arg Arg Glu Lys Leu Ser Gln Arg
1               5                   10                  15

Phe Ile Ala Leu Ser Ala Ile Val Pro Gly Leu Lys Lys Met Asp Lys
            20                  25                  30

<210> SEQ ID NO 55
<211> LENGTH: 32
<212> TYPE: PRT
<213> ORGANISM: Arabidopsis thaliana

<400> SEQUENCE: 55

Glu His Val Leu Ala Glu Arg Lys Arg Arg Gln Lys Leu Asn Glu Arg
1               5                   10                  15

Leu Ile Ala Leu Ser Ala Leu Leu Pro Gly Leu Lys Lys Thr Asp Lys
            20                  25                  30

<210> SEQ ID NO 56
<211> LENGTH: 32
<212> TYPE: PRT
<213> ORGANISM: Arabidopsis thaliana

<400> SEQUENCE: 56

Glu His Val Leu Ala Glu Arg Lys Arg Arg Glu Lys Leu Ser Glu Lys
1               5                   10                  15

Phe Ile Ala Leu Ser Ala Leu Leu Pro Gly Leu Lys Lys Ala Asp Lys
            20                  25                  30

<210> SEQ ID NO 57
<211> LENGTH: 32
<212> TYPE: PRT
<213> ORGANISM: Malus domestica

<400> SEQUENCE: 57

Asp His Val Leu Ala Glu Arg Lys Arg Arg Glu Lys Leu Ser Gln Arg
1               5                   10                  15

Phe Ile Ala Leu Ser Ala Leu Leu Pro Gly Leu Lys Lys Met Asp Lys
            20                  25                  30

<210> SEQ ID NO 58
<211> LENGTH: 32
<212> TYPE: PRT
<213> ORGANISM: Fragaria vesca

<400> SEQUENCE: 58

Asp His Val Leu Ala Glu Arg Lys Arg Arg Glu Lys Leu Ser Gln Arg
1               5                   10                  15

Phe Ile Ala Leu Ser Ala Leu Val Pro Gly Leu Lys Lys Met Asp Lys
            20                  25                  30

<210> SEQ ID NO 59
<211> LENGTH: 32
<212> TYPE: PRT
<213> ORGANISM: Manihot esculenta

<400> SEQUENCE: 59

Asp His Val Leu Ala Glu Arg Lys Arg Arg Glu Lys Leu Ser Gln Arg
1               5                   10                  15

Phe Ile Ser Leu Ser Ala Val Val Pro Gly Leu Lys Lys Met Asp Lys
            20                  25                  30

<210> SEQ ID NO 60
<211> LENGTH: 32
<212> TYPE: PRT
<213> ORGANISM: Ricinus communis

```
<400> SEQUENCE: 60

Asp His Ile Leu Ala Glu Arg Lys Arg Arg Glu Lys Leu Ser Gln Arg
1               5                   10                  15

Phe Ile Ala Leu Ser Ala Leu Val Pro Gly Leu Lys Lys Met Asp Lys
            20                  25                  30

<210> SEQ ID NO 61
<211> LENGTH: 32
<212> TYPE: PRT
<213> ORGANISM: Populus trichocarpa

<400> SEQUENCE: 61

Asp His Ile Ile Ala Glu Arg Lys Arg Arg Glu Lys Leu Ser Gln Arg
1               5                   10                  15

Phe Ile Ala Leu Ser Ala Val Val Pro Gly Leu Lys Lys Met Asp Lys
            20                  25                  30

<210> SEQ ID NO 62
<211> LENGTH: 32
<212> TYPE: PRT
<213> ORGANISM: Catharanthus roseus

<400> SEQUENCE: 62

Asp His Ile Ile Ala Glu Arg Lys Arg Arg Glu Gln Leu Ser Gln His
1               5                   10                  15

Phe Val Ala Leu Ser Ala Ile Val Pro Gly Leu Lys Lys Met Asp Lys
            20                  25                  30

<210> SEQ ID NO 63
<211> LENGTH: 32
<212> TYPE: PRT
<213> ORGANISM: Catharanthus roseus

<400> SEQUENCE: 63

Asp His Ile Ile Ala Glu Arg Lys Arg Arg Glu Ile Leu Ser Gln Arg
1               5                   10                  15

Phe Met Ala Leu Ser Thr Leu Val Pro Gly Leu Lys Lys Met Asp Lys
            20                  25                  30

<210> SEQ ID NO 64
<211> LENGTH: 32
<212> TYPE: PRT
<213> ORGANISM: Arabidopsis thaliana

<400> SEQUENCE: 64

Asp His Ile Ile Ala Glu Arg Lys Arg Arg Glu Lys Leu Thr Gln Arg
1               5                   10                  15

Phe Val Ala Leu Ser Ala Leu Val Pro Gly Leu Lys Lys Met Asp Lys
            20                  25                  30

<210> SEQ ID NO 65
<211> LENGTH: 32
<212> TYPE: PRT
<213> ORGANISM: Malus domestica

<400> SEQUENCE: 65

Asp His Ile Ile Ala Glu Arg Lys Arg Arg Glu Lys Leu Thr Gln Arg
1               5                   10                  15

Phe Val Ala Leu Ser Ala Leu Val Pro Gly Leu Lys Lys Met Asp Lys
            20                  25                  30
```

<210> SEQ ID NO 66
<211> LENGTH: 32
<212> TYPE: PRT
<213> ORGANISM: Arabidopsis thaliana

<400> SEQUENCE: 66

Asp His Ile Leu Ala Glu Arg Lys Arg Arg Glu Lys Leu Thr Gln Arg
1               5                   10                  15

Phe Val Ala Leu Ser Ala Leu Ile Pro Gly Leu Lys Lys Met Asp Lys
            20                  25                  30

<210> SEQ ID NO 67
<211> LENGTH: 32
<212> TYPE: PRT
<213> ORGANISM: Vitis vinifera

<400> SEQUENCE: 67

Asp His Val Ile Ala Glu Arg Lys Arg Arg Gly Lys Leu Thr Gln Arg
1               5                   10                  15

Phe Ile Ala Leu Ser Ala Leu Val Pro Gly Leu Arg Lys Met Asp Lys
            20                  25                  30

<210> SEQ ID NO 68
<211> LENGTH: 32
<212> TYPE: PRT
<213> ORGANISM: Vitis vinifera

<400> SEQUENCE: 68

Asp His Val Val Ala Glu Arg Lys Arg Arg Glu Lys Leu Thr Gln Arg
1               5                   10                  15

Phe Ile Ala Leu Ser Ala Leu Val Pro Gly Leu Arg Lys Thr Asp Lys
            20                  25                  30

<210> SEQ ID NO 69
<211> LENGTH: 32
<212> TYPE: PRT
<213> ORGANISM: Medicago truncatula

<400> SEQUENCE: 69

Asp His Ile Met Ala Glu Arg Asn Arg Arg Glu Lys Leu Thr Gln Ser
1               5                   10                  15

Phe Ile Ala Leu Ala Ala Leu Val Pro Asn Leu Lys Lys Met Asp Lys
            20                  25                  30

<210> SEQ ID NO 70
<211> LENGTH: 32
<212> TYPE: PRT
<213> ORGANISM: Medicago truncatula

<400> SEQUENCE: 70

Asp His Ile Met Ala Glu Arg Lys Arg Arg Glu Lys Leu Ser Gln Ser
1               5                   10                  15

Phe Ile Ala Leu Ala Ala Leu Val Pro Asn Leu Lys Lys Met Asp Lys
            20                  25                  30

<210> SEQ ID NO 71
<211> LENGTH: 32
<212> TYPE: PRT
<213> ORGANISM: Glycine max

<400> SEQUENCE: 71

Asp His Ile Met Ala Glu Arg Lys Arg Arg Glu Lys Leu Ser Gln Ser

```
                1               5                  10                 15
             Phe Ile Ala Leu Ala Ala Leu Val Pro Gly Leu Lys Lys Met Asp Lys
                             20                25                30
```

<210> SEQ ID NO 72
<211> LENGTH: 32
<212> TYPE: PRT
<213> ORGANISM: Glycine max

<400> SEQUENCE: 72

```
Asp His Ile Met Ala Glu Arg Lys Arg Arg Glu Lys Leu Ser Gln Ser
1               5                  10                 15

Phe Ile Ala Leu Ala Ala Leu Val Pro Gly Leu Lys Lys Met Asp Lys
             20                25                30
```

<210> SEQ ID NO 73
<211> LENGTH: 32
<212> TYPE: PRT
<213> ORGANISM: Glycine max

<400> SEQUENCE: 73

```
Asp His Ile Ile Ala Glu Arg Lys Arg Arg Glu Lys Leu Ser Gln Ser
1               5                  10                 15

Leu Ile Ala Leu Ala Ala Leu Ile Pro Gly Leu Lys Lys Met Asp Arg
             20                25                30
```

<210> SEQ ID NO 74
<211> LENGTH: 32
<212> TYPE: PRT
<213> ORGANISM: Glycine max

<400> SEQUENCE: 74

```
Asp His Ile Ile Ala Glu Arg Lys Arg Arg Glu Lys Leu Ser Gln Ser
1               5                  10                 15

Leu Ile Ala Leu Ala Ala Leu Ile Pro Gly Leu Lys Lys Met Asp Lys
             20                25                30
```

<210> SEQ ID NO 75
<211> LENGTH: 32
<212> TYPE: PRT
<213> ORGANISM: Lotus japonicus

<400> SEQUENCE: 75

```
Asp His Ile Ile Ala Glu Arg Arg Arg Glu Lys Leu Ser Gln Ser
1               5                  10                 15

Leu Ile Ala Leu Ala Ala Leu Ile Pro Gly Leu Lys Lys Met Asp Lys
             20                25                30
```

<210> SEQ ID NO 76
<211> LENGTH: 32
<212> TYPE: PRT
<213> ORGANISM: Glycine max

<400> SEQUENCE: 76

```
Asp His Ile Met Ala Glu Arg Arg Arg Gln Glu Leu Thr Glu Arg
1               5                  10                 15

Phe Ile Ala Leu Ser Ala Thr Ile Pro Gly Leu Asn Lys Thr Asp Lys
             20                25                30
```

<210> SEQ ID NO 77
<211> LENGTH: 32
<212> TYPE: PRT

```
<213> ORGANISM: Glycine max

<400> SEQUENCE: 77

Asp His Ile Met Ala Glu Arg Arg Arg Gln Asp Leu Thr Glu Arg
1               5                   10                  15

Phe Ile Ala Leu Ser Ala Thr Ile Pro Gly Leu Ser Lys Thr Asp Lys
            20                  25                  30

<210> SEQ ID NO 78
<211> LENGTH: 32
<212> TYPE: PRT
<213> ORGANISM: Glycine max

<400> SEQUENCE: 78

Asp His Ile Met Ala Glu Arg Lys Arg Gln Asp Leu Thr Glu Arg
1               5                   10                  15

Phe Ile Ala Leu Ser Ala Thr Ile Pro Gly Leu Lys Lys Thr Asp Lys
            20                  25                  30

<210> SEQ ID NO 79
<211> LENGTH: 32
<212> TYPE: PRT
<213> ORGANISM: Glycine max

<400> SEQUENCE: 79

Asn His Ile Met Ala Glu Arg Lys Arg Arg Glu Leu Thr Glu Arg
1               5                   10                  15

Phe Ile Ala Leu Ser Ala Thr Ile Pro Gly Leu Lys Lys Thr Asp Lys
            20                  25                  30

<210> SEQ ID NO 80
<211> LENGTH: 32
<212> TYPE: PRT
<213> ORGANISM: Glycine max

<400> SEQUENCE: 80

Asp His Ile Met Thr Glu Arg Lys Arg Arg Glu Leu Thr Glu Arg
1               5                   10                  15

Phe Ile Ala Leu Ser Ala Thr Ile Pro Gly Leu Lys Lys Ile Asp Lys
            20                  25                  30

<210> SEQ ID NO 81
<211> LENGTH: 32
<212> TYPE: PRT
<213> ORGANISM: Medicago truncatula

<400> SEQUENCE: 81

Asp His Leu Met Ala Glu Arg Lys Arg Arg Glu Leu Thr Glu Asn
1               5                   10                  15

Ile Ile Ala Leu Ser Ala Met Ile Pro Gly Leu Lys Lys Met Asp Lys
            20                  25                  30

<210> SEQ ID NO 82
<211> LENGTH: 32
<212> TYPE: PRT
<213> ORGANISM: Medicago truncatula

<400> SEQUENCE: 82

Asp His Ile Met Ser Glu Arg Asn Arg Arg Gln Leu Leu Thr Ser Lys
1               5                   10                  15

Ile Ile Glu Leu Ser Ala Leu Ile Pro Gly Leu Lys Lys Ile Asp Lys
            20                  25                  30
```

```
<210> SEQ ID NO 83
<211> LENGTH: 32
<212> TYPE: PRT
<213> ORGANISM: Glycine max

<400> SEQUENCE: 83

Ser His Ile Met Ala Glu Arg Lys Arg Arg Gln Gln Leu Thr Gln Ser
1               5                   10                  15

Phe Ile Ala Leu Ser Ala Thr Ile Pro Gly Leu Asn Lys Lys Asp Lys
                20                  25                  30
```